(12) United States Patent
Bird et al.

(10) Patent No.: US 11,969,479 B2
(45) Date of Patent: Apr. 30, 2024

(54) MECP2 EXPRESSION CASSETTES

(71) Applicants: THE UNIVERSITY COURT OF THE UNIVERSITY OF EDINBURGH, Edinburgh (GB); THE UNIVERSITY COURT OF THE UNIVERSITY OF GLASGOW, Glasgow (GB)

(72) Inventors: Adrian Bird, Edinburgh (GB); Rebekah Tillotson, Edinburgh (GB); Stuart Robert Cobb, Edinburgh (GB); Ralph David Hector, Edinburgh (GB)

(73) Assignees: THE UNIVERSITY COURT OF THE UNIVERSITY OF EDINBURGH, Edinburgh (GB); THE UNIVERSITY COURT OF THE UNIVERSITY OF GLASGOW, Glasgow (GB)

( * ) Notice: Subject to any disclaimer, the term of this patent is extended or adjusted under 35 U.S.C. 154(b) by 1094 days.

(21) Appl. No.: 16/497,277

(22) PCT Filed: Mar. 23, 2018

(86) PCT No.: PCT/GB2018/050773
§ 371 (c)(1),
(2) Date: Sep. 24, 2019

(87) PCT Pub. No.: WO2018/172795
PCT Pub. Date: Sep. 27, 2018

(65) Prior Publication Data
US 2020/0016279 A1  Jan. 16, 2020

(30) Foreign Application Priority Data
Mar. 24, 2017 (GB) .................. 1704704
Mar. 24, 2017 (GB) .................. 1704722

(51) Int. Cl.
| | |
|---|---|
| *A61K 48/00* | (2006.01) |
| *A61K 9/00* | (2006.01) |
| *A61P 25/00* | (2006.01) |
| *A61P 25/14* | (2006.01) |
| *C07K 14/00* | (2006.01) |
| *C07K 14/47* | (2006.01) |
| *C12N 5/12* | (2006.01) |
| *C12N 7/00* | (2006.01) |
| *C12N 15/113* | (2010.01) |
| *C12N 15/86* | (2006.01) |
| *A61K 38/00* | (2006.01) |

(52) U.S. Cl.
CPC ........ *A61K 48/0066* (2013.01); *A61K 9/0019* (2013.01); *A61K 9/0085* (2013.01); *A61P 25/14* (2018.01); *C07K 14/001* (2013.01); *C07K 14/4703* (2013.01); *C12N 7/00* (2013.01); *C12N 15/86* (2013.01); *A61K 38/00* (2013.01); *C12N 2750/14143* (2013.01)

(58) Field of Classification Search
None
See application file for complete search history.

(56) References Cited

U.S. PATENT DOCUMENTS

| 7,939,634 B2 | 5/2011 | Ayalon-Soffer et al. | |
|---|---|---|---|
| 2006/0194257 A1* | 8/2006 | Minassian ............. | C07K 14/47 435/7.1 |
| 2010/0075891 A1 | 3/2010 | Ayalon-Soffer et al. | |
| 2011/0212051 A1* | 9/2011 | Ayalon-Soffer ......... | A61P 29/00 514/6.9 |
| 2013/0225666 A1 | 8/2013 | Kaspar et al. | |

FOREIGN PATENT DOCUMENTS

| WO | 2005078099 A1 | 8/2005 |
|---|---|---|
| WO | 20100105096 A2 | 9/2010 |

OTHER PUBLICATIONS

Newnham et al, Alternative polyadenylation of MeCP2: influence of cis-acting elements and trans-acting factors, RNA Biology 7:3, 361-372; May/Jun. 2010; pp. 361-372.*
Gadhalla et al, Improved Survival and Reduced Phenotypic Severity Following AAV9/MECP2 Gene Transfer to Neonatal and Juvenile Male Mecp2 Knockout Mice, Molecualr Therapy, 2013, p. 18-30.*
Non-Final Office Action dated Apr. 11, 2022 in U.S. Appl. No. 16/497,217.
Tuppy, Hans, "Epigenetics and Rett Syndrome," Hans Tuppy Lecture University of Vienna, Nov. 8, 2016, The Wellcome Trust Center for Cell Biology, University of Edinburgh, pp. 1-53.

(Continued)

*Primary Examiner* — Maria Marvich
(74) *Attorney, Agent, or Firm* — Troutman Pepper Hamilton Sanders LLP (Rochester)

(57) ABSTRACT

The present invention provides nucleic acid molecules comprising a MeCP2 expression cassette, the expression cassette comprising, in operable linkage from 5' to 3': a 5' transcriptional control region comprising a promoter capable of driving transcription in neural cells; an open reading frame encoding a MeCP2 protein; translation control signals; a 3' untranslated region (3'UTR) comprising one or more of: (i) a binding site for mir-22; (ii) a binding site for mir-19; (iii) a binding site for miR-132; (iv) a binding site for miR124; and (v) an AU-rich element; and transcriptional termination signals; wherein the MeCP2 expression cassette is not more than about 5 kb in length. The invention further provides viral vectors, especially vectors derived from adeno-associated virus (AAV), for use in therapeutic delivery of such expression cassettes. The nucleic acid molecules and viral vectors disclosed herein provide novel tools for expressing MeCP2 and are of particular value in the treatment of disorders associated with reduced MeCP2 activity, including Rett syndrome.

17 Claims, 18 Drawing Sheets
Specification includes a Sequence Listing.

(56) References Cited

OTHER PUBLICATIONS

Crick, Francis, "The Astonishing Hypothesis," Genetic and Epigenetic Roots of Rett Syndrome, Rockefeller University, Mar. 29, 2016, The Wellcome Trust Center for Cell Biology University of Edinburgh, pp. 1-32.
Flexner, Louis B, "DNA Methylation and Rett Syndrome," Louis B. Flexner Lecture, Aug. 17, 2016, University of Pennsylvania, The Wellcome Trust Center for Cell Biology University of Edinburgh, pp. 1-49.
"Genetic and Epigenetic Roots of Rett Syndrome," Milan 2016 Presentation, May 20, 2016, The Wellcome Trust Center for Cell Biology University of Edinburgh, pp. 1-49.
Tillotson, Rebekah, et als., "Testing The Bridge Hypothesis for MeCP2 Function," Poster, Les Diablerets, Switzerland, May 22-27, 2016 Presentation, The Wellcome Trust Center for Cell Biology University of Edinburgh.
"Genetic and Epigenetic Roots of Rett Syndrome," Mendel Barcelona Lecture European Society for Human Genetics, Barcelona, May 24, 2016, The Wellcome Trust Center for Cell Biology University of Edinburgh, pp. 1-48.
"Epigenetics and Rett Syndrome," London Chromatin Club, Jun. 30, 2016, The Wellcome Trust Center for Cell Biology University of Edinburgh, pp. 1-41.
"DNA Methylation and Rett Syndrome," Li Ka Shing Facility of Medicine Hong Kong University, Oct. 27, 2016, The Wellcome Trust Center for Cell Biology University of Edinburgh, pp. 1-48.
Gadalla et al., "Improved survival and reduced phenotypic severity following AAV9/MECP2 gene transfer . . . ", Molecular Therapy, vol. 21, pp. 18-30 (2013).
Lyu et al., "Reciprocal regulation of autism-related genes MeCP2 and PTEN via microRNAs", Sci Rep., vol. 6 (2016).
Geisler et al., "MicroRNA-regulated viral vectors for gene therapy", World J. Exp. Medicine, vol. 6, pp. 37-54 (2016).
Garg et al., "Systemic Delivery of MeCP2 Rescues Behavioral and Cellular Deficits in Female Mouse Models of Rett Syndrome", The Journal of Neuroscience: The Official Journal of the Society for Neuroscience, vol. 33, No. 34, (Aug. 21, 2013).
Gadalla et al., "Gene Therapy for Rett Syndrome: Prospects and Challenges", Future Neurology, vol. 10, No. 5, pp. 467-484 (Nov. 1, 2015).
McGowan et al., "Regulatory Functions and Pathological Relevance of the MECP2 3' UTR in the Central Nervous System", Cell Regeneration, BioMed Central Ltd., vol. 4, No. 1, p. 9 (Oct. 28, 2015).
Gadalla et al., "Development of a Novel AAV Gene Therapy Cassette With Improved Safety Features and Efficacy in a Mouse Model of Rett Syndrome", Molecular Therapy—Methods & Clinical Develop., vol. 5, pp. 180-190 (Jun. 1, 2017).
Kumar et al., "Analysis of Protein Domains and Rett Syndrome", Journal of Cell Science, vol. 121, pp. 1128-1137 (2008).
Yang et al., "Biophysical Analysis and Small-Angle X-Ray", Nucleic Acids Research, vol. 39, pp. 4122-4135 (2011).
Shahbazian et al., "Mice with truncated MeCP2 recapitulate many Rett . . . ", Neuron, vol. 35, pp. 243-254 (2002).
Lyst et al., "Rett syndrome mutations abolish the interaction of MECP2 . . . ", Nature Neuroscience, vol. 16, pp. 898-902 (2013).
Ravn et al ., "Two new Rett syndrome families and review of the literature: expanding teh knowledge of MECP2 frameshift mutations", Orphanet Journal of Rare Diseases, Biomed Central Ltd. Lo, vol. 5, No. 1, p. 58 (Aug. 30, 2011).
Shah et al., "MeCP2 mutations: progress towards understanding and treating Rett syndrome", Genome Medicine, vol. 9, No. 1, (Feb. 17, 2017).
Tillotson et al., Radically truncated MeCP2 rescues Rett syndrome-like neurological defects, Nature, vol. 550, No. 7676, pp. 398-401 (Oct. 19, 2017).

* cited by examiner

| Regulatory element (RE) | Reference |
|---|---|
| Silencer | Liu & Francke (2006)* |
| Promoter RE | Adachi et al. (2005); Liu & Francke (2006)*; Liyanage et al. (2013) |
| miR-22 binding site | Feng et al. (2014) |
| miR-19 binding site | Jovicic et al. (2013) |
| miR-132 binding site | Klein et al. (2007) |
| 3'-UTR RE | Coy et al. (1999); Newnham et al. (2010)*; Bagga & D'Antonio (2013)* |
| TATAAA polyadenylation signal | Coy et al. (1999); Newnham et al. (2010)*; Bagga & D'Antonio (2013)* |
| miR-124 binding site | Visvanathan et al. (2007); Jovicic et al. (2013) |

TGCGCGCTCGCTCGCTCACTGAGGCCGCCCGGGCAAAGCCCGGGCGTCGGGCGACCTTTGGTCGCCCGGCCTCAGTGAGCGAGCGA
GCGCGCAGAGAGGGAGTGGGGTTCGGTACCCATAGGCGCCAAGAGCCTAGACTTCCTTAAGCGCCAGAGTCCACAAGGGCCCAGTT
AATCCTCAACATTCAAATGCTGCCCACAAAACCAGCCCCTCTGTGCCCTAGCCGCCTCTTTTTTCCAAGTGACAGTAGAACTCCAC
CAATCCGCAGCTGAATGGGGTCCGCCTCTTTTCCCTGCCTAAACAGACAGGAACTCCTGCCAATTGAGGGCGTCACCGCTAAGGCT
CCGCCCCAGCCTGGGCTCCACAACCAATGAAGGGTAATCTCGACAAAGAGCAAGGGGTGGGGCGCGGGCGCGCAGGTGCAGCAGCA
CACAGGCTGGTCGGGAGGGCGGGGCGCGACGTCTGCCGTGCGGGGTCCCGGCATCGGTTGCGCGCGCGCTCCCTCCTCTCGGAGAG
AGGGCTGTGGTAAAACCCGTCCGGAAACCATGGCCGCCGCCGCCGCCGCCGCCGAGCGGAGGAGGAGGAGGAGGCGAGGAGGAG
AGACTGGAAGAAAAGTCAGAAGACCAGGACCTCCAGGGCCTCAAGGACAAACCCCTCAAGTTTAAAAAGGTGAAGAAAGATAAGAA
AGAAGAGAAAGAGGGCAAGCATGAGCCCGTGCAGCCATCAGCCCACCACTCTGCTGAGCCCGCAGAGGCAGGCAAAGCAGAGACAT
CAGAAGGGTCAGGCTCCGCCCCGGCTGTGCCGGAAGCTTCTGCCTCCCCCAAACAGCGGCGCTCCATCATCCGTGACCGGGGACCC
ATGTATGATGACCCCACCCTGCCTGAAGGCTGGACACGGAAGCTTAAGCAAAGGAAATCTGGCCGCTCTGCTGGGAAGTATGATGT
GTATTTGATCAATCCCCAGGGAAAAGCCTTTCGCTCTAAAGTGGAGTTGATTGCGTACTTCGAAAAGGTAGGCGACACATCCCTGG
ACCCTAATGATTTTGACTTCACGGTAACTGGGAGAGGGAGCCCCTCCCGGCGAGAGCAGAAACCACCTAAGAAGCCCAAATCTCCC
AAAGCTCCAGGAACTGGCAGAGGCCGGGGACGCCCCAAAGGGAGCGGCACCACGAGACCCAAGGCGGCCACGTCAGAGGGTGTGCA
GGTGAAAAGGGTCCTGGAGAAAAGTCCTGGGAAGCTCCTTGTCAAGATGCCTTTTCAAACTTCGCCAGGGGGCAAGGCTGAGGGGG
GTGGGGCCACCACATCCACCCAGGTCATGGTGATCAAACGCCCCGGCAGGAAGCGAAAAGCTGAGGCCGACCCTCAGGCCATTCCC
AAGAAACGGGGCCGAAAGCCGGGGAGTGTGGTGGCAGCCGCTGCCGCCGAGGCCAAAAAGAAAGCCGTGAAGGAGTCTTCTATCCG
ATCTGTGCAGGAGACCGTACTCCCCATCAAGAAGCGCAAGACCCGGGAGACGGTCAGCATCGAGGTCAAGGAAGTGGTGAAGCCCC
TGCTGGTGTCCACCCTCGGTGAGAAGAGCGGGAAAGGACTGAAGACCTGTAAGAGCCCTGGGCGGAAAAGCAAGGAGAGCAGCCCC
AAGGGGCGCAGCAGCAGCGCCTCCTCACCCCCCAAGAAGGAGCACCACCACCATCACCACCACTCAGAGTCCCCAAAGGCCCCCGT
GCCACTGCTCCCACCCCTGCCCCCACCTCCACCTGAGCCCGAGAGCTCCGAGGACCCCACCAGCCCCCCTGAGCCCCAGGACTTGA
GCAGCAGCGTCTGCAAAGAGGAGAAGATGCCCAGAGGAGGCTCACTGGAGAGCGACGGCTGCCCCAAGGAGCCAGCTAAGACTCAG
CCCGCGGTTGCCACCGCCGCCACGGCCGCAGAAAAGTACAAACACCGAGGGGAGGGAGAGCGCAAAGACATTGTTTCATCCTCCAT
GCCAAGGCCAAACAGAGAGGAGCCTGTGGACAGCCGGACGCCCGTGACCGAGAGAGTTAGCTCTAGAGGGCCCTTCGAACAAAAAC
TCATCTCAGAAGAGGATCTGGTCGACTAGAGCTCGCTGATCAGCCTCACAAGAATAAAGGCAGCTGTTGTCTCTTCAGAAGTAGCT
TTGCACTTTTCTAAACTAGGAATATCACCAGGACTGTTACTCAATGTGTGGGTACCGAAAGCACTGATATATTTAAAAACAAAAGG
TGTAACCTATTTATTATATAAAGAGTTTGCCTTATAAATTTACATAAAAATGTCCGTTTGTGTCTTTTGTTGTAAAAATCACGCGT
AGGAACCCCTAGTGATGGAGTTGGCCACTCCCTCTCTGCGCGCTCGCTCGCTCACTGAGGCCGGGCGACCAAAGGTCGCCCGACGC
CCGGGCTTTGCCCGGGCGGCCTCAGTGAGCGAGCGAGCGCGCAGCTGGCGTAATAGCGAAGAGGCCCGCACCGATCGCCCTTCCCA
ACAGTTGCGCAGCCTGAATGGCGAATGGCGATTCCGTTGCAATGGCTGGCGGTAATATTGTTCTGGATATTACCAGCAAGGCCGAT
AGTTTGAGTTCTTCTACTCAGGCAAGTGATGTTATTACTAATCAAAGAAGTATTGCGACAACGGTTAATTTGCGTGATGGACAGAC
TCTTTTACTCGGTGGCCTCACTGATTATAAAAACACTTCTCAGGATTCTGGCGTACCGTTCCTGTCTAAAATCCCTTTAATCGGCC
TCCTGTTTAGCTCCCGCTCTGATTCTAACGAGGAAAGCACGTTATACGTGCTCGTCAAAGCAACCATAGTACGCGCCCTGTAGCGG
CGCATTAAGCGCGGCGGGTGTGGTGGTTACGCGCAGCGTGACCGCTACACTTGCCAGCGCCCTAGCGCCCGCTCCTTTCGCTTTCT
TCCCTTCCTTTCTCGCCACGTTCGCCGGCTTTCCCCGTCAAGCTCTAAATCGGGGGCTCCCTTTAGGGTTCCGATTTAGTGCTTTA
CGGCACCTCGACCCCAAAAAACTTGATTAGGGTGATGGTTCACGTAGTGGGCCATCGCCCTGATAGACGGTTTTTCGCCCTTTGAC
GTTGGAGTCCACGTTCTTTAATAGTGGACTCTTGTTCCAAACTGGAACAACACTCAACCCTATCTCGGTCTATTCTTTTGATTTAT
AAGGGATTTTGCCGATTTCGGCCTATTGGTTAAAAAATGAGCTGATTTAACAAAAATTTAACGCGAATTTTAACAAAATATTAACG
CTTACAATTTAAATATTTGCTTATACAATCTTCCTGTTTTTGGGGCTTTTCTGATTATCAACCGGGGTACATATGATTGACATGCT
AGTTTTACGATTACCGTTCATCGATTCTCTTGTTTGCTCCAGACTCTCAGGCAATGACCTGATAGCCTTTGTAGAGACCTCTCAAA
AATAGCTACCCTCTCCGGCATGAATTTATCAGCTAGAACGGTTGAATATCATATTGATGGTGATTTGACTGTCTCCGGCCTTTCTC
ACCCGTTTGAATCTTTACCTACACATTACTCAGGCATTGCATTTAAAATATATGAGGGTTCTAAAAATTTTTATCCTTGCGTTGAA
ATAAAGGCTTCTCCCGCAAAAGTATTACAGGGTCATAATGTTTTTGGTACAACCGATTTAGCTTTATGCTCTGAGGCTTTATTGCT
TAATTTTGCTAATTCTTTGCCTTGCCTGTATGATTTATTGGATGTTGGAATTCCTGATGCGGTATTTTCTCCTTACGCATCTGTGC
GGTATTTCACACCGCATATGGTGCACTCTCAGTACAATCTGCTCTGATGCCGCATAGTTAAGCCAGCCCCGACACCCGCCAACACC
CGCTGACGCGCCCTGACGGGCTTGTCTGCTCCCGGCATCCGCTTACAGACAAGCTGTGACCGTCTCCGGGAGCTGCATGTGTCAGA
GGTTTTCACCGTCATCACCGAAACGCGCGAGACGAAAGGGCCTCGTGATACGCCTATTTTTATAGGTTAATGTCATGATAATAATG
GTTTCTTAGACGTCAGGTGGCACTTTTCGGGGAAATGTGCGCGGAACCCCTATTTGTTTATTTTTCTAAATACATTCAAATATGTA
TCCGCTCATGAGACAATAACCCTGATAAATGCTTCAATAATATTGAAAAAGGAAGAGTATGAGTATTCAACATTTCCGTGTCGCCC
TTATTCCCTTTTTTGCGGCATTTTGCCTTCCTGTTTTTGCTCACCCAGAAACGCTGGTGAAAGTAAAAGATGCTGAAGATCAGTTG
GGTGCACGAGTGGGTTACATCGAACTGGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGAGCAACTCGGTCGCCGCATACACTATT
CTCAGAATGACTTGGTTGAGTACTCACCAGTCACAGAAAAGCATCTTACGGATGGCATGACAGTAAGAGAATTATGCAGTGCTGCC

Figure 16

```
ATAACCATGAGTGATAACACTGCGGCCAACTTACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCATACCAAACGACGAGCGTGACACCACGATGCCTG
TAGCAATGGCAACAACGTTGCGCAAACTATTAACTGGCGAACTACTTACTCTAGCTTCCCGGCAACAATTAATAGACTGGATGGAG
GCGGATAAAGTTGCAGGACCACTTCTGCGCTCGGCCCTTCCGGCTGGCTGGTTTATTGCTGATAAATCTGGAGCCGGTGAGCGTGG
GTCTCGCGGTATCATTGCAGCACTGGGGCCAGATGGTAAGCCCTCCCGTATCGTAGTTATCTACACGACGGGGAGTCAGGCAACTA
TGGATGAACGAAATAGACAGATCGCTGAGATAGGTGCCTCACTGATTAAGCATTGGTAACTGTCAGACCAAGTTTACTCATATATA
CTTTAGATTGATTTAAAACTTCATTTTTAATTTAAAAGGATCTAGGTGAAGATCCTTTTTGATAATCTCATGACCAAAATCCCTTA
ACGTGAGTTTTCGTTCCACTGAGCGTCAGACCCCGTAGAAAAGATCAAAGGATCTTCTTGAGATCCTTTTTTTCTGCGCGTAATCT
GCTGCTTGCAAACAAAAAAACCACCGCTACCAGCGGTGGTTTGTTTGCCGGATCAAGAGCTACCAACTCTTTTTCCGAAGGTAACT
GGCTTCAGCAGAGCGCAGATACCAAATACTGTCCTTCTAGTGTAGCCGTAGTTAGGCCACCACTTCAAGAACTCTGTAGCACCGCC
TACATACCTCGCTCTGCTAATCCTGTTACCAGTGGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACAGCCCAGCTTGGAGCGAACGACCTACACCGAACTG
AGATACCTACAGCGTGAGCTATGAGAAAGCGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCCTGTCGGGTTTCGCCACCTCTGACTTGAGC
GTCGATTTTTGTGATGCTCGTCAGGGGGCGGAGCCTATGGAAAAACGCCAGCAACGCGGCCTTTTTACGGTTCCTGGCCTTTTGC
TGGCCTTTTGCTCACATGTTCTTTCCTGCGTTATCCCCTGATTCTGTGGATAACCGTATTACCGCCTTTGAGTGAGCTGATACCGC
TCGCCGCAGCCGAACGACCGAGCGCAGCGAGTCAGTGAGCGAGGAAGCGGAAGAGCGCCCAATACGCAAACCGCCTCTCCCCGCGC
GTTGGCCGATTCATTAATGCAGC
```

Figure 16 (continued)

SEQUENCE LISTING

<160> NUMBER OF SEQ ID NOS: 34

<210> SEQ ID NO 1
<211> LENGTH: 104
<212> TYPE: DNA
<213> ORGANISM: Artificial Sequence
<220> FEATURE:
<223> OTHER INFORMATION: scAAV vector containing AAV-2 ITR

<400> SEQUENCE: 1

```
gcgcgctcgc tcgctcactg aggccgcccg ggcaaagccc gggcgtcggg cgacctttgg      60
tcgcccggcc tcagtgagcg agcgagcgcg cagagaggga gtgg                     104
```

<210> SEQ ID NO 2
<211> LENGTH: 104
<212> TYPE: DNA
<213> ORGANISM: Artificial Sequence
<220> FEATURE:
<223> OTHER INFORMATION: scAAV vector containing AVV-2 ITRs

<400> SEQUENCE: 2

```
ccactccctc tctgcgcgct cgctcgctca ctgaggccgg gcgaccaaag gtcgcccgac      60
gcccgggctt tgcccgggcg gcctcagtga gcgagcgagc gcgc                     104
```

<210> SEQ ID NO 3
<211> LENGTH: 499
<212> TYPE: PRT
<213> ORGANISM: Artificial Sequence
<220> FEATURE:
<223> OTHER INFORMATION: Human MeCP2 protein isoform 1

<400> SEQUENCE: 3

```
Met Ala Ala Ala Ala Ala Ala Pro Ser Gly Gly Gly Gly Gly
1               5                   10                  15
Glu Glu Glu Arg Leu Glu Glu Lys Ser Glu Asp Gln Asp Leu Gln Gly
                20                  25                  30
Leu Lys Asp Lys Pro Leu Lys Phe Lys Lys Val Lys Lys Asp Lys Lys
            35                  40                  45
Glu Glu Lys Glu Gly Lys His Glu Pro Val Gln Pro Ser Ala His His
        50                  55                  60
Ser Ala Glu Pro Ala Glu Ala Gly Lys Ala Glu Thr Ser Glu Gly Ser
65                  70                  75                  80
Gly Ser Ala Pro Ala Val Pro Glu Ala Ser Ala Ser Pro Lys Gln Arg
                85                  90                  95
Arg Ser Ile Ile Arg Asp Arg Gly Pro Met Tyr Asp Asp Pro Thr Leu
            100                 105                 110
Pro Glu Gly Trp Thr Arg Lys Leu Lys Gln Arg Lys Ser Gly Arg Ser
        115                 120                 125
Ala Gly Lys Tyr Asp Val Tyr Leu Ile Asn Pro Gln Gly Lys Ala Phe
    130                 135                 140
Arg Ser Lys Val Glu Leu Ile Ala Tyr Phe Glu Lys Val Gly Asp Thr
145                 150                 155                 160
Ser Leu Asp Pro Asn Asp Phe Asp Phe Thr Val Thr Gly Arg Gly Ser
                165                 170                 175
Pro Ser Arg Arg Glu Gln Lys Pro Pro Lys Lys Pro Lys Ser Pro Lys
            180                 185                 190
Ala Pro Gly Thr Gly Arg Gly Arg Gly Arg Pro Lys Gly Ser Gly Thr
        195                 200                 205
Thr Arg Pro Lys Ala Ala Thr Ser Glu Gly Val Gln Val Lys Arg Val
    210                 215                 220
Leu Glu Lys Ser Pro Gly Lys Leu Leu Val Lys Met Pro Phe Gln Thr
225                 230                 235                 240
Ser Pro Gly Gly Lys Ala Glu Gly Gly Ala Thr Thr Ser Thr Gln
                245                 250                 255
Val Met Val Ile Lys Arg Pro Gly Arg Lys Arg Lys Ala Glu Ala Asp
            260                 265                 270
Pro Gln Ala Ile Pro Lys Lys Arg Gly Arg Lys Pro Gly Ser Val Val
        275                 280                 285
Ala Ala Ala Ala Ala Glu Ala Lys Lys Lys Ala Val Lys Glu Ser Ser
    290                 295                 300
Ile Arg Ser Val Gln Glu Thr Val Leu Pro Ile Lys Lys Arg Lys Thr
305                 310                 315                 320
Arg Glu Thr Val Ser Ile Glu Val Lys Glu Val Lys Pro Leu Leu
                325                 330                 335
Val Ser Thr Leu Gly Glu Lys Ser Gly Lys Gly Leu Lys Thr Cys Lys
            340                 345                 350
Ser Pro Gly Arg Lys Ser Lys Glu Ser Ser Pro Lys Gly Arg Ser Ser
        355                 360                 365
Ser Ala Ser Ser Pro Pro Lys Lys Glu His His His His His His
    370                 375                 380
Ser Glu Ser Pro Lys Ala Pro Val Pro Leu Leu Pro Pro Leu Pro Pro
385                 390                 395                 400
Pro Pro Pro Glu Pro Glu Ser Ser Glu Asp Pro Thr Ser Pro Pro Glu
                405                 410                 415
```

```
Pro Gln Asp Leu Ser Ser Val Cys Lys Glu Lys Met Pro Arg
            420                 425                 430

Gly Gly Ser Leu Glu Ser Asp Gly Cys Pro Lys Glu Pro Ala Lys Thr
        435                 440                 445

Gln Pro Ala Val Ala Thr Ala Ala Thr Ala Ala Glu Lys Tyr Lys His
450                 455                 460

Arg Gly Glu Gly Glu Arg Lys Asp Ile Val Ser Ser Ser Met Pro Arg
465                 470                 475                 480

Pro Asn Arg Glu Glu Pro Val Asp Ser Arg Thr Pro Val Thr Glu Arg
                485                 490                 495

Val Ser Ser

<210> SEQ ID NO 4
<211> LENGTH: 487
<212> TYPE: PRT
<213> ORGANISM: Artificial Sequence
<220> FEATURE:
<223> OTHER INFORMATION: Human MeCP2 protein isoform 2

<400> SEQUENCE: 4

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
            20                  25                  30

Lys Asp Lys Lys Glu Glu Lys Glu Gly Lys His Glu Pro Val Gln Pro
        35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
    210                 215                 220

Pro Phe Gln Thr Ser Pro Gly Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270
```

```
Gly Ser Val Val Ala Ala Ala Ala Glu Ala Lys Lys Lys Ala Val
            275                 280                 285
Lys Glu Ser Ser Ile Arg Ser Val Gln Glu Thr Val Leu Pro Ile Lys
290                 295                 300
Lys Arg Lys Thr Arg Glu Thr Val Ser Ile Glu Val Lys Glu Val Val
305                 310                 315                 320
Lys Pro Leu Leu Val Ser Thr Leu Gly Glu Lys Ser Gly Lys Gly Leu
                325                 330                 335
Lys Thr Cys Lys Ser Pro Gly Arg Lys Ser Lys Glu Ser Ser Pro Lys
            340                 345                 350
Gly Arg Ser Ser Ala Ser Ser Pro Pro Lys Lys Glu His His His
        355                 360                 365
His His His His Ser Glu Ser Pro Lys Ala Pro Val Pro Leu Leu Pro
    370                 375                 380
Pro Leu Pro Pro Pro Pro Glu Pro Glu Ser Ser Glu Asp Pro Thr
385                 390                 395                 400
Ser Pro Pro Glu Pro Gln Asp Leu Ser Ser Val Cys Lys Glu Glu
                405                 410                 415
Lys Met Pro Arg Gly Gly Ser Leu Glu Ser Asp Gly Cys Pro Lys Glu
            420                 425                 430
Pro Ala Lys Thr Gln Pro Ala Val Ala Thr Ala Ala Thr Ala Ala Glu
        435                 440                 445
Lys Tyr Lys His Arg Gly Glu Gly Glu Arg Lys Asp Ile Val Ser Ser
    450                 455                 460
Ser Met Pro Arg Pro Asn Arg Glu Glu Pro Val Asp Ser Arg Thr Pro
465                 470                 475                 480
Val Thr Glu Arg Val Ser Ser
                485

<210> SEQ ID NO 5
<211> LENGTH: 102
<212> TYPE: PRT
<213> ORGANISM: Artificial Sequence
<220> FEATURE:
<223> OTHER INFORMATION: methyl-CpG binding domain (MBD) of human MeCP
      protein

<400> SEQUENCE: 5

Pro Ala Val Pro Glu Ala Ser Ala Ser Pro Lys Gln Arg Arg Ser Ile
1               5                   10                  15
Ile Arg Asp Arg Gly Pro Met Tyr Asp Asp Pro Thr Leu Pro Glu Gly
            20                  25                  30
Trp Thr Arg Lys Leu Lys Gln Arg Lys Ser Gly Arg Ser Ala Gly Lys
        35                  40                  45
Tyr Asp Val Tyr Leu Ile Asn Pro Gln Gly Lys Ala Phe Arg Ser Lys
    50                  55                  60
Val Glu Leu Ile Ala Tyr Phe Glu Lys Val Gly Asp Thr Ser Leu Asp
65                  70                  75                  80
Pro Asn Asp Phe Asp Phe Thr Val Thr Gly Arg Gly Ser Pro Ser Arg
                85                  90                  95
Arg Glu Gln Lys Pro Pro
            100

<210> SEQ ID NO 6
<211> LENGTH: 40
<212> TYPE: PRT
<213> ORGANISM: Artificial Sequence
```

```
<220> FEATURE:
<223> OTHER INFORMATION: NCoR/SMRT Interaction Domain (NID) of human
      MeCP2

<400> SEQUENCE: 6

Pro Gly Ser Val Val Ala Ala Ala Ala Glu Ala Lys Lys Ala Val
1               5                   10                  15

Lys Glu Ser Ser Ile Arg Ser Val Gln Glu Thr Val Leu Pro Ile Lys
            20                  25                  30

Lys Arg Lys Thr Arg Glu Thr Val
            35                  40

<210> SEQ ID NO 7
<211> LENGTH: 17
<212> TYPE: PRT
<213> ORGANISM: Artificial Sequence
<220> FEATURE:
<223> OTHER INFORMATION: native MeCP2 NLS

<400> SEQUENCE: 7

Arg Lys Ala Glu Ala Asp Pro Gln Ala Ile Pro Lys Lys Arg Gly Arg
1               5                   10                  15

Lys

<210> SEQ ID NO 8
<211> LENGTH: 7
<212> TYPE: PRT
<213> ORGANISM: Artificial Sequence
<220> FEATURE:
<223> OTHER INFORMATION: SV40 Large T antigen NLS

<400> SEQUENCE: 8

Pro Lys Lys Lys Arg Lys Val
1               5

<210> SEQ ID NO 9
<211> LENGTH: 475
<212> TYPE: PRT
<213> ORGANISM: Artificial Sequence
<220> FEATURE:
<223> OTHER INFORMATION: MeCP2

<400> SEQUENCE: 9

Ser Glu Asp Gln Asp Leu Gln Gly Leu Lys Asp Lys Pro Leu Lys Phe
1               5                   10                  15

Lys Lys Val Lys Lys Asp Lys Lys Glu Glu Lys Glu Gly Lys His Glu
            20                  25                  30

Pro Val Gln Pro Ser Ala His His Ser Ala Glu Pro Ala Glu Ala Gly
        35                  40                  45

Lys Ala Glu Thr Ser Glu Gly Ser Gly Ser Ala Pro Ala Val Pro Glu
    50                  55                  60

Ala Ser Ala Ser Pro Lys Gln Arg Arg Ser Ile Ile Arg Asp Arg Gly
65                  70                  75                  80

Pro Met Tyr Asp Asp Pro Thr Leu Pro Glu Gly Trp Thr Arg Lys Leu
                85                  90                  95

Lys Gln Arg Lys Ser Gly Arg Ser Ala Gly Lys Tyr Asp Val Tyr Leu
            100                 105                 110

Ile Asn Pro Gln Gly Lys Ala Phe Arg Ser Lys Val Glu Leu Ile Ala
        115                 120                 125

Tyr Phe Glu Lys Val Gly Asp Thr Ser Leu Asp Pro Asn Asp Phe Asp
    130                 135                 140
```

Phe Thr Val Thr Gly Arg Gly Ser Pro Ser Arg Arg Glu Gln Lys Pro
145                 150                 155                 160

Pro Lys Lys Pro Lys Ser Pro Lys Ala Pro Gly Thr Gly Arg Gly Arg
            165                 170                 175

Gly Arg Pro Lys Gly Ser Gly Thr Thr Arg Pro Lys Ala Ala Thr Ser
            180                 185                 190

Glu Gly Val Gln Val Lys Arg Val Leu Glu Lys Ser Pro Gly Lys Leu
            195                 200                 205

Leu Val Lys Met Pro Phe Gln Thr Ser Pro Gly Gly Lys Ala Glu Gly
        210                 215                 220

Gly Gly Ala Thr Thr Ser Thr Gln Val Met Val Ile Lys Arg Pro Gly
225                 230                 235                 240

Arg Lys Arg Lys Ala Glu Ala Asp Pro Gln Ala Ile Pro Lys Lys Arg
                245                 250                 255

Gly Arg Lys Pro Gly Ser Val Val Ala Ala Ala Ala Glu Ala Lys
            260                 265                 270

Lys Lys Ala Val Lys Glu Ser Ser Ile Arg Ser Val Gln Glu Thr Val
        275                 280                 285

Leu Pro Ile Lys Lys Arg Lys Thr Arg Glu Thr Val Ser Ile Glu Val
    290                 295                 300

Lys Glu Val Val Lys Pro Leu Leu Val Ser Thr Leu Gly Glu Lys Ser
305                 310                 315                 320

Gly Lys Gly Leu Lys Thr Cys Lys Ser Pro Gly Arg Lys Ser Lys Glu
                325                 330                 335

Ser Ser Pro Lys Gly Arg Ser Ser Ser Ala Ser Ser Pro Pro Lys Lys
            340                 345                 350

Glu His His His His His His Ser Glu Ser Pro Lys Ala Pro Val
        355                 360                 365

Pro Leu Leu Pro Pro Leu Pro Pro Pro Pro Glu Pro Glu Ser Ser
370                 375                 380

Glu Asp Pro Thr Ser Pro Glu Pro Gln Asp Leu Ser Ser Ser Val
385                 390                 395                 400

Cys Lys Glu Glu Lys Met Pro Arg Gly Gly Ser Leu Glu Ser Asp Gly
                405                 410                 415

Cys Pro Lys Glu Pro Ala Lys Thr Gln Pro Ala Val Ala Thr Ala Ala
            420                 425                 430

Thr Ala Ala Glu Lys Tyr Lys His Arg Gly Glu Gly Glu Arg Lys Asp
            435                 440                 445

Ile Val Ser Ser Ser Met Pro Arg Pro Asn Arg Glu Glu Pro Val Asp
        450                 455                 460

Ser Arg Thr Pro Val Thr Glu Arg Val Ser Ser
465                 470                 475

<210> SEQ ID NO 10
<211> LENGTH: 241
<212> TYPE: PRT
<213> ORGANISM: Artificial Sequence
<220> FEATURE:
<223> OTHER INFORMATION: MeCP2 fragment designated Delta NC

<400> SEQUENCE: 10

Pro Ala Val Pro Glu Ala Ser Ala Ser Pro Lys Gln Arg Arg Ser Ile
1               5                   10                  15

Ile Arg Asp Arg Gly Pro Met Tyr Asp Asp Pro Thr Leu Pro Glu Gly
            20                  25                  30

```
Trp Thr Arg Lys Leu Lys Gln Arg Lys Ser Gly Arg Ser Ala Gly Lys
        35                  40                  45

Tyr Asp Val Tyr Leu Ile Asn Pro Gln Gly Lys Ala Phe Arg Ser Lys
 50                  55                  60

Val Glu Leu Ile Ala Tyr Phe Glu Lys Val Gly Asp Thr Ser Leu Asp
 65                  70                  75                  80

Pro Asn Asp Phe Asp Phe Thr Val Thr Gly Arg Gly Ser Pro Ser Arg
                 85                  90                  95

Arg Glu Gln Lys Pro Pro Lys Lys Pro Lys Ser Pro Lys Ala Pro Gly
                100                 105                 110

Thr Gly Arg Gly Arg Gly Arg Pro Lys Gly Ser Gly Thr Thr Arg Pro
                115                 120                 125

Lys Ala Ala Thr Ser Glu Gly Val Gln Val Lys Arg Val Leu Glu Lys
            130                 135                 140

Ser Pro Gly Lys Leu Leu Val Lys Met Pro Phe Gln Thr Ser Pro Gly
145                 150                 155                 160

Gly Lys Ala Glu Gly Gly Ala Thr Thr Ser Thr Gln Val Met Val
                165                 170                 175

Ile Lys Arg Pro Gly Arg Lys Arg Lys Ala Glu Ala Asp Pro Gln Ala
            180                 185                 190

Ile Pro Lys Lys Arg Gly Arg Lys Pro Gly Ser Val Val Ala Ala Ala
            195                 200                 205

Ala Ala Glu Ala Lys Lys Lys Ala Val Lys Glu Ser Ser Ile Arg Ser
        210                 215                 220

Val Gln Glu Thr Val Leu Pro Ile Lys Lys Arg Lys Thr Arg Glu Thr
225                 230                 235                 240

Val

<210> SEQ ID NO 11
<211> LENGTH: 157
<212> TYPE: PRT
<213> ORGANISM: Artificial Sequence
<220> FEATURE:
<223> OTHER INFORMATION: Protein variant designated Delta NIC

<400> SEQUENCE: 11

Pro Ala Val Pro Glu Ala Ser Ala Ser Pro Lys Gln Arg Arg Ser Ile
1               5                   10                  15

Ile Arg Asp Arg Gly Pro Met Tyr Asp Asp Pro Thr Leu Pro Glu Gly
                20                  25                  30

Trp Thr Arg Lys Leu Lys Gln Arg Lys Ser Gly Arg Ser Ala Gly Lys
        35                  40                  45

Tyr Asp Val Tyr Leu Ile Asn Pro Gln Gly Lys Ala Phe Arg Ser Lys
 50                  55                  60

Val Glu Leu Ile Ala Tyr Phe Glu Lys Val Gly Asp Thr Ser Leu Asp
 65                  70                  75                  80

Pro Asn Asp Phe Asp Phe Thr Val Thr Gly Arg Gly Ser Pro Ser Arg
                 85                  90                  95

Arg Glu Gln Lys Pro Pro Gly Ser Ser Gly Ser Ser Gly Pro Lys Lys
                100                 105                 110

Lys Arg Lys Val Pro Gly Ser Val Val Ala Ala Ala Ala Glu Ala
            115                 120                 125

Lys Lys Lys Ala Val Lys Glu Ser Ser Ile Arg Ser Val Gln Glu Thr
130                 135                 140
```

```
Val Leu Pro Ile Lys Lys Arg Lys Thr Arg Glu Thr Val
145                 150                 155
```

```
<210> SEQ ID NO 12
<211> LENGTH: 24
<212> TYPE: PRT
<213> ORGANISM: Artificial Sequence
<220> FEATURE:
<223> OTHER INFORMATION: N-terminal portion

<400> SEQUENCE: 12
```

```
Met Ala Ala Ala Ala Ala Ala Pro Ser Gly Gly Gly Gly Gly Gly
1               5                   10                  15

Glu Glu Glu Arg Leu Glu Glu Lys
            20
```

```
<210> SEQ ID NO 13
<211> LENGTH: 12
<212> TYPE: PRT
<213> ORGANISM: Artificial Sequence
<220> FEATURE:
<223> OTHER INFORMATION: N-terminal portion

<400> SEQUENCE: 13
```

```
Met Val Ala Gly Met Leu Gly Leu Arg Glu Glu Lys
1               5                   10
```

```
<210> SEQ ID NO 14
<211> LENGTH: 499
<212> TYPE: PRT
<213> ORGANISM: Artificial Sequence
<220> FEATURE:
<223> OTHER INFORMATION: MeCP2 protein encoded by the expression
      cassette, human isoform 1

<400> SEQUENCE: 14
```

```
Met Ala Ala Ala Ala Ala Ala Pro Ser Gly Gly Gly Gly Gly Gly
1               5                   10                  15

Glu Glu Glu Arg Leu Glu Glu Lys Ser Glu Asp Gln Asp Leu Gln Gly
            20                  25                  30

Leu Lys Asp Lys Pro Leu Lys Phe Lys Lys Val Lys Lys Asp Lys Lys
        35                  40                  45

Glu Glu Lys Glu Gly Lys His Glu Pro Val Gln Pro Ser Ala His His
    50                  55                  60

Ser Ala Glu Pro Ala Glu Ala Gly Lys Ala Glu Thr Ser Glu Gly Ser
65                  70                  75                  80

Gly Ser Ala Pro Ala Val Pro Glu Ala Ser Ala Ser Pro Lys Gln Arg
                85                  90                  95

Arg Ser Ile Ile Arg Asp Arg Gly Pro Met Tyr Asp Asp Pro Thr Leu
            100                 105                 110

Pro Glu Gly Trp Thr Arg Lys Leu Lys Gln Arg Lys Ser Gly Arg Ser
        115                 120                 125

Ala Gly Lys Tyr Asp Val Tyr Leu Ile Asn Pro Gln Gly Lys Ala Phe
    130                 135                 140

Arg Ser Lys Val Glu Leu Ile Ala Tyr Phe Glu Lys Val Gly Asp Thr
145                 150                 155                 160

Ser Leu Asp Pro Asn Asp Phe Asp Phe Thr Val Thr Gly Arg Gly Ser
                165                 170                 175

Pro Ser Arg Arg Glu Gln Lys Pro Pro Lys Pro Lys Ser Pro Lys
            180                 185                 190
```

```
Ala Pro Gly Thr Gly Arg Gly Arg Gly Arg Pro Lys Gly Ser Gly Thr
            195                 200                 205

Thr Arg Pro Lys Ala Ala Thr Ser Glu Gly Val Gln Val Lys Arg Val
210                 215                 220

Leu Glu Lys Ser Pro Gly Lys Leu Leu Val Lys Met Pro Phe Gln Thr
225                 230                 235                 240

Ser Pro Gly Gly Lys Ala Glu Gly Gly Ala Thr Thr Ser Thr Thr Gln
                245                 250                 255

Val Met Val Ile Lys Arg Pro Gly Arg Lys Arg Lys Ala Glu Ala Asp
            260                 265                 270

Pro Gln Ala Ile Pro Lys Lys Arg Gly Arg Lys Pro Gly Ser Val Val
            275                 280                 285

Ala Ala Ala Ala Ala Glu Ala Lys Lys Ala Val Lys Glu Ser Ser
            290                 295                 300

Ile Arg Ser Val Gln Glu Thr Val Leu Pro Ile Lys Lys Arg Lys Thr
305                 310                 315                 320

Arg Glu Thr Val Ser Ile Glu Val Lys Glu Val Val Lys Pro Leu Leu
                325                 330                 335

Val Ser Thr Leu Gly Glu Lys Ser Gly Lys Gly Leu Lys Thr Cys Lys
            340                 345                 350

Ser Pro Gly Arg Lys Ser Lys Glu Ser Ser Pro Lys Gly Arg Ser Ser
            355                 360                 365

Ser Ala Ser Ser Pro Pro Lys Lys Glu His His His His His His
            370                 375                 380

Ser Glu Ser Pro Lys Ala Pro Val Pro Leu Leu Pro Pro Leu Pro Pro
385                 390                 395                 400

Pro Pro Pro Glu Pro Glu Ser Ser Glu Asp Pro Thr Ser Pro Pro Glu
                405                 410                 415

Pro Gln Asp Leu Ser Ser Ser Val Cys Lys Glu Lys Met Pro Arg
            420                 425                 430

Gly Gly Ser Leu Glu Ser Asp Gly Cys Pro Lys Glu Pro Ala Lys Thr
            435                 440                 445

Gln Pro Ala Val Ala Thr Ala Ala Thr Ala Ala Glu Lys Tyr Lys His
450                 455                 460

Arg Gly Glu Gly Glu Arg Lys Asp Ile Val Ser Ser Met Pro Arg
465                 470                 475                 480

Pro Asn Arg Glu Glu Pro Val Asp Ser Arg Thr Pro Val Thr Glu Arg
                485                 490                 495

Val Ser Ser

<210> SEQ ID NO 15
<211> LENGTH: 487
<212> TYPE: PRT
<213> ORGANISM: Artificial Sequence
<220> FEATURE:
<223> OTHER INFORMATION: MeCP2 protein encoded by the expression
      cassette, human isoform 2

<400> SEQUENCE: 15

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
                20                  25                  30

Lys Asp Lys Lys Glu Glu Lys Glu Gly Lys His Glu Pro Val Gln Pro
            35                  40                  45
```

-continued

```
Ser Ala His His Ser Ala Glu Pro Ala Glu Ala Gly Lys Ala Glu Thr
 50                  55                  60
Ser Glu Gly Ser Gly Ser Ala Pro Ala Val Pro Glu Ala Ser Ala Ser
 65                  70                  75                  80
Pro Lys Gln Arg Arg Ser Ile Ile Arg Asp Arg Gly Pro Met Tyr Asp
                 85                  90                  95
Asp Pro Thr Leu Pro Glu Gly Trp Thr Arg Lys Leu Lys Gln Arg Lys
            100                 105                 110
Ser Gly Arg Ser Ala Gly Lys Tyr Asp Val Tyr Leu Ile Asn Pro Gln
            115                 120                 125
Gly Lys Ala Phe Arg Ser Lys Val Glu Leu Ile Ala Tyr Phe Glu Lys
130                 135                 140
Val Gly Asp Thr Ser Leu Asp Pro Asn Asp Phe Asp Phe Thr Val Thr
145                 150                 155                 160
Gly Arg Gly Ser Pro Ser Arg Arg Glu Gln Lys Pro Pro Lys Lys Pro
                165                 170                 175
Lys Ser Pro Lys Ala Pro Gly Thr Gly Arg Gly Arg Gly Arg Pro Lys
            180                 185                 190
Gly Ser Gly Thr Thr Arg Pro Lys Ala Ala Thr Ser Glu Gly Val Gln
            195                 200                 205
Val Lys Arg Val Leu Glu Lys Ser Pro Gly Lys Leu Leu Val Lys Met
210                 215                 220
Pro Phe Gln Thr Ser Pro Gly Gly Lys Ala Glu Gly Gly Ala Thr
225                 230                 235                 240
Thr Ser Thr Gln Val Met Val Ile Lys Arg Pro Gly Arg Lys Arg Lys
                245                 250                 255
Ala Glu Ala Asp Pro Gln Ala Ile Pro Lys Lys Arg Gly Arg Lys Pro
            260                 265                 270
Gly Ser Val Val Ala Ala Ala Ala Glu Ala Lys Lys Lys Ala Val
            275                 280                 285
Lys Glu Ser Ser Ile Arg Ser Val Gln Glu Thr Val Leu Pro Ile Lys
290                 295                 300
Lys Arg Lys Thr Arg Glu Thr Val Ser Ile Glu Val Lys Glu Val Val
305                 310                 315                 320
Lys Pro Leu Leu Val Ser Thr Leu Gly Glu Lys Ser Gly Lys Gly Leu
                325                 330                 335
Lys Thr Cys Lys Ser Pro Gly Arg Lys Ser Lys Glu Ser Ser Pro Lys
            340                 345                 350
Gly Arg Ser Ser Ala Ser Ser Pro Pro Lys Lys Glu His His His
            355                 360                 365
His His His Ser Glu Ser Pro Lys Ala Pro Val Pro Leu Leu Pro
            370                 375                 380
Pro Leu Pro Pro Pro Pro Glu Pro Glu Ser Ser Glu Asp Pro Thr
385                 390                 395                 400
Ser Pro Pro Glu Pro Gln Asp Leu Ser Ser Val Cys Lys Glu Glu
                405                 410                 415
Lys Met Pro Arg Gly Gly Ser Leu Glu Ser Asp Gly Cys Pro Lys Glu
            420                 425                 430
Pro Ala Lys Thr Gln Pro Ala Val Ala Thr Ala Ala Thr Ala Ala Glu
            435                 440                 445
Lys Tyr Lys His Arg Gly Glu Gly Glu Arg Lys Asp Ile Val Ser Ser
450                 455                 460
Ser Met Pro Arg Pro Asn Arg Glu Glu Pro Val Asp Ser Arg Thr Pro
```

```
                465                 470                 475                 480

Val Thr Glu Arg Val Ser Ser
                485

<210> SEQ ID NO 16
<211> LENGTH: 265
<212> TYPE: PRT
<213> ORGANISM: Artificial Sequence
<220> FEATURE:
<223> OTHER INFORMATION: MeCP2 protein encoded by the expression
      cassette Delta NC isoform 1

<400> SEQUENCE: 16

Met Ala Ala Ala Ala Ala Ala Pro Ser Gly Gly Gly Gly Gly Gly Gly
1               5                   10                  15

Glu Glu Glu Arg Leu Glu Glu Lys Pro Ala Val Pro Glu Ala Ser Ala
            20                  25                  30

Ser Pro Lys Gln Arg Arg Ser Ile Ile Arg Asp Arg Gly Pro Met Tyr
        35                  40                  45

Asp Asp Pro Thr Leu Pro Glu Gly Trp Thr Arg Lys Leu Lys Gln Arg
    50                  55                  60

Lys Ser Gly Arg Ser Ala Gly Lys Tyr Asp Val Tyr Leu Ile Asn Pro
65                  70                  75                  80

Gln Gly Lys Ala Phe Arg Ser Lys Val Glu Leu Ile Ala Tyr Phe Glu
                85                  90                  95

Lys Val Gly Asp Thr Ser Leu Asp Pro Asn Asp Phe Asp Phe Thr Val
            100                 105                 110

Thr Gly Arg Gly Ser Pro Ser Arg Arg Glu Gln Lys Pro Pro Lys Lys
        115                 120                 125

Pro Lys Ser Pro Lys Ala Pro Gly Thr Gly Arg Gly Arg Gly Arg Pro
    130                 135                 140

Lys Gly Ser Gly Thr Thr Arg Pro Lys Ala Ala Thr Ser Glu Gly Val
145                 150                 155                 160

Gln Val Lys Arg Val Leu Glu Lys Ser Pro Gly Lys Leu Leu Val Lys
                165                 170                 175

Met Pro Phe Gln Thr Ser Pro Gly Gly Lys Ala Glu Gly Gly Gly Ala
            180                 185                 190

Thr Thr Ser Thr Gln Val Met Val Ile Lys Arg Pro Gly Arg Lys Arg
        195                 200                 205

Lys Ala Glu Ala Asp Pro Gln Ala Ile Pro Lys Lys Arg Gly Arg Lys
    210                 215                 220

Pro Gly Ser Val Val Ala Ala Ala Ala Glu Ala Lys Lys Lys Ala
225                 230                 235                 240

Val Lys Glu Ser Ser Ile Arg Ser Val Gln Glu Thr Val Leu Pro Ile
                245                 250                 255

Lys Lys Arg Lys Thr Arg Glu Thr Val
            260                 265

<210> SEQ ID NO 17
<211> LENGTH: 253
<212> TYPE: PRT
<213> ORGANISM: Artificial Sequence
<220> FEATURE:
<223> OTHER INFORMATION: MeCP2 protein encoded by the expression
      cassette  Delta NC isoform 2

<400> SEQUENCE: 17

Met Val Ala Gly Met Leu Gly Leu Arg Glu Glu Lys Pro Ala Val Pro
```

```
            1               5                   10                  15
        Glu Ala Ser Ala Ser Pro Lys Gln Arg Arg Ser Ile Ile Arg Asp Arg
                        20                  25                  30

Gly Pro Met Tyr Asp Asp Pro Thr Leu Pro Glu Gly Trp Thr Arg Lys
                    35                  40                  45

Leu Lys Gln Arg Lys Ser Gly Arg Ser Ala Gly Lys Tyr Asp Val Tyr
            50                  55                  60

Leu Ile Asn Pro Gln Gly Lys Ala Phe Arg Ser Lys Val Glu Leu Ile
        65                  70                  75                  80

Ala Tyr Phe Glu Lys Val Gly Asp Thr Ser Leu Asp Pro Asn Asp Phe
                        85                  90                  95

Asp Phe Thr Val Thr Gly Arg Gly Ser Pro Ser Arg Arg Glu Gln Lys
                    100                 105                 110

Pro Pro Lys Lys Pro Lys Ser Pro Lys Ala Pro Gly Thr Gly Arg Gly
                    115                 120                 125

Arg Gly Arg Pro Lys Gly Ser Gly Thr Thr Arg Pro Lys Ala Ala Thr
                    130                 135                 140

Ser Glu Gly Val Gln Val Lys Arg Val Leu Glu Lys Ser Pro Gly Lys
        145                 150                 155                 160

Leu Leu Val Lys Met Pro Phe Gln Thr Ser Pro Gly Gly Lys Ala Glu
                        165                 170                 175

Gly Gly Gly Ala Thr Thr Ser Thr Gln Val Met Val Ile Lys Arg Pro
                    180                 185                 190

Gly Arg Lys Arg Lys Ala Glu Ala Asp Pro Gln Ala Ile Pro Lys Lys
                    195                 200                 205

Arg Gly Arg Lys Pro Gly Ser Val Val Ala Ala Ala Ala Glu Ala
                    210                 215                 220

Lys Lys Lys Ala Val Lys Glu Ser Ser Ile Arg Ser Val Gln Glu Thr
        225                 230                 235                 240

Val Leu Pro Ile Lys Lys Arg Lys Thr Arg Glu Thr Val
                        245                 250

<210> SEQ ID NO 18
<211> LENGTH: 181
<212> TYPE: PRT
<213> ORGANISM: Artificial Sequence
<220> FEATURE:
<223> OTHER INFORMATION: MeCP2 protein encoded by the expression
      cassette, Delta NIC isoform 1

<400> SEQUENCE: 18

Met Ala Ala Ala Ala Ala Ala Pro Ser Gly Gly Gly Gly Gly Gly Gly
        1               5                   10                  15

Glu Glu Glu Arg Leu Glu Glu Lys Pro Ala Val Pro Glu Ala Ser Ala
                        20                  25                  30

Ser Pro Lys Gln Arg Arg Ser Ile Ile Arg Asp Arg Gly Pro Met Tyr
                    35                  40                  45

Asp Asp Pro Thr Leu Pro Glu Gly Trp Thr Arg Lys Leu Lys Gln Arg
                50                  55                  60

Lys Ser Gly Arg Ser Ala Gly Lys Tyr Asp Val Tyr Leu Ile Asn Pro
        65                  70                  75                  80

Gln Gly Lys Ala Phe Arg Ser Lys Val Glu Leu Ile Ala Tyr Phe Glu
                        85                  90                  95

Lys Val Gly Asp Thr Ser Leu Asp Pro Asn Asp Phe Asp Phe Thr Val
                    100                 105                 110
```

Thr Gly Arg Gly Ser Pro Ser Arg Arg Glu Gln Lys Pro Gly Ser
            115                 120                 125

Ser Gly Ser Ser Gly Pro Lys Lys Arg Lys Val Pro Gly Ser Val
    130                 135                 140

Val Ala Ala Ala Ala Glu Ala Lys Lys Ala Val Lys Glu Ser
145                 150                 155                 160

Ser Ile Arg Ser Val Gln Glu Thr Val Leu Pro Ile Lys Arg Lys
                165                 170                 175

Thr Arg Glu Thr Val
            180

<210> SEQ ID NO 19
<211> LENGTH: 169
<212> TYPE: PRT
<213> ORGANISM: Artificial Sequence
<220> FEATURE:
<223> OTHER INFORMATION: MeCP2 protein encoded by the expression
      cassette, Delta NIC isoform 2

<400> SEQUENCE: 19

Met Val Ala Gly Met Leu Gly Leu Arg Glu Glu Lys Pro Ala Val Pro
1               5                   10                  15

Glu Ala Ser Ala Ser Pro Lys Gln Arg Arg Ser Ile Ile Arg Asp Arg
                20                  25                  30

Gly Pro Met Tyr Asp Asp Pro Thr Leu Pro Glu Gly Trp Thr Arg Lys
            35                  40                  45

Leu Lys Gln Arg Lys Ser Gly Arg Ser Ala Gly Lys Tyr Asp Val Tyr
        50                  55                  60

Leu Ile Asn Pro Gln Gly Lys Ala Phe Arg Ser Lys Val Glu Leu Ile
65                  70                  75                  80

Ala Tyr Phe Glu Lys Val Gly Asp Thr Ser Leu Asp Pro Asn Asp Phe
                85                  90                  95

Asp Phe Thr Val Thr Gly Arg Gly Ser Pro Ser Arg Arg Glu Gln Lys
            100                 105                 110

Pro Pro Gly Ser Ser Gly Ser Ser Gly Pro Lys Lys Arg Lys Val
        115                 120                 125

Pro Gly Ser Val Val Ala Ala Ala Ala Glu Ala Lys Lys Lys Ala
    130                 135                 140

Val Lys Glu Ser Ser Ile Arg Ser Val Gln Glu Thr Val Leu Pro Ile
145                 150                 155                 160

Lys Lys Arg Lys Thr Arg Glu Thr Val
                165

<210> SEQ ID NO 20
<211> LENGTH: 10
<212> TYPE: PRT
<213> ORGANISM: Artificial Sequence
<220> FEATURE:
<223> OTHER INFORMATION: C-terminal c-Myc epitope tag

<400> SEQUENCE: 20

Glu Gln Lys Leu Ile Ser Glu Glu Asp Leu
1               5                   10

<210> SEQ ID NO 21
<211> LENGTH: 515
<212> TYPE: PRT
<213> ORGANISM: Artificial Sequence
<220> FEATURE:
<223> OTHER INFORMATION: MeCP2 protein comprising a heterologous sequence

<400> SEQUENCE: 21

```
Met Ala Ala Ala Ala Ala Pro Ser Gly Gly Gly Gly Gly
 1               5                  10                  15

Glu Glu Glu Arg Leu Glu Glu Lys Ser Glu Asp Gln Asp Leu Gln Gly
             20                  25                  30

Leu Lys Asp Lys Pro Leu Lys Phe Lys Lys Val Lys Lys Asp Lys Lys
             35                  40                  45

Glu Glu Lys Glu Gly Lys His Glu Pro Val Gln Pro Ser Ala His His
         50                  55                  60

Ser Ala Glu Pro Ala Glu Ala Gly Lys Ala Glu Thr Ser Glu Gly Ser
 65                  70                  75                  80

Gly Ser Ala Pro Ala Val Pro Glu Ala Ser Ala Ser Pro Lys Gln Arg
                 85                  90                  95

Arg Ser Ile Ile Arg Asp Arg Gly Pro Met Tyr Asp Asp Pro Thr Leu
             100                 105                 110

Pro Glu Gly Trp Thr Arg Lys Leu Lys Gln Arg Lys Ser Gly Arg Ser
             115                 120                 125

Ala Gly Lys Tyr Asp Val Tyr Leu Ile Asn Pro Gln Gly Lys Ala Phe
         130                 135                 140

Arg Ser Lys Val Glu Leu Ile Ala Tyr Phe Glu Lys Val Gly Asp Thr
145                 150                 155                 160

Ser Leu Asp Pro Asn Asp Phe Asp Phe Thr Val Thr Gly Arg Gly Ser
                 165                 170                 175

Pro Ser Arg Arg Glu Gln Lys Pro Pro Lys Lys Pro Lys Ser Pro Lys
             180                 185                 190

Ala Pro Gly Thr Gly Arg Gly Arg Gly Arg Pro Lys Gly Ser Gly Thr
         195                 200                 205

Thr Arg Pro Lys Ala Ala Thr Ser Glu Gly Val Gln Val Lys Arg Val
210                 215                 220

Leu Glu Lys Ser Pro Gly Lys Leu Leu Val Lys Met Pro Phe Gln Thr
225                 230                 235                 240

Ser Pro Gly Gly Lys Ala Glu Gly Gly Gly Ala Thr Thr Ser Thr Gln
                 245                 250                 255

Val Met Val Ile Lys Arg Pro Gly Arg Lys Arg Lys Ala Glu Ala Asp
             260                 265                 270

Pro Gln Ala Ile Pro Lys Lys Arg Gly Arg Lys Pro Gly Ser Val Val
         275                 280                 285

Ala Ala Ala Ala Glu Ala Lys Lys Lys Ala Val Lys Glu Ser Ser
         290                 295                 300

Ile Arg Ser Val Gln Glu Thr Val Leu Pro Ile Lys Lys Arg Lys Thr
305                 310                 315                 320

Arg Glu Thr Val Ser Ile Glu Val Lys Glu Val Val Lys Pro Leu Leu
                 325                 330                 335

Val Ser Thr Leu Gly Glu Lys Ser Gly Lys Gly Leu Lys Thr Cys Lys
             340                 345                 350

Ser Pro Gly Arg Lys Ser Lys Glu Ser Ser Pro Lys Gly Arg Ser Ser
             355                 360                 365

Ser Ala Ser Ser Pro Pro Lys Lys Glu His His His His His His
         370                 375                 380

Ser Glu Ser Pro Lys Ala Pro Val Pro Leu Leu Pro Pro Leu Pro Pro
385                 390                 395                 400
```

```
Pro Pro Pro Glu Pro Ser Ser Glu Asp Pro Thr Ser Pro Pro Glu
                405                 410                 415

Pro Gln Asp Leu Ser Ser Val Cys Lys Glu Glu Lys Met Pro Arg
        420                 425                 430

Gly Gly Ser Leu Glu Ser Asp Gly Cys Pro Lys Glu Pro Ala Lys Thr
        435                 440                 445

Gln Pro Ala Val Ala Thr Ala Ala Thr Ala Ala Glu Lys Tyr Lys His
    450                 455                 460

Arg Gly Glu Gly Glu Arg Lys Asp Ile Val Ser Ser Met Pro Arg
465                 470                 475                 480

Pro Asn Arg Glu Glu Pro Val Asp Ser Arg Thr Pro Val Thr Glu Arg
                485                 490                 495

Val Ser Ser Arg Gly Pro Phe Glu Gln Lys Leu Ile Ser Glu Glu Asp
                500                 505                 510

Leu Val Asp
        515

<210> SEQ ID NO 22
<211> LENGTH: 284
<212> TYPE: PRT
<213> ORGANISM: Artificial Sequence
<220> FEATURE:
<223> OTHER INFORMATION: A c-Myc-tagged version of the Delta NC protein

<400> SEQUENCE: 22

Met Ala Ala Ala Ala Ala Ala Pro Ser Gly Gly Gly Gly Gly Gly
1               5                   10                  15

Glu Glu Glu Arg Leu Glu Glu Lys Pro Ala Val Pro Glu Ala Ser Ala
                20                  25                  30

Ser Pro Lys Gln Arg Arg Ser Ile Ile Arg Asp Arg Gly Pro Met Tyr
            35                  40                  45

Asp Asp Pro Thr Leu Pro Glu Gly Trp Thr Arg Lys Leu Lys Gln Arg
    50                  55                  60

Lys Ser Gly Arg Ser Ala Gly Lys Tyr Asp Val Tyr Leu Ile Asn Pro
65                  70                  75                  80

Gln Gly Lys Ala Phe Arg Ser Lys Val Glu Leu Ile Ala Tyr Phe Glu
                85                  90                  95

Lys Val Gly Asp Thr Ser Leu Asp Pro Asn Asp Phe Asp Phe Thr Val
            100                 105                 110

Thr Gly Arg Gly Ser Pro Ser Arg Arg Glu Gln Lys Pro Pro Lys Lys
        115                 120                 125

Pro Lys Ser Pro Lys Ala Pro Gly Thr Gly Arg Gly Arg Gly Arg Pro
    130                 135                 140

Lys Gly Ser Gly Thr Thr Arg Pro Lys Ala Ala Thr Ser Glu Gly Val
145                 150                 155                 160

Gln Val Lys Arg Val Leu Glu Lys Ser Pro Gly Lys Leu Leu Val Lys
                165                 170                 175

Met Pro Phe Gln Thr Ser Pro Gly Gly Lys Ala Glu Gly Gly Gly Ala
            180                 185                 190

Thr Thr Ser Thr Gln Val Met Val Ile Lys Arg Pro Gly Arg Lys Arg
        195                 200                 205

Lys Ala Glu Ala Asp Pro Gln Ala Ile Pro Lys Lys Arg Gly Arg Lys
    210                 215                 220

Pro Gly Ser Val Val Ala Ala Ala Ala Glu Ala Lys Lys Lys Ala
225                 230                 235                 240
```

```
Val Lys Glu Ser Ser Ile Arg Ser Val Gln Glu Thr Val Leu Pro Ile
                245                 250                 255

Lys Lys Arg Lys Thr Arg Glu Val Gly Ser Ser Gly Ser Ser Gly
            260                 265                 270

Glu Gln Lys Leu Ile Ser Glu Glu Asp Leu Val Asp
        275                 280

<210> SEQ ID NO 23
<211> LENGTH: 200
<212> TYPE: PRT
<213> ORGANISM: Artificial Sequence
<220> FEATURE:
<223> OTHER INFORMATION: c-Myc-tagged version of the Delta NIC protein

<400> SEQUENCE: 23

Met Ala Ala Ala Ala Ala Ala Pro Ser Gly Gly Gly Gly Gly Gly
1               5                   10                  15

Glu Glu Glu Arg Leu Glu Glu Lys Pro Ala Val Pro Glu Ala Ser Ala
            20                  25                  30

Ser Pro Lys Gln Arg Arg Ser Ile Ile Arg Asp Arg Gly Pro Met Tyr
        35                  40                  45

Asp Asp Pro Thr Leu Pro Glu Gly Trp Thr Arg Lys Leu Lys Gln Arg
50                  55                  60

Lys Ser Gly Arg Ser Ala Gly Lys Tyr Asp Val Tyr Leu Ile Asn Pro
65                  70                  75                  80

Gln Gly Lys Ala Phe Arg Ser Lys Val Glu Leu Ile Ala Tyr Phe Glu
                85                  90                  95

Lys Val Gly Asp Thr Ser Leu Asp Pro Asn Asp Phe Asp Phe Thr Val
            100                 105                 110

Thr Gly Arg Gly Ser Pro Ser Arg Arg Glu Gln Lys Pro Pro Gly Ser
        115                 120                 125

Ser Gly Ser Ser Gly Pro Lys Lys Lys Arg Lys Val Pro Gly Ser Val
    130                 135                 140

Val Ala Ala Ala Ala Ala Glu Ala Lys Lys Lys Ala Val Lys Glu Ser
145                 150                 155                 160

Ser Ile Arg Ser Val Gln Glu Thr Val Leu Pro Ile Lys Lys Arg Lys
                165                 170                 175

Thr Arg Glu Thr Val Gly Ser Ser Gly Ser Ser Gly Glu Gln Lys Leu
            180                 185                 190

Ile Ser Glu Glu Asp Leu Val Asp
        195                 200

<210> SEQ ID NO 24
<211> LENGTH: 130
<212> TYPE: PRT
<213> ORGANISM: Artificial Sequence
<220> FEATURE:
<223> OTHER INFORMATION: 5' transcriptional control comprising an amino
      acid sequence

<400> SEQUENCE: 24

Ala Ala Ala Cys Cys Ala Gly Cys Cys Cys Thr Cys Thr Gly Thr
1               5                   10                  15

Gly Cys Cys Cys Thr Ala Gly Cys Cys Gly Cys Thr Cys Thr Thr
            20                  25                  30

Thr Thr Thr Thr Cys Cys Ala Ala Gly Thr Gly Ala Cys Ala Gly Thr
        35                  40                  45

Ala Gly Ala Ala Cys Thr Cys Cys Ala Cys Cys Ala Ala Thr Cys Cys
```

```
            50                  55                  60
Gly Cys Ala Gly Cys Thr Gly Ala Ala Thr Gly Gly Gly Thr Cys
65                  70                  75                  80

Cys Gly Cys Cys Thr Cys Thr Thr Thr Cys Cys Cys Thr Gly Cys
                85                  90                  95

Cys Thr Ala Ala Ala Cys Ala Gly Cys Ala Gly Gly Ala Ala Cys
                100                 105                 110

Thr Cys Cys Thr Gly Cys Cys Ala Ala Thr Thr Gly Ala Gly Gly
            115                 120                 125

Cys Gly
    130

<210> SEQ ID NO 25
<211> LENGTH: 62
<212> TYPE: DNA
<213> ORGANISM: Artificial Sequence
<220> FEATURE:
<223> OTHER INFORMATION: 5' transcriptional control region comprising a
      silencer element

<400> SEQUENCE: 25
ttaagcgcca gagtccacaa gggcccagtt aatcctcaac attcaaatgc tgcccacaaa    60
ac                                                                   62

<210> SEQ ID NO 26
<211> LENGTH: 19
<212> TYPE: DNA
<213> ORGANISM: Artificial Sequence
<220> FEATURE:
<223> OTHER INFORMATION: 5' transcriptional control region comprising a
      CNS regulatory element

<400> SEQUENCE: 26
cagcacacag gctggtcgg                                                 19

<210> SEQ ID NO 27
<211> LENGTH: 29
<212> TYPE: DNA
<213> ORGANISM: Artificial Sequence
<220> FEATURE:
<223> OTHER INFORMATION: a miR-22 binding site

<400> SEQUENCE: 27
acaagaataa aggcagctgt tgtctcttc                                      29

<210> SEQ ID NO 28
<211> LENGTH: 30
<212> TYPE: DNA
<213> ORGANISM: Artificial Sequence
<220> FEATURE:
<223> OTHER INFORMATION: a miR-19 binding site

<400> SEQUENCE: 28
agaagtagct ttgcactttt ctaaactagg                                     30

<210> SEQ ID NO 29
<211> LENGTH: 30
<212> TYPE: DNA
<213> ORGANISM: Artificial Sequence
<220> FEATURE:
<223> OTHER INFORMATION: a miR-132 binding site

<400> SEQUENCE: 29
```

```
aatatcacca ggactgttac tcaatgtgtg                                      30

<210> SEQ ID NO 30
<211> LENGTH: 13
<212> TYPE: RNA
<213> ORGANISM: Artificial Sequence
<220> FEATURE:
<223> OTHER INFORMATION: 3'UTR of the MeCP2 gene, AU-rich element

<400> SEQUENCE: 30
auauauuuaa aaa                                                        13

<210> SEQ ID NO 31
<211> LENGTH: 23
<212> TYPE: RNA
<213> ORGANISM: Artificial Sequence
<220> FEATURE:
<223> OTHER INFORMATION: MeCP2 gene, GU-rich region

<400> SEQUENCE: 31
uguccguuug ugucuuuugu ugu                                             23

<210> SEQ ID NO 32
<211> LENGTH: 6043
<212> TYPE: DNA
<213> ORGANISM: Artificial Sequence
<220> FEATURE:
<223> OTHER INFORMATION: 2nd generation expression cassette

<400> SEQUENCE: 32
tgcgcgctcg ctcgctcact gaggccgccc gggcaaagcc cgggcgtcgg gcgacctttg     60
gtcgcccggc ctcagtgagc gagcgagcgc gcagagaggg agtggggttc ggtacccata    120
ggcgccaaga gcctagactt ccttaagcgc cagagtccac aagggcccag ttaatcctca    180
acattcaaat gctgcccaca aaaccagccc ctctgtgccc tagccgcctc ttttttccaa    240
gtgacagtag aactccacca atccgcagct gaatggggtc cgcctctttt ccctgcctaa    300
acagacagga actcctgcca attgagggcg tcaccgctaa ggctccgccc cagcctgggc    360
tccacaacca atgaagggta atctcgacaa agagcaaggg gtggggcgcg ggcgcgcagg    420
tgcagcagca cacaggctgg tcgggagggc ggggcgcgac gtctgccgtg cggggtcccg    480
gcatcggttg cgcgcgcgct ccctcctctc ggagagaggg ctgtggtaaa cccgtccgg     540 aaaccatggc cgccgccgcc gccgccgcgc cgagcggagg aggaggagga ggcgaggagg    600
agagactgga agaaaagtca gaagaccagg acctccaggg cctcaaggac aaaccccctca   660 agtttaaaaa ggtgaagaaa gataagaaag aagagaaaga gggcaagcat gagcccgtgc    720
agccatcagc ccaccactct gctgagcccg cagaggcagg caaagcagag acatcagaag    780
ggtcaggctc cgccccggct gtgccggaag cttctgcctc ccccaaacag cggcgctcca    840
tcatccgtga ccggggaccc atgtatgatg accccaccct gcctgaaggc tggacacgga    900
agcttaagca aaggaaatct ggccgctctg ctggaagta tgatgtgtat ttgatcaatc     960
cccagggaaa agcctttcgc tctaaagtgg agttgattgc gtacttcgaa aaggtaggcg   1020
acacatccct ggaccctaat gattttgact tcacggtaac tgggagaggg agcccctccc   1080
ggcgagagca gaaaccacct aagaagccca atctcccaa agctccagga actggcagag   1140
gccggggacg ccccaaaggg agcggcacca cgagacccaa gcggccacg tcagagggtg    1200 tgcaggtgaa aagggtcctg gagaaaagtc ctggaagct ccttgtcaag atgccttttc    1260
aaacttcgcc agggggcaag gctgaggggg gtggggccac cacatccacc caggtcatgg   1320
```

```
tgatcaaacg ccccggcagg aagcgaaaag ctgaggccga ccctcaggcc attcccaaga    1380
aacggggccg aaagccgggg agtgtggtgg cagccgctgc cgccgaggcc aaaaagaaag    1440
ccgtgaagga gtcttctatc cgatctgtgc aggagaccgt actccccatc aagaagcgca    1500 agaccccggga gacggtcagc atcgaggtca aggaagtggt gaagcccctg ctggtgtcca    1560
ccctcggtga agagcggg aaaggactga agacctgtaa gagccctggg cggaaaagca      1620
aggagagcag ccccaagggg cgcagcagca gcgcctcctc accccccaag aaggagcacc    1680
accaccatca ccaccactca gagtccccaa aggcccccgt gccactgctc ccacccctgc    1740
ccccacctcc acctgagccc gagagctccg aggaccccac cagccccccct gagcccagg    1800 acttgagcag cagcgtctgc aaagaggaga agatgcccag aggaggctca ctggagagcg    1860
acggctgccc caaggagcca gctaagactc agcccgcgt tgccaccgcc gccacggccg     1920
cagaaaagta caaacaccga gggagggag agcgcaaaga cattgtttca tcctccatgc    1980
caaggccaaa cagagaggag cctgtggaca gccggacgcc cgtgaccgag agagttagct    2040
ctagagggcc cttcgaacaa aaactcatct cagaagagga tctggtcgac tagagctcgc    2100
tgatcagcct cacaagaata aaggcagctg ttgtctcttc agaagtagct ttgcactttt    2160
ctaaactagg aatatcacca ggactgttac tcaatgtgtg ggtaccgaaa gcactgatat    2220
atttaaaaac aaaggtgta acctatttat tatataaaga gtttgcctta taaatttaca    2280
taaaaatgtc cgtttgtgtc ttttgttgta aaatcacgc gtaggaaccc ctagtgatgg    2340
agttggccac tccctctctg cgcgctcgct cgctcactga ggccgggcga ccaaaggtcg    2400
cccgacgccc gggctttgcc cgggcggcct cagtgagcga gcgagcgcgc agctggcgta    2460
atagcgaaga ggcccgcacc gatcgccctt cccaacagtt gcgcagcctg aatggcgaat    2520
ggcgattccg ttgcaatggc tggcggtaat attgttctgg atattaccag caaggccgat    2580
agtttgagtt cttctactca ggcaagtgat gttattacta atcaaagaag tattgcgaca    2640
acggttaatt tgcgtgatgg acagactctt ttactcggtg gcctcactga ttataaaaac    2700
acttctcagg attctggcgt accgttcctg tctaaaatcc ctttaatcgg cctcctgttt    2760
agctcccgct ctgattctaa cgaggaaagc acgttatacg tgctcgtcaa agcaaccata    2820
gtacgcgccc tgtagcggcg cattaagcgc ggcgggtgtg gtggttacgc gcagcgtgac    2880
cgctacactt gccagcgccc tagcgcccgc tcctttcgct ttcttccctt cctttctcgc    2940
cacgttcgcc ggctttcccc gtcaagctct aaatcggggg ctccctttag ggttccgatt    3000
tagtgcttta cggcacctcg accccaaaaa acttgattag ggtgatggtt cacgtagtgg    3060
gccatcgccc tgatagacgg ttttttcgccc tttgacgttg gagtccacgt tctttaatag    3120
tggactcttt ttccaaactg gaacaacact caacccctatc tcggtctatt cttttgattt    3180
ataagggatt tgccgatttt cggcctattg gttaaaaaat gagctgattt aacaaaaatt    3240
taacgcgaat tttaacaaaa tattaacgct tacaatttaa atatttgctt atacaatctt    3300 cctgttttg gggcttttct gattatcaac cggggtacat atgattgaca tgctagtttt    3360
acgattaccg ttcatcgatt ctcttgtttg ctccagactc tcaggcaatg acctgatagc    3420 cttttgtagag acctctcaaa aatagctacc ctctccggca tgaatttatc agctagaacg    3480
gttgaatatc atattgatgg tgatttgact gtctccggcc tttctcaccc gtttgaatct    3540
ttacctacac attactcagg cattgcattt aaaatatatg agggttctaa aaattttttat    3600 ccttgcgttg aaataaaggc ttctcccgca aaagtattac agggtcataa tgttttttggt    3660
```

```
acaaccgatt tagctttatg ctctgaggct ttattgctta attttgctaa ttctttgcct      3720
tgcctgtatg atttattgga tgttggaatt cctgatgcgg tattttctcc ttacgcatct      3780
gtgcggtatt tcacaccgca tatggtgcac tctcagtaca atctgctctg atgccgcata      3840
gttaagccag ccccgacacc cgccaacacc cgctgacgcg ccctgacggg cttgtctgct      3900
cccggcatcc gcttacagac aagctgtgac cgtctccggg agctgcatgt gtcagaggtt      3960
ttcaccgtca tcaccgaaac gcgcgagacg aaagggcctc gtgatacgcc tatttttata      4020
ggttaatgtc atgataataa tggtttctta gacgtcaggt ggcacttttc ggggaaatgt      4080
gcgcggaacc cctatttgtt tatttttcta aatacattca aatatgtatc cgctcatgag      4140
acaataaccc tgataaatgc ttcaataata ttgaaaaagg aagagtatga gtattcaaca      4200
tttccgtgtc gcccttattc ccttttttgc ggcattttgc cttcctgttt ttgctcaccc      4260
agaaacgctg gtgaaagtaa aagatgctga agatcagttg ggtgcacgag tgggttacat      4320
cgaactggat ctcaacagcg gtaagatcct tgagagtttt cgccccgaag aacgttttcc      4380
aatgatgagc acttttaaag ttctgctatg tggcgcggta ttatcccgta ttgacgccgg      4440
gcaagagcaa ctcggtcgcc gcatacacta ttctcagaat gacttggttg agtactcacc      4500
agtcacagaa aagcatctta cggatggcat gacagtaaga gaattatgca gtgctgccat      4560
aaccatgagt gataacactg cggccaactt acttctgaca acgatcggag gaccgaagga      4620
gctaaccgct tttttgcaca acatggggga tcatgtaact cgccttgatc gttgggaacc      4680
ggagctgaat gaagccatac caaacgacga gcgtgacacc acgatgcctg tagcaatggc      4740
aacaacgttg cgcaaactat taactggcga actacttact ctagcttccc ggcaacaatt      4800
aatagactgg atggaggcgg ataaagttgc aggaccactt ctgcgctcgg cccttccggc      4860
tggctggttt attgctgata atctggagcc ggtgagcgt gggtctcgcg gtatcattgc      4920
agcactgggg ccagatggta agccctcccg tatcgtagtt atctacacga cggggagtca      4980
ggcaactatg gatgaacgaa atagacagat cgctgagata ggtgcctcac tgattaagca      5040
ttggtaactg tcagaccaag tttactcata tatactttag attgatttaa aacttcattt      5100
ttaatttaaa aggatctagg tgaagatcct ttttgataat ctcatgacca aaatccctta      5160
acgtgagttt tcgttccact gagcgtcaga ccccgtagaa aagatcaaag gatcttcttg      5220
agatcctttt tttctgcgcg taatctgctg cttgcaaaca aaaaaaccac cgctaccagc      5280
ggtggtttgt ttgccggatc aagagctacc aactcttttt ccgaaggtaa ctggcttcag      5340
cagagcgcag ataccaaata ctgtccttct agtgtagccg tagttaggcc accacttcaa      5400
gaactctgta gcaccgccta catacctcgc tctgctaatc ctgttaccag tggctgctgc      5460
cagtggcgat aagtcgtgtc ttaccgggtt ggactcaaga cgatagttac cggataaggc      5520
gcagcggtcg ggctgaacgg ggggttcgtg cacacagccc agcttggagc gaacgaccta      5580
caccgaactg agatacctac agcgtgagct atgagaaagc gccacgcttc ccgaagggag      5640
aaaggcggac aggtatccgg taagcggcag ggtcggaaca ggagagcgca cgagggagct      5700
tccaggggga aacgcctggt atctttatag tcctgtcggg tttcgccacc tctgacttga      5760
gcgtcgattt tgtgatgct cgtcaggggg cggagcctat ggaaaaacg ccagcaacgc      5820 ggccttttta cggttcctgg ccttttgctg gccttttgct cacatgttct tcctgcgtt      5880 atcccctgat tctgtggata accgtattac cgcctttgag tgagctgata ccgctcgccg      5940
cagccgaacg accgagcgca gcgagtcagt gagcgaggaa gcggaagagc gcccaatacg      6000
caaaccgcct ctccccgcgc gttggccgat tcattaatgc agc                       6043
```

<210> SEQ ID NO 33
<211> LENGTH: 2199
<212> TYPE: DNA
<213> ORGANISM: Artificial Sequence
<220> FEATURE:
<223> OTHER INFORMATION: 2nd Generation Expression Cassette

<400> SEQUENCE: 33

```
ataggcgcca agagcctaga cttccttaag cgccagagtc cacaagggcc cagttaatcc     60
tcaacattca aatgctgccc acaaaaccag cccctctgtg ccctagccgc ctcttttttc    120
caagtgacag tagaactcca ccaatccgca gctgaatggg gtccgcctct tttccctgcc    180
taaacagaca ggaactcctg ccaattgagg gcgtcaccgc taaggctccg ccccagcctg    240
ggctccacaa ccaatgaagg gtaatctcga caaagagcaa ggggtggggc gcgggcgcgc    300
aggtgcagca gcacacaggc tggtcgggag ggcggggcgc gacgtctgcc gtgcggggtc    360
ccggcatcgg ttgcgcgcgc gctccctcct ctcggagaga gggctgtggt aaaacccgtc    420
cggaaaccat ggccgccgcc gccgccgccg cgccgagcgg aggaggagga ggaggcgagg    480
aggagagact ggaagaaaag tcagaagacc aggacctcca gggcctcaag gacaaacccc    540
tcaagtttaa aaaggtgaag aaagataaga agaagagaa agagggcaag catgagcccg    600
tgcagccatc agcccaccac tctgctgagc ccgcagaggc aggcaaagca gagacatcag    660
aagggtcagg ctccgccccg gctgtgccgg aagcttctgc ctcccccaaa cagcggcgct    720
ccatcatccg tgaccgggga cccatgtatg atgaccccac cctgcctgaa ggctggacac    780
ggaagcttaa gcaaaggaaa tctggccgct ctgctgggaa gtatgatgtg tatttgatca    840 atcccccaggg aaaagccttt cgctctaaag tggagttgat tgcgtacttc gaaaaggtag    900
gcgacacatc cctggaccct aatgattttg acttcacggt aactgggaga gggagcccct    960
cccggcgaga gcagaaacca cctaagaagc ccaaatctcc caaagctcca ggaactggca   1020
gaggccgggg acgccccaaa gggagcggca ccacgagacc caaggcggcc acgtcagagg   1080
gtgtgcaggt gaaaagggtc ctggagaaaa gtcctgggaa gctccttgtc aagatgcctt   1140
ttcaaacttc gccaggggc aaggctgagg ggggtgggc caccacatcc acccaggtca    1200
tggtgatcaa acgccccggc aggaagcgaa aagctgaggc cgaccctcag gccattccca   1260
agaaacgggg ccgaaagccg gggagtgtgg tggcagccgc tgccgccgag gccaaaaaga   1320
aagccgtgaa ggagtcttct atccgatctg tgcaggagac cgtactcccc atcaagaagc   1380 gcaagaccc ggagacggtc agcatcgagg tcaaggaagt ggtgaagccc ctgctggtgt   1440
ccaccctcgg tgagaagagc gggaaaggac tgaagacctg taagagccct gggcggaaaa   1500
gcaaggagag cagccccaag gggcgcagca gcgcgcctc ctcacccccc aagaaggagc   1560
accaccacca tcaccaccac tcagagtccc caaaggcccc cgtgccactg ctcccacccc   1620
tgcccccacc tccacctgag cccgagagct ccgaggaccc caccagcccc ctgagcccc   1680 aggacttgag cagcagcgtc tgcaaagagg agaagatgcc cagaggaggc tcactggaga   1740
gcgacggctg ccccaaggag ccagctaaga ctcagcccgc ggttgccacc gccgccacgg   1800
ccgcagaaaa gtacaaacac cgaggggagg gagagcgcaa agacattgtt tcatcctcca   1860
tgccaaggcc aaacagagag gagcctgtgg acagccggac gcccgtgacc gagagagtta   1920
gctctagagg gcccttcgaa caaaaactca tctcagaaga ggatcggtc gactagagct   1980 cgctgatcag cctcacaaga ataaaggcag ctgttgtctc ttcagaagta gctttgcact   2040
```

| | |
|---|---|
| tttctaaact aggaatatca ccaggactgt tactcaatgt gtgggtaccg aaagcactga | 2100 |
| tatatttaaa aacaaaaggt gtaacctatt tattatataa agagtttgcc ttataaattt | 2160 |
| acataaaaat gtccgtttgt gtcttttgtt gtaaaaatc | 2199 |

<210> SEQ ID NO 34
<211> LENGTH: 2199
<212> TYPE: DNA
<213> ORGANISM: Artificial Sequence
<220> FEATURE:
<223> OTHER INFORMATION: 2nd Generation Expression Cassette

<400> SEQUENCE: 34

| | |
|---|---|
| tatccgcggt tctcggatct gaaggaattc gcggtctcag gtgttcccgg gtcaattagg | 60 |
| agttgtaagt ttacgacggg tgttttggtc ggggagacac gggatcggcg gagaaaaaag | 120 |
| gttcactgtc atcttgaggt ggttaggcgt cgacttaccc caggcggaga aaagggacgg | 180 |
| atttgtctgt ccttgaggac ggttaactcc cgcagtggcg attccgaggc ggggtcggac | 240 |
| ccgaggtgtt ggttacttcc cattagagct gtttctcgtt ccccaccccg cgcccgcgcg | 300 |
| tccacgtcgt cgtgtgtccg accagccctc ccgccccgcg ctgcagacgg cacgccccag | 360 |
| ggccgtagcc aacgcgcgcg cgagggagga gagcctctct cccgacacca ttttgggcag | 420 |
| gcctttggta ccggcggcgg cggcggcggc gcggctcgcc tcctcctcct cctccgctcc | 480 |
| tcctctctga ccttctttc agtcttctgg tcctggaggt cccggagttc ctgtttgggg | 540 |
| agttcaaatt tttccacttc tttctattct ttcttctctt tctcccgttc gtactcgggc | 600 |
| acgtcggtag tcgggtggtg agacgactcg ggcgtctccg tccgtttcgt ctctgtagtc | 660 |
| ttcccagtcc gaggcgggc cgacacggcc ttcgaagacg gaggggtttt gtcgccgcga | 720 |
| ggtagtaggc actggcccct gggtacatac tactggggtg ggacggactt ccgacctgtg | 780 |
| ccttcgaatt cgtttccttt agaccggcga gacgacccttt catactacac ataaactagt | 840 |
| tagggtccc ttttcggaaa gcgagatttc accttcaacta acgcatgaag cttttccatc | 900 |
| cgctgtgtag ggacctggga ttactaaaac tgaagtgcca ttgaccctct ccctcgggga | 960 |
| gggccgctct cgtctttggt ggattcttcg ggtttagagg gtttcgaggt ccttgaccgt | 1020 |
| ctccggcccc tgcgggggttt ccctcgccgt ggtgctctgg gttccgccgg tgcagtctcc | 1080 |
| cacacgtcca cttttcccag gacctctttt caggacccctt cgaggaacag ttctacggaa | 1140 |
| aagtttgaag cggtcccccg ttccgactcc ccccacccccg gtggtgtagg tgggtccagt | 1200 |
| accactagtt tgcgggggccg tccttcgctt ttcgactccg gctgggagtc cggtaagggt | 1260 |
| tctttgcccc ggctttcggc ccctcacacc accgtcggcg acggcggctc cggtttttct | 1320 |
| ttcggcactt cctcagaaga taggctagac acgtcctctg gcatgagggg tagttcttcg | 1380 |
| cgttctgggc cctctgccag tcgtagctcc agttccttca ccacttcggg gacgaccaca | 1440 |
| ggtgggagcc actcttctcg cccttttcctg acttctggac attctcggga cccgccttt | 1500 |
| cgttcctctc gtcgggttc cccgcgtcgt cgtcgcggag gagtgggggg ttcttcctcg | 1560 |
| tggtggtggt agtggtggtg agtctcaggg gtttccgggg gcacggtgac gagggtgggg | 1620 |
| acggggggtgg aggtggactc gggctctcga ggctcctggg gtggtcgggg ggactcgggg | 1680 |
| tcctgaactc gtcgtcgcag acgttctcc tcttctacgg gtctcctccg agtgacctct | 1740 |
| cgctgccgac ggggttcctc ggtcgattct gagtcgggcg ccaacggtgg cggcggtgcc | 1800 |
| ggcgtctttt catgtttgtg gctccctcc ctctcgcgtt tctgtaacaa agtaggaggt | 1860 |
| acggttccgg tttgtctctc ctcggacacc tgtcggcctg cgggcactgg ctctctcaat | 1920 |

```
cgagatctcc cgggaagctt gttttttgagt agagtcttct cctagaccag ctgatctcga    1980
gcgactagtc ggagtgttct tatttccgtc gacaacagag aagtcttcat cgaaacgtga    2040
aaagatttga tccttatagt ggtcctgaca atgagttaca cacccatggc tttcgtgact    2100
atataaattt ttgttttcca cattggataa ataatatatt tctcaaacgg aatatttaaa    2160
tgtattttta caggcaaaca cagaaaacaa cattttag                            2199
```

MECP2 EXPRESSION CASSETTES

CLAIM OF PRIORITY

This application is a National Stage Application of PCT Application No. PCT/GB2018/050773 filed on Mar. 23, 2018 titled "MeCP2 Expression Cassettes" which in turn claims priority to Provisional Application No. GB1704722.6 filed on Mar. 24, 2017 and Provisional Application No. GB1704704.4 filed on Mar. 24, 2017, and each of which is incorporated herein by reference in its entirety.

FIELD OF THE INVENTION

The invention relates to an expression cassette comprising a gene encoding MeCP2 protein, and to viral vectors, especially vectors derived from adeno-associated virus (AAV), for use in therapeutic delivery of such expression cassettes.

The instant application contains a replacement Sequence Listing which has been submitted electronically in ASCII text file format and is hereby incorporated by reference in its entirety. Said ASCII text file, created on Jun. 13, 2023, is named Replacement_Sequence_Listing_136526_001201.txt and is 62,714 bytes in size.

BACKGROUND TO THE INVENTION

Rett syndrome (RTT; OMIM 312750) is a neurological disorder characterized by a constellation of clinical diagnostic and associated features and with overt onset occurring several months postnatally[1]. Typical RTT is almost exclusively caused by de novo germline mutations in the X-linked gene, MECP2[2]; reviewed in[3, 4]. Several mouse models of RTT have been generated that harbour Mecp2 deletions[5-7] or knocked-in mutations[8-11]. Many of these models recapitulate the principal features that characterize RTT in humans, although there are differences that reflect the phenotypic variability seen in patients[12-14]. Despite the severity of RTT-like phenotypes, genetic reactivation of silenced Mecp2 in conditional knockout mice resulted in a robust and enduring reversal of phenotypes[15-17].

This inherent reversibility of the phenotype, added to the lack of obvious targets for pharmacotherapy, makes gene therapy an obvious candidate therapeutic strategy in RTT. However, there are significant challenges to a gene transfer approach, including the requirement to transduce sufficient numbers of neurons in the brain[16] and the avoidance of deleterious overexpression[18].

Previous attempts at MECP2 gene transfer using AAV9 vectors were confounded by limited brain transduction efficiency and toxicity[19, 20], while efficacy in other studies using self-complementary AAV (scAAV)[21] may have been compromised by use of a construct exceeding the packaging capacity of the vector.

SUMMARY OF THE INVENTION

Despite the progress made in recent years in establishing the suitability of Rett syndrome for treatment by gene transfer, existing vectors pose efficacy and safety concerns. Low levels of transduction or gene expression may not successfully rescue the affected phenotype, while overexpression results in toxicity. Consequently there remains a need for vectors for delivery of MeCP2 which have improved efficacy and/or safety profiles compared to currently available options.

Vectors based on adeno-associated virus (AAV) are promising candidates for gene delivery but have limited capacity, being capable of carrying a genome of about 4.7 kb to about 5 kb of single stranded DNA. An AAV vector genome possesses a 145 nucleotide palindromic repeat sequence at each end (also known as an inverted terminal repeat, or ITR), reducing the capacity of transgene payload to about 4.4 kb to about 4.7 kb.

The human MECP2 gene is large, having a very long 3' untranslated region of 8.5 kb in addition to the promoter and coding sequences. It is therefore impossible to include the entire gene, with all of its endogenous upstream and downstream regulatory sequences, in a recombinant AAV (rAAV) vector.

So-called "self complementary AAVs" (scAAVs) can provide more efficient transgene expression as compared to conventional rAAV vectors. However, an scAAV vector genome contains two copies of the same transgene payload in opposite orientations, and so in practice has only half the coding capacity of an rAAV vector, further exacerbating the difficulty.

The present invention provides a nucleic acid molecule comprising a MeCP2 expression cassette, the expression cassette comprising, in operable linkage from 5' to 3':
- a 5' transcriptional control region comprising a promoter capable of driving transcription in neural cells;
- an open reading frame encoding a MeCP2 protein;
- translation control signals;
- a 3' untranslated region (3'UTR) comprising one or more of:
  (i) a binding site for mir-22;
  (ii) a binding site for mir-19;
  (iii) a binding site for miR-132;
  (iv) a binding site for miR124; and
  (v) an AU-rich element; and
- transcriptional termination signals;

wherein the MeCP2 expression cassette is not more than about 5 kb in length.

The nucleic acid may be linear or circular, and single or double stranded. For example, the nucleic acid may be a plasmid or other expression vector, including a viral vector. Although much of the following discussion concentrates on AAV vectors, it will be understood that the expression cassette may also be employed in the context of other viral vectors, including adenoviral vectors and retroviral (e.g. lentiviral) vectors.

In some embodiments, e.g. when the expression cassette is for incorporation into a rAAV vector, the expression cassette may be not more than about 4.9 kb, 4.8 kb, 4.7 kb, 4.6 kb, 4.5 kb or 4.4 kb in length. Preferably it is not more than 4.4. kb in length.

The nucleic acid molecule may further comprise ITR sequences. Thus the nucleic acid molecule may comprise a 5' ITR and a 3' ITR, wherein the ITRs flank the expression cassette The nucleic acid molecule may be a rAAV genome. Thus the invention further provides a rAAV genome comprising a 5' ITR, a MeCP2 expression cassette of the invention, and a 3' ITR.

In other embodiments, e.g. when the expression cassette is for incorporation into a scAAV vector, the expression cassette may be not more than about 2.4 kb, not more than 2.3 kb, or not more than 2.2 kb in length. Preferably it is not more than 2.2 kb in length.

An scAAV vector genome comprises inverted repeats of the payload sequence located between the ITRs. Thus it is possible for the vector genome molecule to adopt a hairpin-like structure in which the two complementary payload sequences hybridise to one another intramolecularly, or for two copies of the full-length genome to hybridise to one another via the payload sequences. (The ITR sequences will not necessarily hybridise to one another, because the ITRs at each end may not have precisely complementary sequences, and also because each ITR is likely to form its own internal secondary structure.)

Thus the invention further provides a nucleic acid molecule comprising, from 5' to 3', a MeCP2 expression cassette of the invention and the reverse complement of said expression cassette.

The nucleic acid molecule may further comprise ITR sequences. Thus the nucleic acid molecule may comprise a 5' ITR, a MeCP2 expression cassette of the invention, the reverse complement of said expression cassette, and a 3' ITR. The nucleic acid molecule may be a scAAV vector genome.

The ITR sequences may be from any suitable AAV type. For example, they may be from AAV2.

An AAV vector may have genomic ITRs from a first serotype ("A") and proteins from a second serotype ("B"). Such a vector may be referred to as type "AAV A/B". However, since the viral proteins largely determine the serological properties of the virion particle, such a vector may still be referred to as being of serotype B.

The 5' transcription regulatory region may comprise one, two or all three of the core MeCP2 promoter, the MeCP2 silencer element, and a CNS regulatory element.

The 3'UTR typically comprises a binding site for one or more of miR-22, miR-19, miR-132 and miR-124. For example, it may contain binding sites for at least 2, at least 3, or all 4 of miR-22, miR-19, miR-132 and miR-124.

For example, the 3'UTR may contain binding sites for:
miR-22 and miR-19;
miR-22 and mir-132;
miR-22 and miR124;
miR-19 and miR-132;
miR-19 and miR-124;
miR-132 and miR-124;
miR-22, miR-19 and miR-132;
miR-22, miR-19 and miR-124;
miR-22, miR-132 and miR-124;
miR-19, miR-132 and miR-124;
or miR-22, miR-19, miR-132 and miR-124.

Additionally or alternatively, the 3'UTR may comprise an AU-rich element. Thus it may contain an AU-rich element alone, or in combination with binding sites for one or more of one of miR-22, miR-19, miR-132 and miR-124. For example, the 3'UTR may contain binding sites for at least 2, at least 3, or all 4 of miR-22, miR-19, miR-132 and miR-124 in combination with an AU-rich element.

For example, the 3'UTR may contain an AU-rich element in combination with binding sites for:
miR-22 and miR-19;
miR-22 and mir-132;
miR-22 and miR124;
miR-19 and miR-132;
miR-19 and miR-124;
miR-132 and miR-124;
miR-22, miR-19 and miR-132;
miR-22, miR-19 and miR-124;
miR-22, miR-132 and miR-124;
miR-19, miR-132 and miR-124;
or miR-22, miR-19, miR-132 and miR-124.

The AU-rich element and the miRNA binding sites regulate mRNA stability and/or expression from the mRNA. These elements may be present in any order. However, it may be desirable that those elements which are present occur in the order miR-22 site, miR-19 site, miR-132 site, AU-rich element and miR-124 site, from 5' to 3' of the sense strand.

The invention further provides an AAV virion particle comprising a nucleic acid molecule or AAV genome as described. The AAV genome may be a rAAV genome or a scAAV genome.

The virion particle may be regarded as a gene delivery vehicle for delivering nucleic acid encoding MeCP2 protein to a target cell, and capable of inducing expression of MeCP2 protein in a target cell.

The AAV virion may be of any suitable serotype. Serotypes AAV9 and AAV PHP.B may be particularly preferred due to their capacity for transduction of neural cells.

The invention further provides a cell comprising a nucleic acid as described herein. The cell may, for example, be a packaging cell, capable of producing a virion particle as described.

The cell will be capable of expressing AAV proteins (e.g. rep and cap proteins) and of supporting assembly and release of infectious AAV virion particles as described. It may also possess helper virus functions, e.g. from adenovirus, E1-deleted adenovirus or herpesvirus.

The invention further provides a nucleic acid or AAV virion particle as described herein for use in enhancing expression of MeCP2 protein in a target cell.

The invention further provides a nucleic acid or AAV virion particle as described herein for use in the treatment of Rett syndrome.

The invention further provides a pharmaceutical composition comprising a nucleic acid or AAV virion of the invention, optionally in combination with a pharmaceutically acceptable carrier.

The invention further provides a method of treatment of Rett syndrome in an subject in need thereof, comprising administering a nucleic acid or AAV virion particle as described herein to the subject. Administration may be via any suitable peripheral or central route, but intravenous and intrathecal administration may be particularly suitable.

The invention further provides the use of a nucleic acid or AAV virion particle in the preparation of a medicament for the treatment of Rett syndrome.

Thus the subject to whom the nucleic acid or virion is to be administered may already be affected by Rett syndrome, or may be at risk of developing Rett syndrome. The subject may have been identified as being affected by or at risk of developing Rett syndrome, e.g. by means of genetic testing, e.g. for one or more mutations (especially loss of function mutations) in the MECP2 gene.

Thus the invention provides a method comprising the step of testing a subject for the presence of one or more mutations in the MECP2 gene indicative of the presence of, or a predisposition to, Rett syndrome, and selecting the subject for treatment with a nucleic acid or AAV virion as described herein if one or more such mutations is identified.

Where a "nucleic acid molecule" is referred to in this specification, it may be RNA or DNA, and single or double stranded, unless the context requires otherwise.

An AAV genome molecule is necessarily a single stranded DNA molecule. Although an scAAV genome has the capacity to adopt a hairpin secondary structure, a single scAAV genome will generally be regarded herein as a single stranded molecule since it still consists only of a single continuous strand of DNA. A complex of two scAAV genomes hybridised to one another could be considered to be a double stranded molecule.

Reference is made in this specification to both DNA and RNA sequences. It will be apparent to the reader that sequences containing T refer to DNA molecules, such as AAV genome sequences or expression constructs, while sequences containing U refer to RNA molecules such as mRNA transcripts derived by transcription from DNA expression cassettes, e.g. in AAV genomes.

(a) Kaplan-Meier survival plot for Mecp2$^{-/y}$ mice injected with different doses [$1\times10^{11}$ (n=10), $1\times10^{12}$ (n=8) and $1\times10^{13}$ (n=5) vg/mouse] of $1^{st}$ generation vector compared to vehicle-treated animals (WT; n=9, Mecp2$^{-/y}$; n=16). The median survival period in Mecp2$^{-/y}$ mice treated with $1\times10^{12}$ vg/mouse was significantly higher than that in vehicle-treated controls (27.14 versus 11.64 weeks, p=0.001, Mantel-Cox test). (b-c) plots showing mean bodyweight and aggregate severity scores, respectively, for Mecp2$^{-/y}$ mice treated with $1\times10^{11}$, $1\times10^{12}$ vg/mouse or vehicle. Arrows indicate age at injection; data presented as mean±SEM. (d) Dose-dependent transduction efficiency (Myc-positive nuclei as a proportion of DAPI-positive nuclei) across different brain regions. Data presented as mean±SEM (n=3 mice per group). CA1 indicates hippocampal region CA1.

Figure 2:
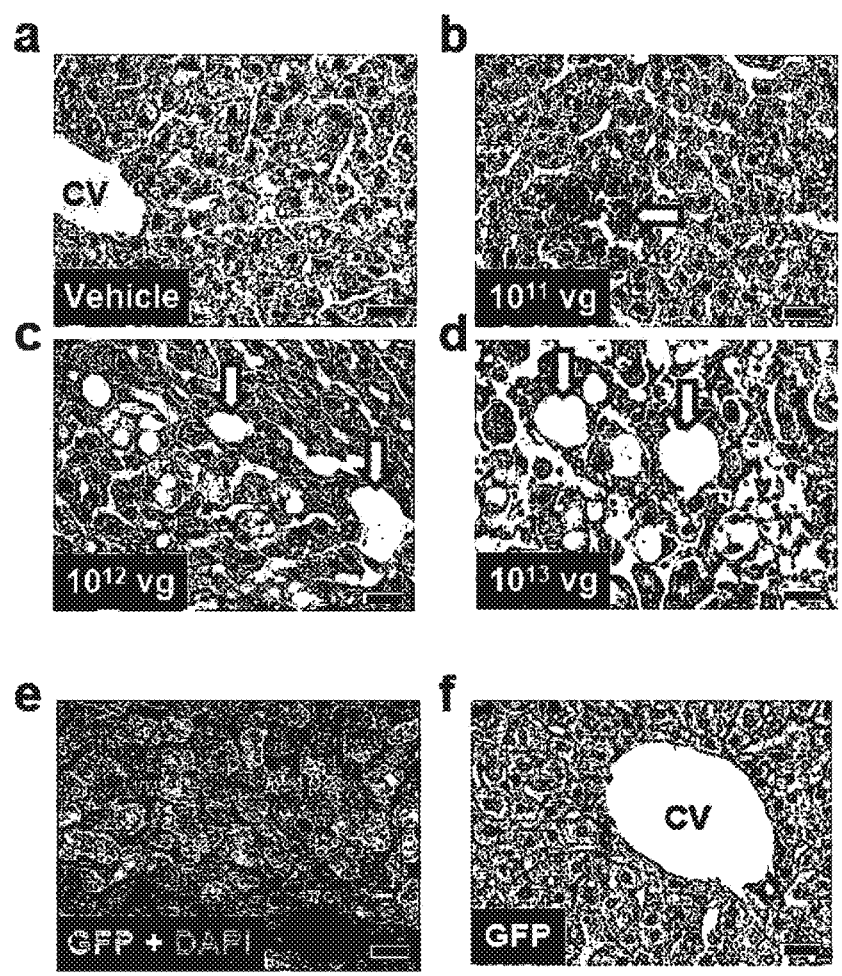

FIG. 2. Intravenous injection of the $1^{st}$ generation vector resulted in pathological changes in the liver.

(a-d) Representative H&E-stained liver sections from wild-type mice injected with (a) vehicle or (b-d) different doses of vector. (e) Liver section from a mouse injected intravenously with a GFP control vector, counterstained with DAPI. (f) Representative H&E-stained liver section from a GFP vector-treated mouse. Arrows indicate mononuclear cell infiltration, vacuolation and/or loss of hepatocytes. Dashed white line indicates cellular swelling. Scale bar indicates 20 μm; CV indicates central vein.

Figure 3:
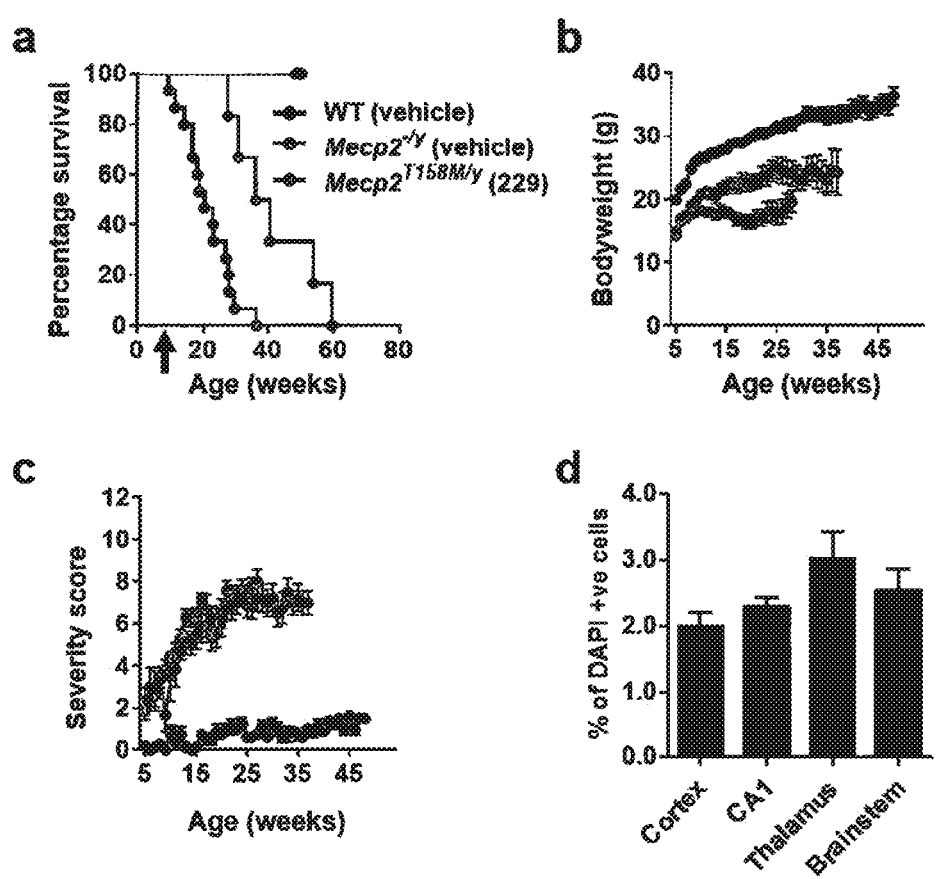

FIG. 3. Improved survival and bodyweight of Mecp2$^{T158M/Y}$ mice after systemic delivery of the $1^{st}$ generation vector.

(a) Survival plot for treated Mecp2$^{T158M/y}$ mice. Arrow indicates age at injection. (b-c) plots of bodyweight and aggregate severity score, respectively, for Mecp2$^{T158M/y}$ mice treated with $1\times10^{12}$ vg/mouse of $1^{st}$ generation vector and control groups (Mecp2$^{T158M/y}$ and WT) treated with vehicle. Data presented as mean±SEM. (d) Transduction efficiency in the brain of treated mice (Myc-positive nuclei as a proportion of DAPI-positive nuclei; n=3 mice).

Figure 4:
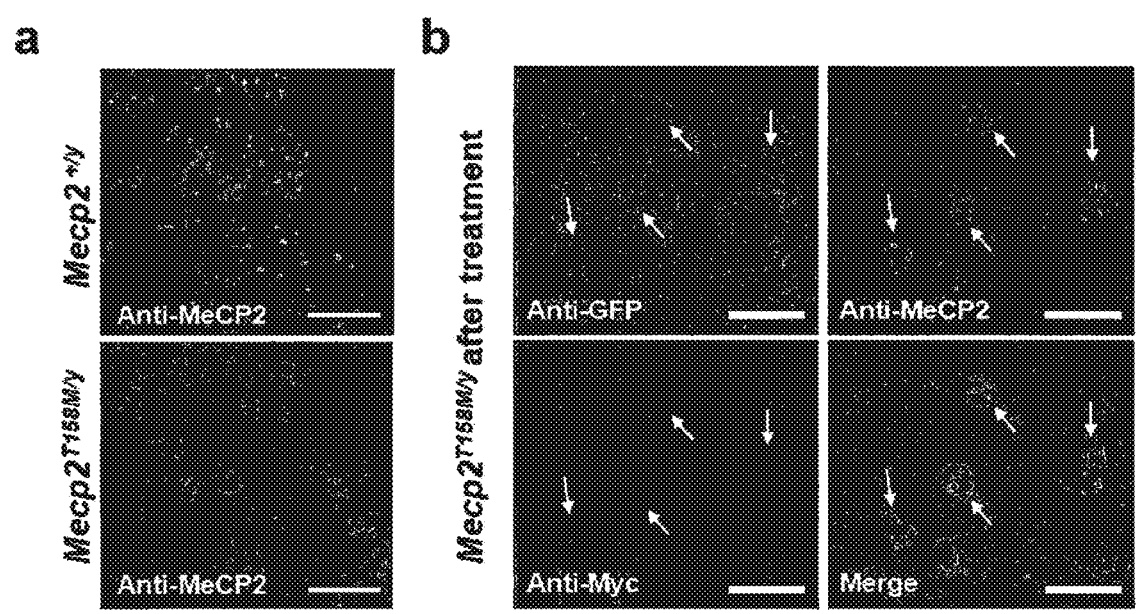

FIG. 4. Nuclear localisation of MeCP2 in untreated and treated Mecp2$^{T158M/Y}$ mice.

Representative confocal images of the CA1 region of the hippocampus. (a) Endogenous MeCP2 exhibits heterochromatin-enriched localisation in wild-type nuclei, while GFP-tagged MeCP2 exhibits decreased heterochromatin localization (i.e. more diffuse labelling) in nuclei from Mecp2$^{T158M/y}$ mice. (b) Images demonstrating heterochromatin-enriched localisation of exogenously-derived MeCP2 in nuclei of transduced cells in Mecp2$^{T158M/y}$ mice treated with the $1^{st}$ generation vector. White arrows indicate transduced cells (Myc-positive). Scale bar indicates 20 μm.

Figure 5:
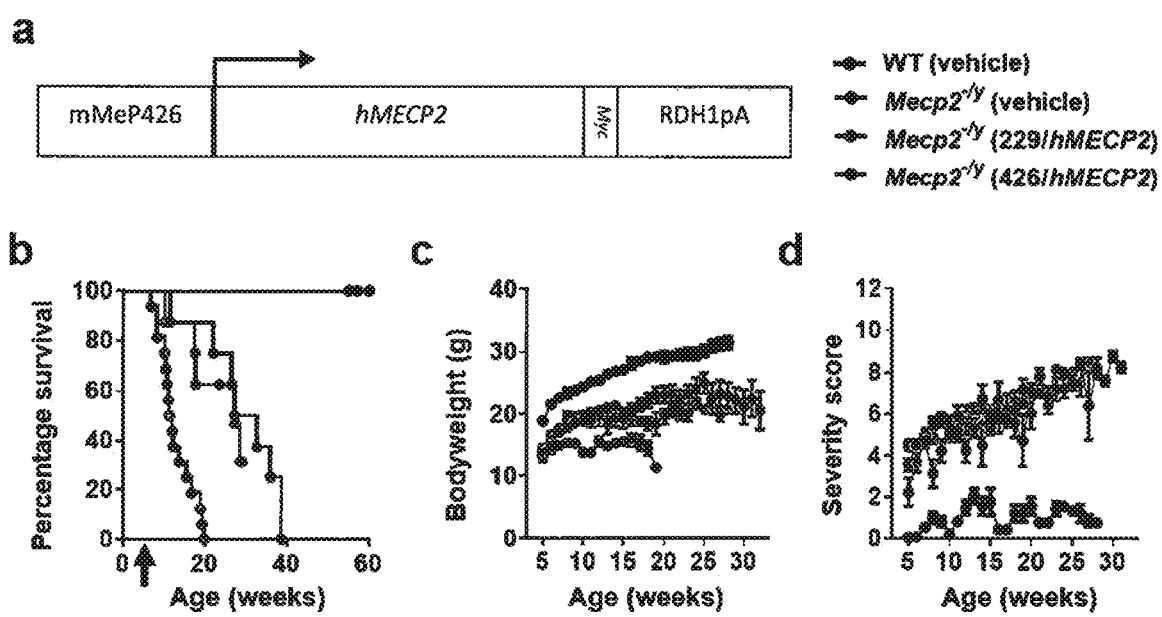

FIG. 5. Therapeutic efficacy of $2^{nd}$ generation vector after systemic delivery to Mecp2$^{-/y}$ mice.

Figure 7:
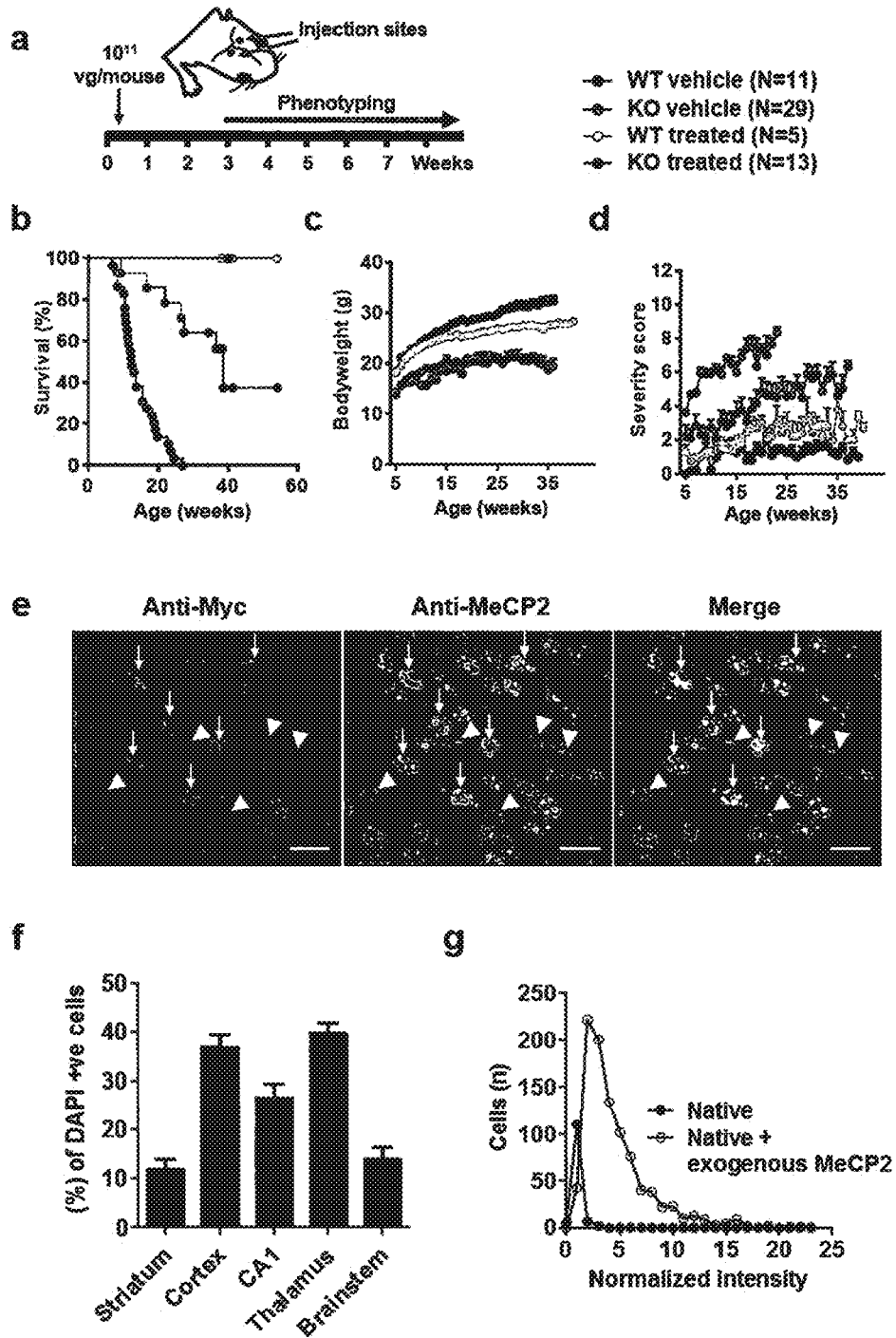

(a) Design features of our $2^{nd}$ generation vector summarized (see text and Suppl. FIG. 7 for details). (b) Survival plot for Mecp2$^{-/y}$ mice treated intravenously with $1\times10^{12}$ vg/mouse of the $2^{nd}$ generation vector (median survival=29.9 weeks) or an identical dose of $1^{st}$ generation vector (median survival=27.1 weeks) or vehicle (median survival=11.6 weeks). Arrow indicates age at injection. (c-d) Plots showing mean bodyweight and aggregate severity scores, respectively, of Mecp2$^{-/y}$ mice treated as in (b).

Figure 6:
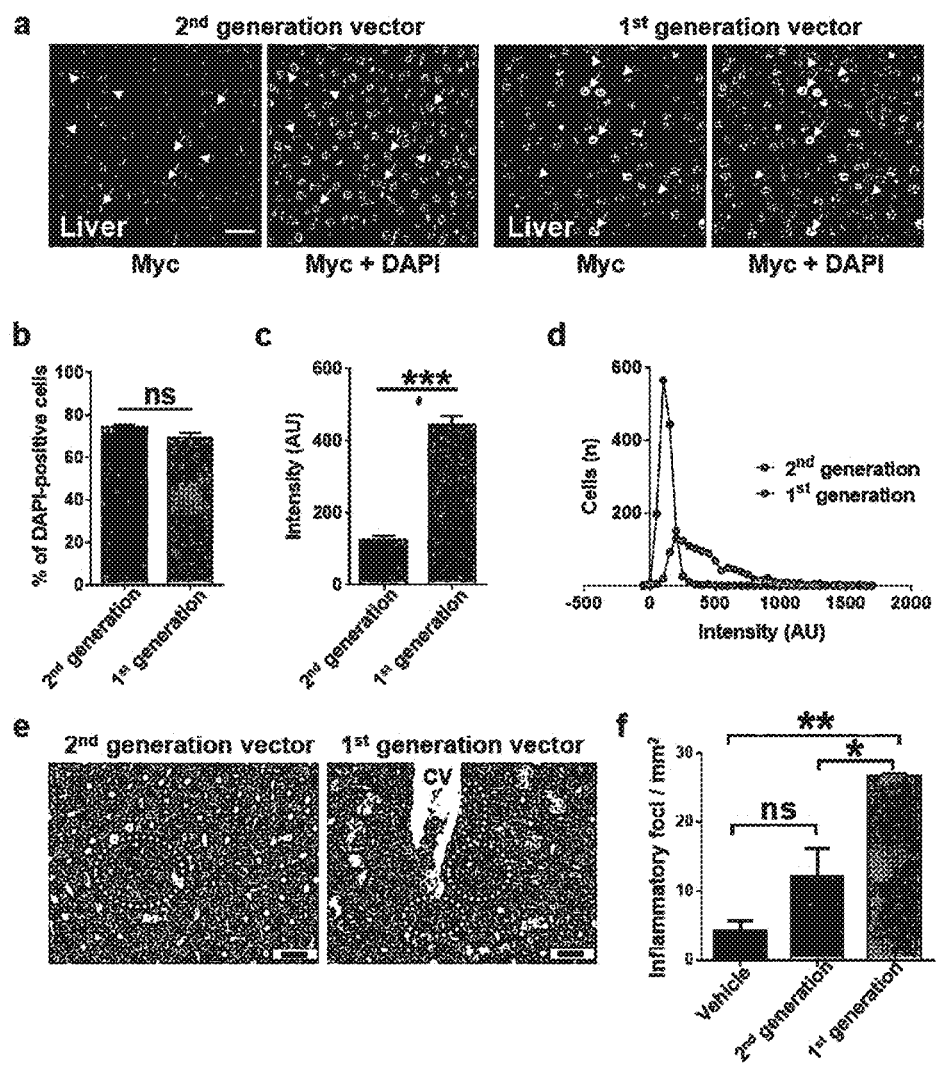

FIG. 6. Reduced expression of exogenous MeCP2 in the livers of mice treated with 2nd generation vector (a) Flattened confocal stack images from livers of mice one month after being injected intravenously at 5 weeks of age with the $2^{nd}$ generation vector or $1^{st}$ generation vector at $1\times10^{12}$ vg/mouse; confocal settings were the same in each case. Tissues were immunolabelled with anti-Myc and DAPI nuclear stain. Arrows indicate transduced cells (Myc-positive) and arrowheads indicate non-transduced cells. (b) Transduction efficiencies in the liver for both vectors. (c) Quantification of cellular levels of exogenous MeCP2 measured as anti-Myc immunofluorescence in transduced cells in the liver (n=3 mice, 1400 transduced cells). Data presented as mean±SEM. (d) Frequency distribution of cellular levels of exogenous MeCP2 in the liver, measured as in (c). (e) Liver sections stained with H&E showing vacuolation of hepatocytes (arrows) and sites of mononuclear cell infiltration (dashed circles). CV indicates central vein. White scale bar indicates 20 μm. (f) Quantification of density of inflammatory foci in the livers of treated mice (n=3 per group). Data presented as mean±SEM. * p<0.05,  p<0.01, * p<0.001.

FIG. 7. Direct brain delivery of $2^{nd}$ generation vector to neonatal Mecp2$^{-/y}$ mice revealed therapeutic efficacy.

(a) Experimental design. (b) Survival plot showing extended survival of neonatally treated Mecp2$^{-/y}$ mice (median survival=38.6 weeks; p<0.0001, Mantel-Cox test) compared with vehicle-treated animals (median survival=12.4 weeks). (c-d) Plots showing mean bodyweight and aggregate severity scores, respectively, for the mice shown in (b). (e) Representative confocal images from the cortex of injected wild-type mice. White arrows indicate transduced cells; arrowheads indicate non-transduced cells; scale bar indicates 20 μm. (f) Graph showing transduction efficiency in different brain regions (n=3 mice). (g) Frequency distribution of MeCP2 levels in transduced and non-transduced ('native') cells in the mouse cortex (n=3 mice; 954 transduced cells) data presented as mean±SEM.

Figure 8:
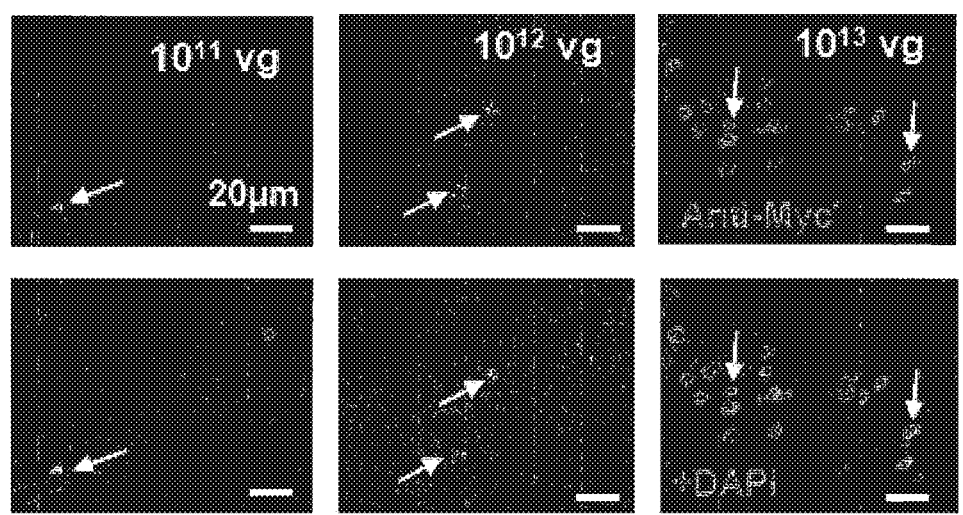

FIG. 8. Expression of exogenous MeCP2 in the brain after intravenous injection of the $1^{st}$ generation vector.

Figure 9:
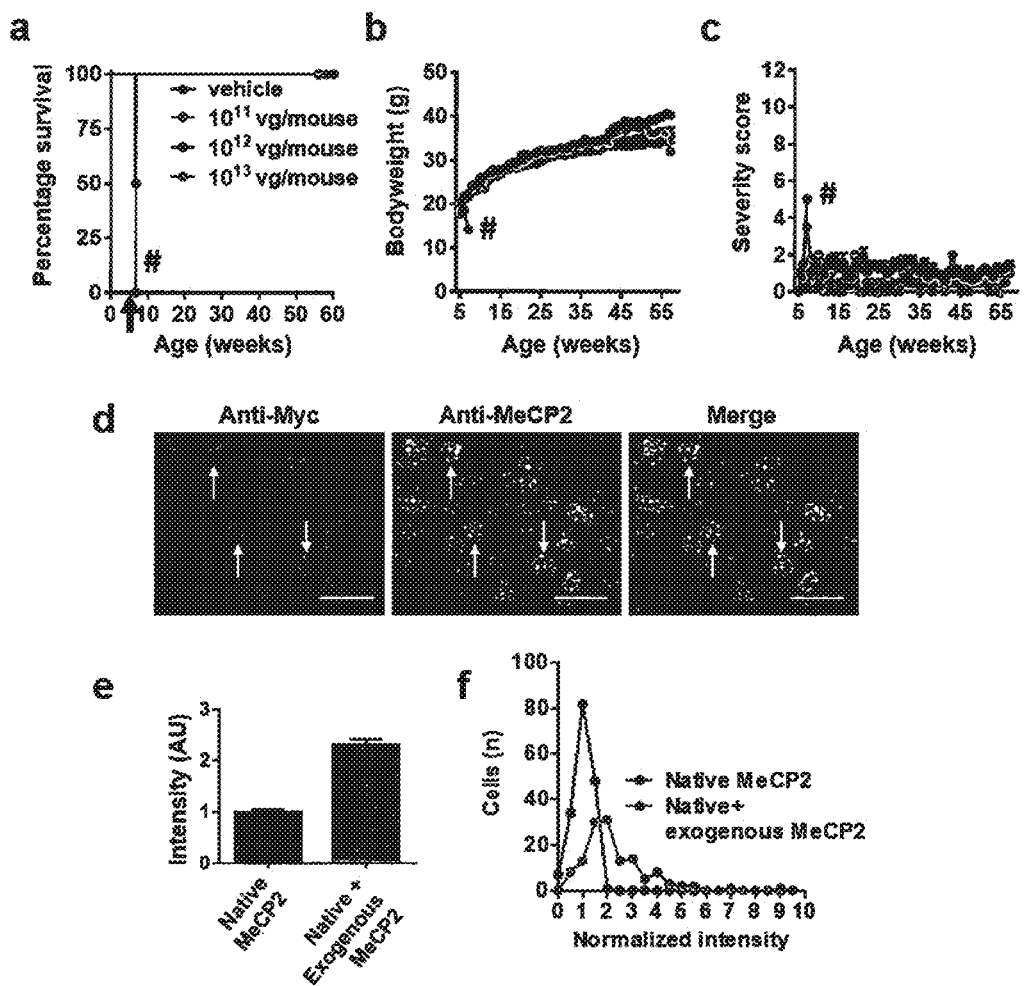

Representative confocal micrographs showing transgene expression in the hippocampal CA1 region in Mecp2$^{-/y}$ mice treated intravenously with $1\times10^{11}$, $1\times10^{12}$ and $1\times10^{13}$ vg/mouse of the $1^{st}$ generation vector (as revealed by anti-Myc tag immunolabeling). Arrows denote transduced cells and the lower panel shows co-localisation with DAPI. Scale bar=20 μm FIG. 9. Systemic delivery of the $1^{st}$ generation vector to wild-type mice is tolerated at low doses but toxic at high doses.

(a) Survival plot showing the early toxicity observed after IV injection of a $1\times10^{13}$ vg/mouse dose of the $1^{st}$ generation vector (green) compared to other doses and vehicle control. Arrow indicates age at injection. (b-c) Plots showing mean bodyweight and aggregate severity score, respectively, for these cohorts after injection. Data presented as mean±SEM.

(d) Flattened confocal stack images of the hippocampus CA1 region of wild-type mice injected with $1\times10^{13}$ vg/mouse of the $1^{st}$ generation vector. Tissues were immunolabelled with anti-Myc and anti-MeCP2 antibodies. White arrows indicate transduced cells. Scale bar indicates 20 µm. (e) Quantification of cellular levels of native MeCP2 and exogenous MeCP2 in transduced and non-transduced cells in the hippocampus CA1 region of wild-type mice (n=2 mice; 131 transduced cells and 172 non-transduced cells). Data presented as mean±SEM and normalised to native MeCP2. (f) Frequency distribution of normalised MeCP2 level in transduced and non-transduced cells. # indicates lethality at high dose.

Figure 10:
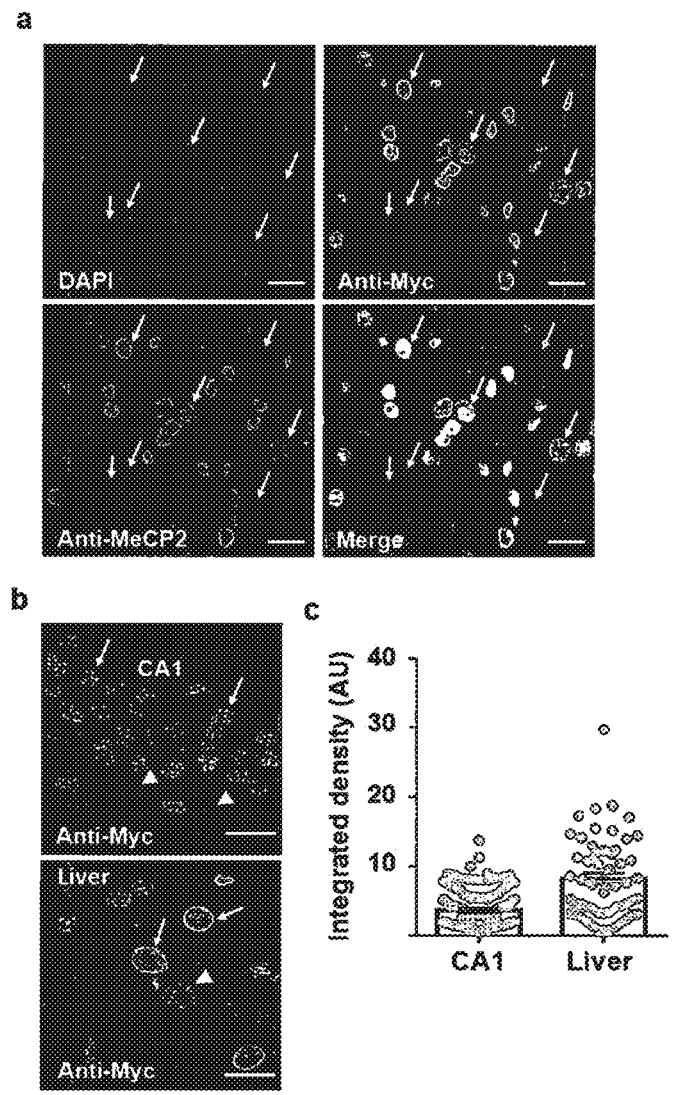

FIG. 10. Intravenous injection of $1^{st}$ generation vector resulted in high level of exogenous MeCP2 expression in the liver.

(a) Representative confocal images of liver taken from WT mice injected intravenously with $1^{st}$ generation vector at the dose of $1\times10^{13}$ vg/mouse. Sections were immunolabelled with anti-Myc (green), anti-MeCP2 (red) and DAPI nuclear stain (blue). White arrows indicate transduced cells, whereas yellow arrows indicate non-transduced cells. (b) Flattened confocal stack images taken from the CA1 region of the hippocampus (top) and from the liver (mice were injected intravenously with $1\times10^{13}$ vg/mouse) using the same confocal settings. Arrows indicate nuclei with a high level of exogenous MeCP2 expression (based on fluorescence intensity of the anti-Myc antibody) and arrowheads indicate nuclei with low expression levels. Scale bar in (a) & (b)=20 µm. (c) measurement of the integrated pixel intensity per nucleus in liver (55 transduced cells and CA1 (131 transduced cells) of the same mice (n=3 mice). Data presented as mean±SEM.

Figure 11:
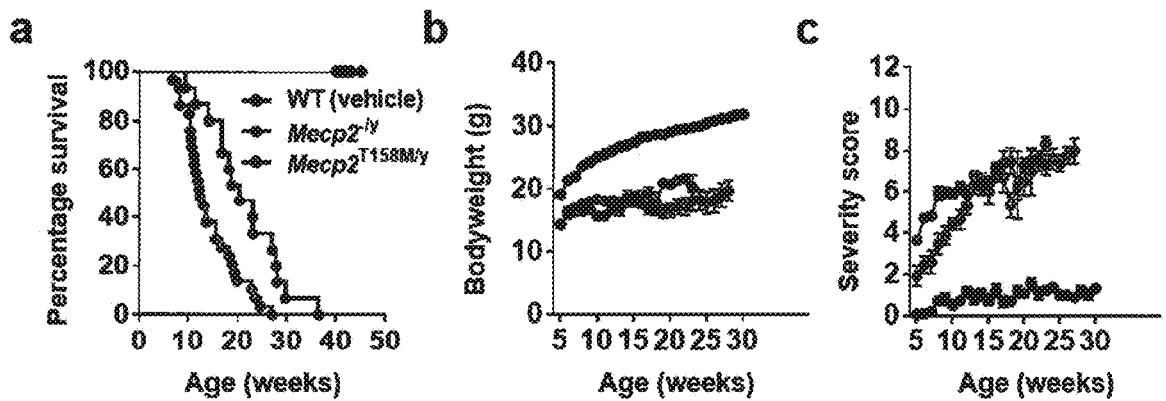

FIG. 11. Comparison of $Mecp2^{T158M/y}$ and $Mecp2^{-/y}$ mice.

(a) Survival plot for $Mecp2^{T158M/y}$ mice (n=15) and $Mecp2^{-/y}$ mice (n=29). (b-c) Plots showing no significant differences in mean bodyweight and aggregate severity score, respectively, between $Mecp2^{T158M/y}$ and $Mecp2^{-/y}$ mice. Data presented as mean±SEM.

Figure 12:
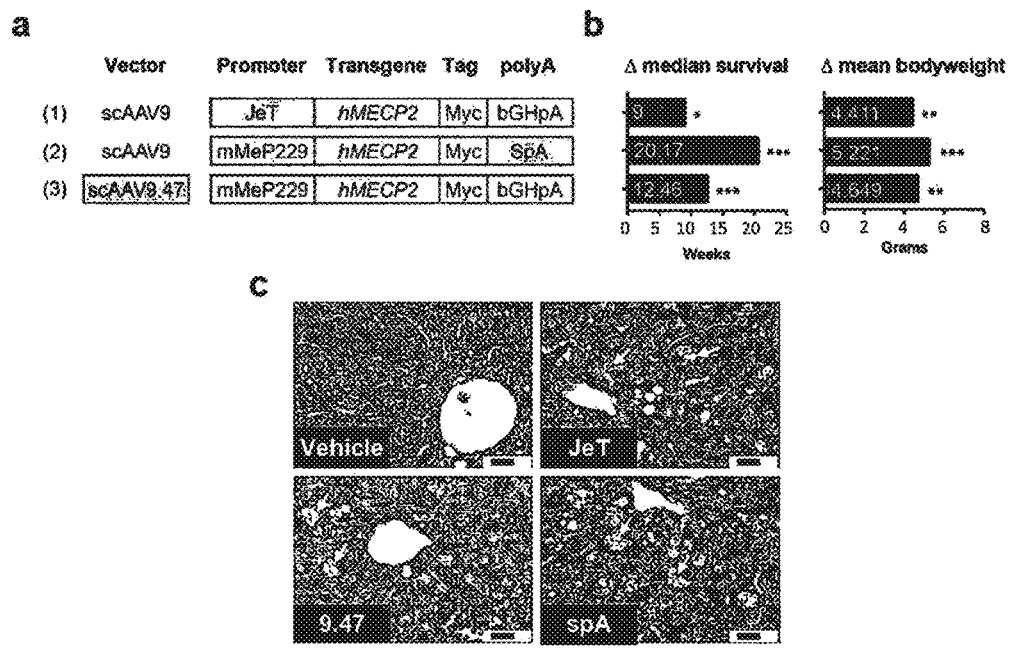

FIG. 12. Novel vector design features, efficacy and liver phenotype.

(a) A summary of the design differences for three of the novel vectors described in the text. (b) Efficacy of these three novel vectors after intravenous injection of $1\times10^{12}$ vg/mouse to 4-5 weeks old $Mecp2^{-/y}$ mice, expressed as increase in median survival relative to the vehicle controls (left; compared using Mantel-Cox test) and mean bodyweight at the age of 11 weeks (right) relative to the vehicle controls (one-way ANOVA with Tukey's post-hoc pairwise comparisons). * $p<0.05$,  $p<0.01$, * $p<0.001$. (c) Representative H&E-stained liver sections from mice injected with JeT, 9.47 or spA vectors. Arrows indicate vacuolation of hepatocytes; scale bar indicates 20 µm.

Figure 13:
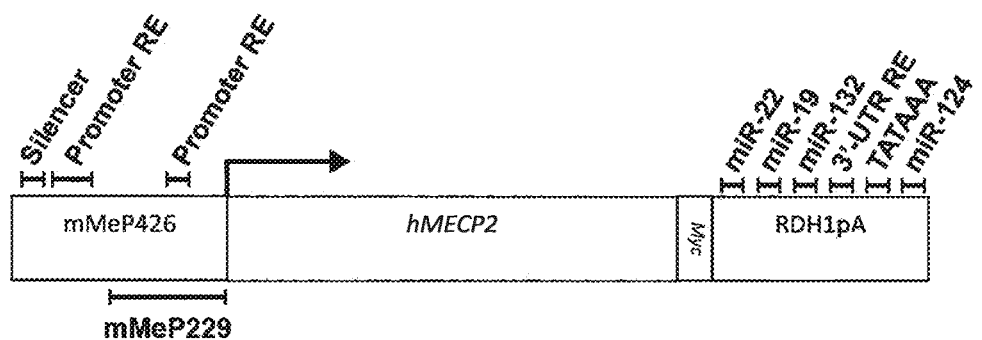

FIG. 13. Design of the $2^{nd}$ generation vector construct. Putative regulatory elements (RE) in the extended mMeP426 promoter and endogenous distal 3'-UTR are indicated. The extent of the mMeP229 promoter (used in the $1^{st}$ generation vector) is shown relative to mMeP426. The RDH1pA 3'-UTR consists of several exogenous microRNA (miR) binding sites incorporated as a 'binding panel' adjacent to a portion of the distal endogenous MECP2 polyadenylation signal and its accompanying regulatory elements. References with an asterisk indicate human in vitro studies, not rodent.

Figure 14:
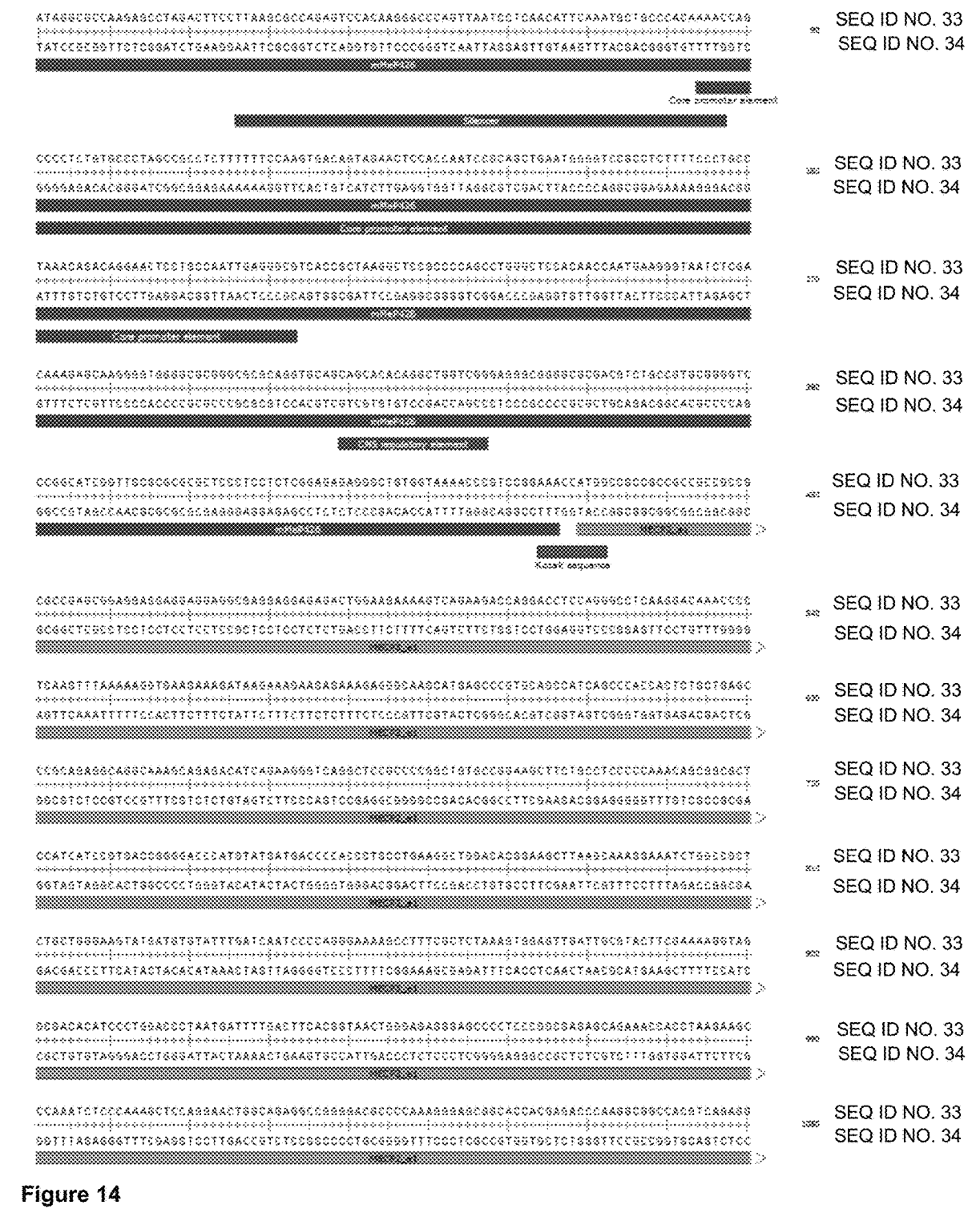
Figure 14:
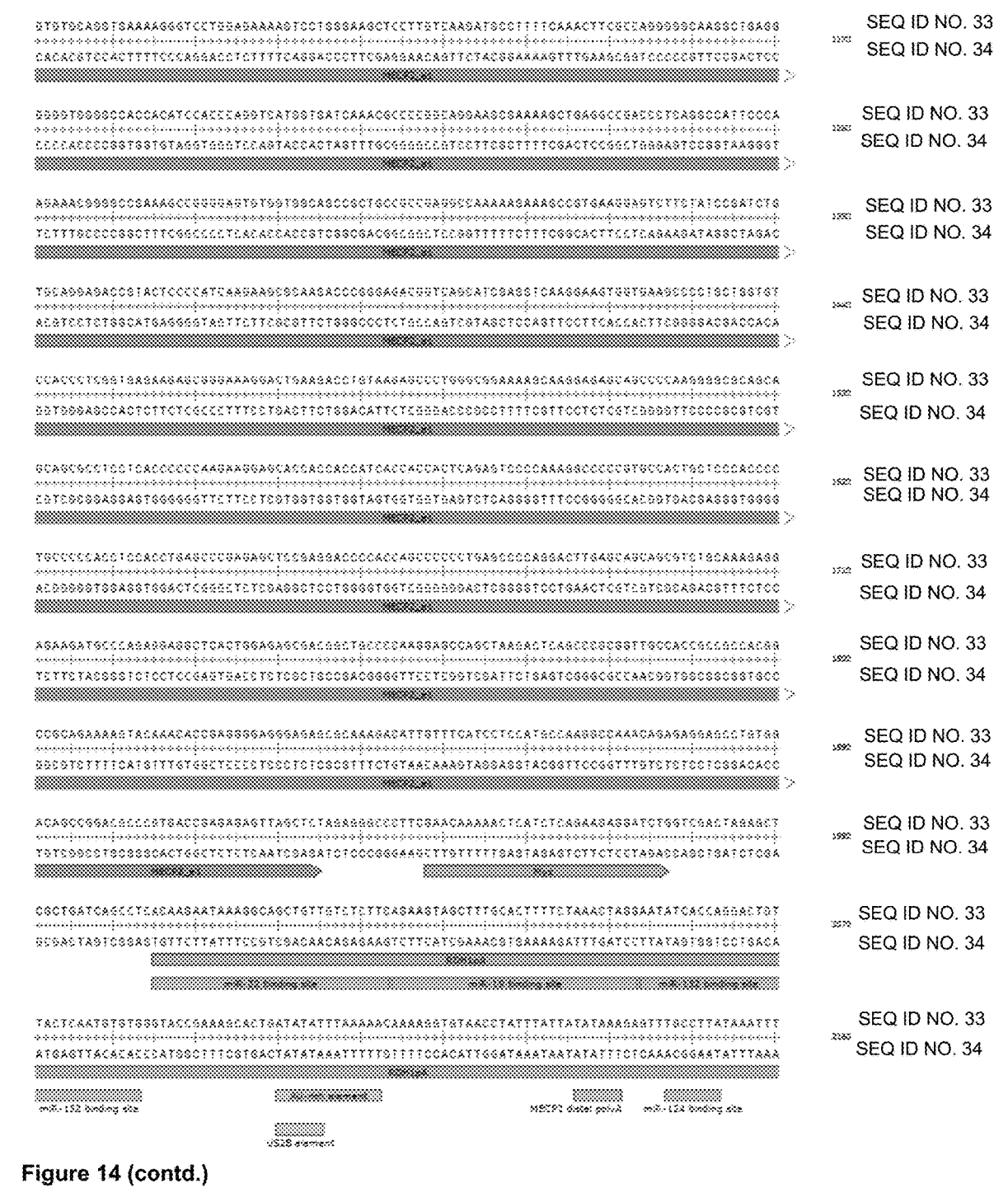

FIG. 14. Annotated sequence of $2^{nd}$ generation expression cassette (SEQ ID NO. 32 and SEQ ID NO. 33).

Figure 15:
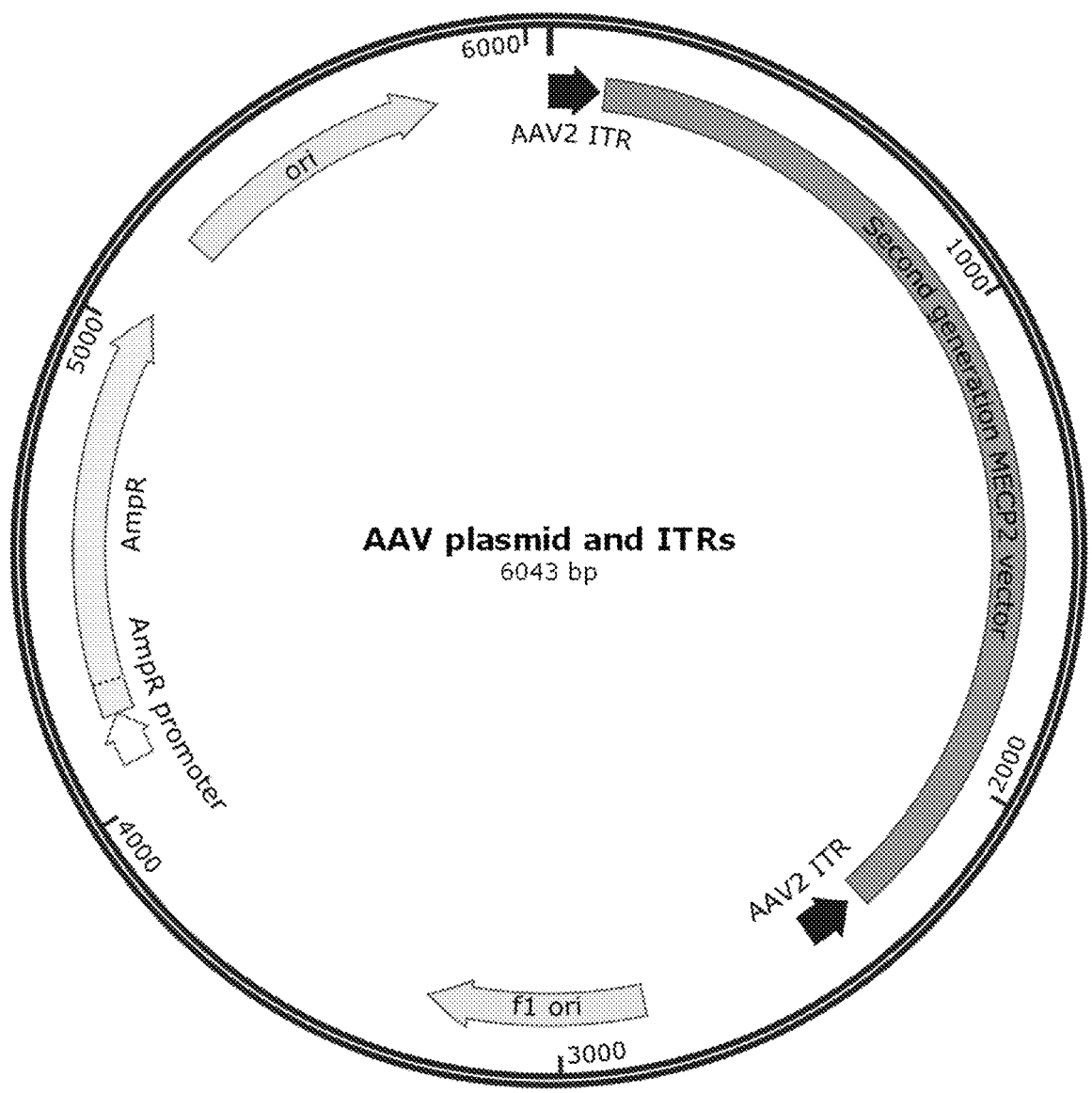

FIG. 15. Schematic diagram of plasmid encoding the second generation MeCP2 vector.

FIG. 16. Full sequence (SEQ ID NO: 32) of the plasmid shown in FIG. 15. The expression cassette illustrated in FIG. 14 is single-underlined and the ITRs are double-underlined.

Figure 17:
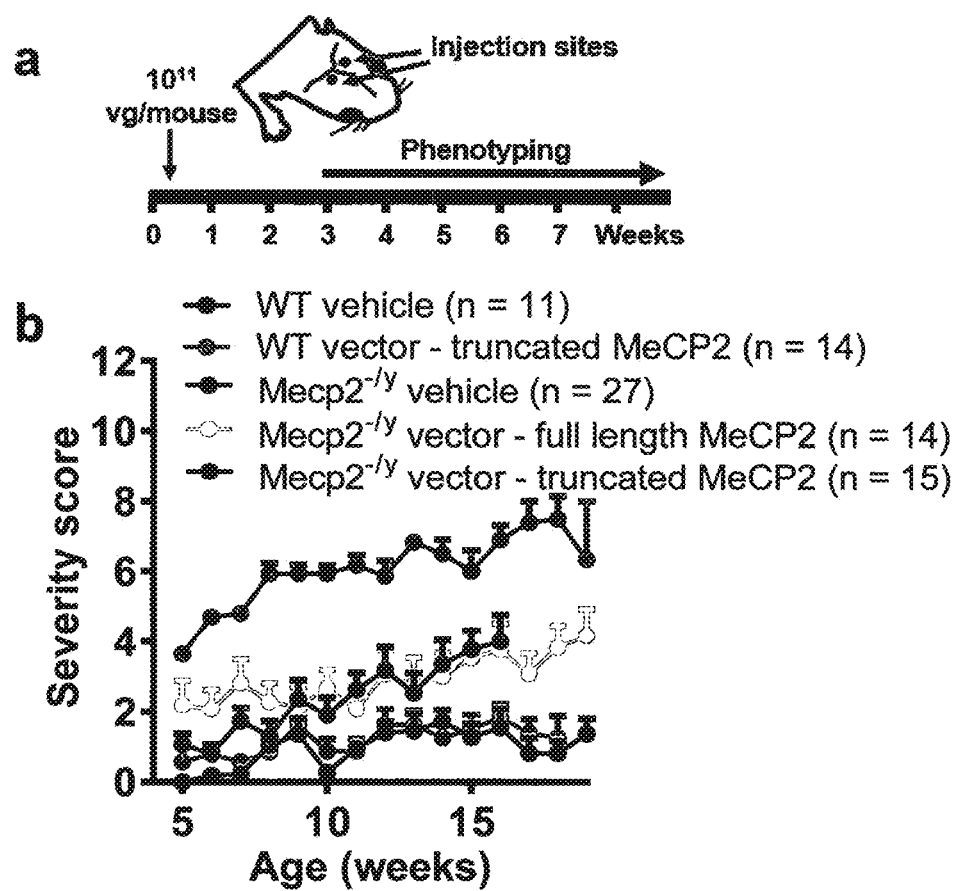

FIG. 17. Direct brain delivery of $2^{nd}$ generation vector to neonatal $Mecp2^{-/y}$ mice revealed a similar therapeutic efficacy of both full-length MeCP2 and ΔNIC protein.

(a) Experimental design. (b) Plot showing mean aggregate severity scores of neonatally treated $Mecp2^{-/y}$ mice (full-length MeCP2 versus ΔNIC protein (truncated MeCP2) compared with vehicle-treated animals. Wild-type mice injected with vector were indistinguishable from vehicle treated mice.

DETAILED DESCRIPTION OF THE INVENTION

Rett Syndrome

Rett syndrome (RTT) is a neurological disorder almost exclusively caused by de novo germline mutations in the X-linked gene, MECP2[1-4]. It is characterized by a constellation of clinical diagnostic and associated features, with symptoms typically becoming overt only 6-18 months postnatally. The phenotype appears to be inherently reversible, as genetic reactivation of silenced Mecp2 in conditional knockout mice results in a robust and enduring reversal of symptoms. However, there are significant challenges to a gene transfer approach, including the requirement to transduce sufficient numbers of neurons in the brain[16] and the avoidance of deleterious overexpression[18].

The present vectors provide viable candidates for treatment of affected individuals, and may even offer the prospect of preventing development of detectable phenotype, if administered to an individual carrying a mutation in the MECP2 gene before symptoms become detectable. Thus treatment may be considered "therapeutic" or "prophylactic". The term "therapy" will be used to refer to inhibition or reversal of established symptoms or phenotype, while "prophylaxis" will be used to refer to inhibiting or preventing development of symptoms in individuals not already displaying overt symptoms. Such individuals will typically have been identified early in life as carrying a loss of function mutation in the MECP2 gene, e.g. by appropriate genetic testing performed before 18 months post partum, e.g. before 12 months or before 6 months post partum.

AAV Vectors

Adeno-associated virus (AAV) is a replication-deficient parvovirus, the single stranded DNA genome of which is about 4.7 kb in length including 145 nucleotide inverted terminal repeats (ITRs). The nucleotide sequence of the AAV serotype 2 (AAV2) genome is presented in Srivastava el al., J Virol, 45: 555-564 (1983) as corrected by Ruffing el al., J Gen Virol, 75: 3385-3392 (1994). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p i9), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3.

Alternative splicing and non-consensus translational start sites are responsible for the production of the three related capsid proteins.

As the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as an expression cassette, with the rep and cap proteins provided in trans. The sequence located between ITRs of an AAV vector genome is referred to herein as the "payload".

The actual capacity of any particular AAV particle may vary depending on the viral proteins employed. Typically, the vector genome (including ITRs) is not more than about 5 kb, e.g. not more than about 4.9 kb, 4.8 kb or 4.7 kb.

The ITRs are each 145 bases in length. Thus, the payload is typically not more than about 4.7 kb, 4.6 kb, 4.5 kb or 4.4 kb in length. Preferably it is not more than 4.4. kb in length. A recombinant AAV (rAAV) may therefore contain up to about 4.7 kb, 4.6 kb, 4.5 kb or 4.4 kb of unique payload sequence.

However, following infection of a target cell, protein expression and replication from the vector requires synthesis of a complementary DNA strand to form a double stranded genome. This second strand synthesis represents a rate limiting step in transgene expression. The requirement for second strand synthesis can be avoided using so-called "self complementary AAV" (scAAV) vectors in which the payload contains two copies of the same transgene payload in opposite orientations to one another, i.e. a first payload sequence followed by the reverse complement of that sequence. These scAAV genomes are capable of adopting either a hairpin structure, in which the complementary payload sequences hybridise intramolecularly with each other, or a double stranded complex of two genome molecules hybridised to one another. Transgene expression from such scAAVs is much more efficient than from conventional rAAVs, but the effective payload capacity of the vector genome is halved because of the need for the genome to carry two complementary copies of the payload sequence.

An scAAV vector genome may contain one or more mutations in one of the ITR sequences to inhibit resolution at one terminal repeat, and consequently increase yield in an scAAV preparation. Thus one of the ITRs in an scAAV may be deleted for the terminal resolution site or may contain an inactivating mutation in the terminal resolution site. See, for example, Wang et al., Gene Therapy (2003) 10, 2105-2111 and McCarty et al., Gene Therapy (2003) 10, 2112-2118. It will therefore be apparent that the two ITR sequences at either end of an AAV genome need not be identical.

scAAVs are reviewed in McCarty, Molecular Therapy, 16(10), 2008, 1648-1656.

In this specification, the term "rAAV vector" is generally used to refer to vectors having only one copy of any given payload sequence (i.e. a rAAV vector is not an scAAV vector), and the term "AAV vector" is used to encompass both rAAV and scAAV vectors.

AAV sequences in the AAV vector genomes (e.g. ITRs) may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11 and AAV PHP.B. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC 001401 and Srivastava et al., *J. Virol.*, 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., *J. Virol.*, 78: 6381-6388 (2004); the AAV-10 genome is provided in *Mol. Ther.*, 13(1): 67-76 (2006); the AAV-11 genome is provided in *Virology*, 330(2): 375-383 (2004); AAV PHP.B is described by Deverman et al., Nature Biotech. 34(2), 204-209 and its sequence deposited under GenBank Accession No. KU056473.1.

It may be desirable to employ AAV-2 ITRs. The scAAV vectors described in the examples below contain AAV-2 ITRs having the sequences (SEQ ID NO: 1):

```
GCGCGCTCGCTCGCTCACTGAGGCCGCCCGGGCAAAGCCCGGGCGTCGGG
CGACCTTTGGTCGCCCGGCCTCAGTGAGCGAGCGAGCGCGCAGAGAGGGA
GTGG
```

And (SEQ ID NO:2):

```
CCACTCCCTCTCTGCGCGCTCGCTCGCTCACTGAGGCCGGGCGACCAAAG
GTCGCCCGACGCCCGGGCTTTGCCCGGGCGGCCTCAGTGAGCGAGCGAGC
GCGC
```

Likewise the proteins present in AAV virion particles of the invention may be derived from any suitable AAV serotype. In general, the vectors are targeted to neural cells, although an ability to transduce glial cells may also be desirable. AAV-9 and AAV PHP.B may be particularly effective at transducing such cell types and so virion proteins, especially capsid (cap) proteins, from AAV-9 or AAV PHP.B may be particularly preferred. The capsid proteins may be pseudotyped to increase specificity or transduction efficiency of the target cell type. These AAV types are also capable of crossing the blood brain barrier, so are particularly appropriate if peripheral administration is required.

Virion particles comprising vector genomes of the invention are typically generated in packaging cells capable of replicating viral genomes, expressing viral proteins (e.g. rep and cap proteins), and assembling virion particles. Packaging cells may also require helper virus functions, e.g. from adenovirus, El-deleted adenovirus or herpesvirus. Techniques to produce AAV vector particles in packaging cells are standard in the art. Production of pseudotyped AAV is disclosed in, for example, WO 01/83692. In various embodiments, AAV capsid proteins may be modified to enhance delivery of the recombinant vector. Modifications to capsid proteins are generally known in the art. See, for example, US 2005/0053922 and US 2009/0202490.

One method of generating a packaging cell is to create a cell line that stably expresses all the necessary components for AAV particle production. For example, a plasmid (or multiple plasmids) comprising an AAV genome lacking AAV rep and cap genes, AAV rep and cap genes separate from the AAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of AAV. Other examples of suitable methods employ adenovirus or baculovirus rather than plasmids to introduce AAV genomes and/or rep and cap genes into packaging cells.

Alternatively, a packaging cell can be generated by simply transforming a suitable cell with one or more plasmids encoding an AAV genome, AAV proteins, and any required helper virus functions. The so-called "triple transfection" method utilises three plasmids each carrying one of these sets of genes. See Grieger et al., Nature Protocols 1(3), 1412-128 (2006) and references cited therein.

General principles of AAV production are reviewed in, for example, Carter, 1992, Current Opinions in Biotechnology, 1533-539; and Muzyczka, 1992, Curr. Topics in Microbial, and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988) and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

Techniques for scAAV production are described by Grieger et al., *Molecular Therapy* 24(2), 287-297, 2016.

The invention thus provides packaging cells that produce infectious AAV virion particles of the invention. In one embodiment packaging cells may be stably transformed cancer cells such as HeLa cells, 293 cells and PerC.6 cells (a cognate 293 line). In another embodiment, packaging cells are cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

MeCP2 Protein

The vectors described in this specification carry an expression cassette encoding methyl CpG binding protein (MeCP2), which is an transcriptional regulator encoded on the X chromosome and highly expressed in neurons, especially in neurons in the brain and CNS. The terms MECP2 and Mecp2 are typically used to refer to the human and murine genes respectively. Although the vectors of the invention are envisaged for use primarily in humans, they may be employed in other species, especially in mouse and other animal models of Rett syndrome. Thus, the terms MECP2 and MeCP2 will be used to refer to genes and proteins from any appropriate species and should not be interpreted as being species-specific unless the context demands.

As discussed above, loss of function mutations in the MECP2 gene are implicated in development of Rett syndrome, primarily in females.

A MeCP2 protein is capable of inducing an increase in survival, an increase in body weight, and/or an increase in RTT-like aggregate severity score in juvenile male MeCP2$^{-/y}$ mice. See Guy et al, Reversal of neurological symptoms in a mouse model of Rett syndrome; Science 315(5815): 1143-1147 (2007).

For the purposes of assessing activity, administration may be via any appropriate route, e.g. via an AAV vector as described in this specification. Improvements are seen as compared to identical control mice given an otherwise identical control treatment lacking functional MeCP2 protein.

Without wishing to be bound by theory, a MeCP2 protein will typically be capable of binding to methylated DNA and of interacting with (e.g. binding to) components of the NCoR/SMRT co-repressor complex. Components of the co-repressor complex include NCoR, HDAC3, SIN3A, GPS2, SMRT, TBL1X and TBLR1. Thus a MeCP2 protein may be capable of recruiting components of the NCoR/SMRT co-repressor complex to methylated DNA.

There are two isoforms of human MeCP2 protein which differ in their N-terminal sequence.

Isoform 1 has the sequence (SEQ ID NO: 3):

MAAAAAAAPSGGGGGGEEERLEEKSEDQDLQGLKDKPLKFKKVKKDKKEE

KEGKHEPVQPSAHHSAEPAEAGKAETSEGSGSA<u>PAVPEASASPKQRRSII</u>

<u>RDRGPMYDDPTLPEGWTRKLKQRKSGRSAGKYDVYLINPQGKAFRSKVEL</u>

<u>IAYFEKVGDTSLDPNDFDFTVTGRGSPSRREQKPPKKPKSPKAPGTGRGR</u>

GRPKGSGTTRPKAATSEGVQVKRVLEKSPGKLLVKMPFQTSPGGKAEGGG

ATTSTQVMVIKRPGRK*RKAEADPQAIPKKRGRK*<u>PGSVVAAAAAEAKKKA</u>

<u>VKSVQETVLPIKKRKTRETVS</u>IEVKEVVKPLLVSTLGEKSGKGLKTCKSP

GRKSKESSPKGRSSSASSPPKKEHHHHHHSESPKAPVPLLPPLPPPPPE

PESSEDPTSPPEPQDLSSSVCKEEKMPRGGSLESDGCPKEPAKTQPAVAT

AATAAEKYKHRGEGERKDIVSSSMPRPNREEPVDSRTPVTERVSS

Isoform 2 has the sequence (SEQ ID NO: 4):

MVAGMLGLREEKSEDQDLQGLKDKPLKFKKVKKDKKEEKEGKHEPVQPSA

HHSAEPAEAGKAETSEGSGSA<u>PAVPEASASPKQRRSII</u>RDRGPMYDDPTL

<u>PEGWTRKLKQRKSGRSAGKYDVYLINPQGKAFRSKVELIAYFEKVGDTSL</u>

<u>DPNDFDFTVTGRGSPSRREQKPPKKPKSPKAPGTGRGRPKGSGTTRPK</u>

AATSEGVQVKRVLEKSPGKLLVKMPFQTSPGGKAEGGGATTSTQVMVIKR

PGRK*RKAEADPQAIPKKRGRK*<u>PGSVVAAAAAEAKKKAVKESSIRSVQET</u>

<u>VLPIKKRKTRETVS</u>IEVKEVVKPLLVSTLGEKSGKGLKTCKSPGRKSKES

SPKGRSSSASSPPKKEHHHHHHSESPKAPVPLLPPLPPPPEPESSEDP

TSPPEPQDLSSSVCKEEKMPRGGSLESDGCPKEPAKTQPAVATAATAAEK

YKHRGEGERKDIVSSSMPRPNREEPVSRTPVTERVSS

Without wishing to be bound by theory, it is believed that the most significant functional regions of the MeCP2 protein are the methyl-CpG binding domain (MBD; underlined), the nuclear localisation signal (NLS; bold italics), and the NCoR/SMRT Interaction Domain (NID; double underlined). Thus, a MeCP2 protein will typically comprise:

(i) a methyl-CpG binding domain (MBD) having the sequence (SEQ ID NO: 5)

PAVPEASASPKQRRSIIRDRGPMYDDPTLPEGWTRKLKQRKSGRSAGKYD
VYLINPQG<u>K</u>AFRSK<u>V</u>ELIAYFEKVGDTSLDPNDFDFTVTGRGSPSRREQK
PP or a variant thereof having at least 70% identity, e.g. at least 75%, 80%, 85%, 90%, 95%, 96%, 97%, 98% or 99% identity thereto;

(ii) a NCoR/SMRT Interaction Domain (NID) having the sequence (SEQ ID NO: 6)

PGSVVAAAAAEAKKKAVKESSIRSVQETVLPIKKRKTRETV or a variant thereof having at least 70% identity, e.g. at least 75%, 80%, 85%, 90%, 95%, 96%, 97%, 98% or 99% identity thereto; and (iii) a nuclear localisation signal (NLS).

Typically, the MBD is able to bind to methylated DNA. It is believed to possess a number of phosphorylation sites which shown in bold font and underlined above. These sites are Ser80, Ser86, Thr148, Ser149 and Ser164, numbered according to their positions in the human isoform 2 sequence.

The NID is typically able to interact with or bind to the NCoR/SMRT co-repressor complex.

The MBD is typically located N-terminal of the NID.

The NLS may be located between the MBD and NID.

The NLS may be the native MeCP2 NLS, having the sequence (SEQ ID NO: 7) RKAEADPQAIPKKRGRK. However, many different NLS sequences are known and NLS sequences apart from the native MeCP2 NLS may be used, such as the SV40 Large T antigen NLS (SEQ ID NO: 8)(PKKKRKV).

Thus the MeCP2 protein may comprise or consist of the sequence (SEQ ID NO: 9):

SEDQDLQGLKDKPLKFKKVKKDKKEEKEGKHEPVQPSAHHSAEPAEAGKA

ETSEGSGSAPAVPEASASPKQRRSIIRDRGPMYDDPTLPEGWTRKLKQRK

SGRSAGKYDVYLINPQGKAFRSKVELIAYFEKVGDTSLDPNDFDFTVTGR

GSPSRREQKPPKKPKSPKAPGTGRGRGRPKGSGTTRPKAATSEGVQVKRV

LEKSPGKLLVKMPFQTSPGGKAEGGGATTSTQVMVIKRPGRKRKAEADPQ

AIPKKRGRKPGSVVAAAAAEAKKKAVKESSIRSVQETVLPIKKRKTRETV

SIEVKEVVKPLLVSTLGEKSGKGLKTCKSPGRKSKESSPKGRSSSASSPP

KKEHHHHHHKSESPKAPVPLLPPLPPPPPEPESSEDPTSPPEPQDLSSSV

CKEEKMPRGGSLESDGCPKEPAKTQPAVATAATAAEKYKHRGEGERKDIV

SSSMPRPNREEPVDSRTPVTERVSS;

or a functional variant thereof having at least 70% identity, e.g. at least 75%, 80%, 85%, 90%, 95%, 96%, 97%, 98% or 99% identity thereto; or a functional fragment of either. Differences from this sequence preferably lie outside the MBD and NID, and a functional NLS should be retained.

A fragment of this sequence, designated ΔNC, which is believed to be functionally equivalent has the sequence (SEQ ID NO: 10):

PAVPEASASPKQRRSIIRDRGPMYDDPTLPEGWTRKLKQRKSGRSAGKYD

VYLINPQGKAFRSKVELIAYFEKVGDTSLDPNDFDFTVTGRFSPSRREQK

-continued
PPKKPKSPKAPGTGRGRGRPKGSGTTRPKAATSEGVQVKRVLEKSPGKLL

VKMPFQTSPGGKAEGGGATTSTQVMIKRPGRRKRKAEADPQAIPKKRGRK

PGSVVAAAAAEAKKKAVKESSIRSVQETVLPIKKRKTRETV

Thus the MeCP2 protein may comprise or consist of the ΔNC sequence or may be a functional variant thereof having at least 70% identity, e.g. at least 75%, 80% 85%, 90%, 95%, 96%, 97%, 98% or 99% identity thereto. Again, differences from this sequence preferably lie outside the MBD and NID, and a functional NLS should be retained.

A further variant, designated ΔNIC, comprising the MBD and NID, and having an alternative NLS sequence (from SV40 large T antigen), but with much of the remaining native MeCP2 sequence deleted, has the sequence (SEQ ID NO: 11):

PAVPEASASPKQRRSIIRDRGPMYDDPTLPEGWTRKLKQRKSGRSAGKYD

VYLINPQGKAFRSKVELIAYFEKVGDTSLDPNDFDFTVTGRGSPSRREQK

PPGSSGSSGPKKKRKVPGSVVAAAAAEAKKKAVKESSIRSVQETVLPIKK

RKTRETV

Thus the MeCP2 protein may comprise or consist of the ΔNIC sequence or may be a functional variant thereof having at least 70% identity, e.g. at least 75%, 80%, 85%, 90%, 95%, 96%, 97%, 98% or 99% identity thereto. Again, differences from this sequence preferably lie outside the MBD and NID, and a functional NLS should be retained.

Where the MBD or NID of the MeCP2 protein contain one or more differences from the reference sequences provided, it may be desirable that those differences are conservative substitutions. It may also be desirable that the phosphorylation sites of the MBD are maintained.

The protein may further comprise an N-terminal portion having the sequence: (SEQ ID NO: 12)MAAAAAAAPSGGGGGGEEERLEEK or MVAGMLGLREEK (SEQ ID NO: 13), Of at least 70%% identity to either, e.g. at least 75%, 80%, 85%, 90%, 95%, 96%, 97%, 98% or 99% identity, to either.

Thus, the MeCP2 protein encoded by the expression cassette may, for example, comprise or consist of one of the sequences:

(human isoform 1)
(SEQ ID NO: 14)
MAAAAAAAPSGGGGGGEEERLEEKSEDQDLQGLKDKPKLFKKVKKDKKEE

KEGKHEPVQPSAHHSAEPAEAGKAETSEGSGSAPAVPEASASPKQRRSII

RDRGPMYDDPTLPEGWTRKLKQRKSGRSAGKYDVYLINPQGKAFRSKVEL

IAYFEKVGDTSLDPNDFDFTVTGRGSPSRREQKPPKKPKSPKAPGTGRGR

GRPKGSGTTRPKAATSEGVQVKRVLEKSPGKLLVKMPFQTSPGGKAEGGG

ATTSTQVMVIKRPGRKRKAEADPQAIPKKRGRKPGSVVAAAAAEAKKKAV

KESSIRSVQETVLPIKKRKTRETVSIEVKEVVKPLLVSTLGEKSGKGLKT

CKSPGRKSKESSPKGRSSSASSPPKKEHHHHHHKSESPKAPVPLLPPLPP

PPPEPESSEDPTSPPEPQDLSSSVCKEEKMPRGGSLESDGCPKEPAKTQP

AVATAATAAEKYKHRGEGERKDIVSSSMPRPNREEPVDSRTPVTERVSS (human isoform 2)

-continued (SEQ ID NO: 15)
MVAGMLGLREEKSEDQDLQGLKDKPLKFKKVKKDKKEEKEGKHEPVQPSA

HHSAEPAEAGKAETSEGSGSAPAVPEASASPKQRRSIIRDRGPMYDDPTL

PEGWTRKLKQRKSGRSAGKYDVYLINPQGKAFRSKVELIAYFEKVGDTSL

DPNDFDFTVTGRGSPSRREQKPPKKPKSPKAPGTGRGRGRPKGSGTTRPK

AATSEGVQVKRVLEKSPGKLLVKMPFQTSPGGKAEGGGATISTQVMVIER

PGRKRKAEADPQAIPKERGRKPGSVVAAAAAEAKKKAVKESSIRSVQETV

LPIKKRKTRETVSIEVKEVVKPLLVSTLGEKSGKGLKTCKSPGRKSKESS

PKGRSSSASSPEKKEHHHHHHHSESPKAPVPLLPPLPPPPPEPESSEDPT

SPPEPQDLSSSVCKEEEMPRGGSLESDGCPKEPAKTQPAVATAATAAEKY

KHRGEGERKDIVSSSMPRENREEPVDSRTPVTERVSS (ΔNC isoform 1)
(SEQ ID NO: 16)
MAAAAAAAPSGGGGGGEEERLEEKPAVPEASASPKQRRSIIRDRGPMYDD

PTLPEGWTRKLKQRKSGRSAGKYDVYLINPQGKAFRSKVELIAYFEKVGD

TSLDENDFDFTVTGRGSPSRREQKPPKKPKSPKAPGTGRGRGRPKGSGTT

RPKAATSEGVQVKRVLEKSPGKLLVKMPFQTSPGGKAEGGGATTSTQVMV

IKRPGRKRKAEADPQAIPKKRGRKPGSVVAAAAAEAKKKAVKESSIRSVQ

ETVLPIKKRKTRETV (ΔNC isoform 2)
(SEO ID NO: 17)
MVAGMLGLREEKPAVPEASASPKQRRSIIRDRGPMYDDPTLPEGWTRKLK

QRKSGRSAGKYDVYLINPQGKLFRSKVELIAYFEKVGDTSLDPNDFDFTV

TGRGSPSRREQKPPKKPKSPKAPGTGRGRGRPKGSGTTRPKAATSEGVQV

KRVLEKSPGKLLVKMPFQTSPGGKAEGGGATTSTQVMVIKRPGRKRKAEA

DPQAIPKKRGRKPGSVVAAAAAEAKKKAVKESSIRSVQETVLPIKKRKTR

ETV (ΔNIC isoform 1)
(SEQ ID NO: 18)
MAAAAAAAPSGGGGGGEEERLEEKPAVPEASASPKQRRSIIRDRGPMYDD

PILPEGWIRKLKQRKSGRSAGKYDVYLINPQGKAFRSKVELIAYFEKVGD

TSLDPNDFDFTVTGRGSPSRREQKPPGSSGSSGPKKKRKVPGSVVAAAAA

EAKKKAVKESSIRSVQETVLPIKKRKTRETV (ΔNIC isoform 2)
(SEQ ID NO: 19)
MVAGMLGLREEKFAVPEASASPKQRRSIIRDRGPMYDDPILPEGWIRKLK

QRKSGRSAGKYDVYLINPQGKAFRSKVELIAYFEKVGDTSLDPNDFDFTV

TGRGSPSRREQKPPGSSGSSGPKKKRKVPGSVVAAAAAEAKKKAVKESSI

RSVQETVLPIKKRKTRETV or may have at least 70% identity, e.g. at least 75%, 80%, 85%, 90%, 95%, 96%, 97%, 98% or 99% identity, to any one of those sequences.

Identity values of at least 80% or at least 90% to the reference sequences provided may be particularly preferred.

It will be apparent to the skilled person that the expression cassette of the invention may also usefully encode MeCP2 proteins from other species, especially other mammalian species, e.g. from a non-human primate, or a domestic, laboratory or livestock animal, such as a rodent (e.g. mouse, rat, guinea pig), lagomorph (e.g. rabbit), cat, dog, pig, cow, horse, sheep, goat, etc.

The MeCP2 protein may additionally comprise heterologous (i.e. non-MeCP2) sequence, e.g. at the C-terminal end of the molecule, such as an epitope tag to aid isolation or identification. Examples include a poly-histidine (e.g. hexa-histidine) tag, FLAG tag, Myc tag, fluorescent proteins such as green fluorescent protein (GFP) and enhanced green fluorescent protein (eGFP), etc. Such heterologous portions are typically no more than 50 amino acids in length, e.g. no more than 20 amino acids in length. For example, the MeCP2 protein encoded by the second generation vector described in the examples below comprises a C-terminal c-Myc epitope tag having the sequence EQKLISEEDL (SEQ ID NO: 20). This protein has the sequence (SEQ ID NO: 21):

MAAAAAAAPSGGGGGGEEERLEEKSEDQDLQGLKDKPLKFKKVKKDKKE

EKEGKHEPVQPSAHHSAEPAEAGKAETSEGSGSAPAVPEASASPKQRRS

IIRDRGPMYDDPTLPEGWTRKLKQRKSGRSAGKYDVYLINPQGKAFRSK

VELIAYFEKVGDTSLDPNDFDFTVTGRGSPSRREQKPPKKPKSPKAPGT

GRGRGRPKGSGTTRPKAATSEGVQVKRVLEKSPGKLLVKMPFQTSPGGK

AEGGGATTSTQVMVIKRPGRKRKAEADPQAIPKKRGRKPGSVVAAAAAE

AKKKAVKESSIRSVQETVLPIKKRKTRETVSIEVKEVVKPLLVSTLGEK

SGKGLKTCKSPGRKSKESSPKGRSSSASSPPKKEHHHHHHHSESPKAPV

PLLPPLPPPPPEPESSEDPTSPPEPQDLSSSVCKEEKMPRGGSLESDGC

PKEPAKTQPAVATAATAAEKYKHRGEGERKDIVSSSMPRPNREEPVDSR

TPVTERVSSRGPF<u>EQKLISEEDL</u>VD where the MeCP2 sequence is underlined and the c-Myc epitope tag is double-underlined.

A c-Myc-tagged version of the ΔNC protein described above may have the sequence (SEQ ID NO: 22):

MAAAAAAAPSGGGGGGEEERLEEKPAVPEASASPKQRRSIIRDRGPMYDD

PTLPEGWTRKLKQRKSGRSAGKYDVYLINPQGKAFRSKVELIAYFEKVGD

TSLDPNDFDFTVTGRGSPSRREQKPPKKPKSPKAPGTGRGRGRPKGSGTT

RPKAATSEGVQVKRVLEKSPGKLLVKMPFQTSPGGKAEGGGATTSTQVMV

IKRPGRKRKAEADPQAIPKKRGRKPGSVVAAAAAEAKKKAVKESSIRSVQ

ETVLPIKKRKTRETVGSSGSSG<u>EQLKISEEDL</u>VD where the MeCP2 sequence is underlined and the c-Myc epitope tag is double-underlined.

A c-Myc-tagged version of the ΔNIC protein described above may have the sequence (SEQ ID NO: 23):

MAAAAAAAPSGGGGGGEEERLEEKPAVPEASASPKQRRSIIRDRGPMYDD

PTLPEGWTRKLKQRKSGRSAGKYDVYLINPQGKAFRSKVELIAYFEKVGD

TSLDPNDFDFTVTGRGSPSRREQKPPGSSGSSGPKKKRKVPGSVVAAAAA

EAKKKAVKESSIRSVQETVLPIKKRKTRETVGSSGSSG<u>EQKLISEEDL</u>VD where the MeCP2 sequence is underlined and the c-Myc epitope tag is double-underlined.

It will be understood that a protein intended for therapeutic use will generally not contain such heterologous elements, to reduce immunogenicity and risk of other side-effects.

In some embodiments, the MeCP2 protein encoded by the expression cassette is not more than 600 amino acids in length, e.g. not more than 550, 540, 530 or 520 amino acids in length. Thus the open reading frame encoding the MeCP2 protein will be not more than 1803 bases in length (including the top codon), e.g. not more than 1653, 1623, 1593 or 1563 bases in length.

Percent (%) amino acid sequence identity between a candidate sequence and the reference sequences presented above is defined as the percentage of amino acid residues in the candidate sequence that are identical with the amino acid residues in the reference sequence, after aligning the sequences and introducing gaps, if necessary, to achieve the optimum alignment, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

A conservative substitution may be defined as a substitution within an amino acid class and/or a substitution that scores positive in the BLOSUM62 matrix.

According to one classification, the amino acid classes are acidic, basic, uncharged polar and nonpolar, wherein acidic amino acids are Asp and Glu; basic amino acids are Arg, Lys and His; uncharged polar amino acids are Asn, Gln, Ser, Thr and Tyr; and non-polar amino acids are Ala, Gly, Val, Leu, Ile, Pro, Phe, Met, Trp and Cys.

According to another classification, the amino acid classes are small hydrophilic, acid/acid amide/hydrophilic, basic, small hydrophobic and aromatic, wherein small hydrophilic amino acids are Ser, Thr, Pro, Ala and Gly; acid/acidamide/hydrophilic amino acids are Asn, Asp, Glu and Gln; basic amino acids are His, Arg and Lys; small hydrophobic amino acids are Met, Ile, Leu and Val; and aromatic amino acids are Phe, Tyr and Trp Substitutions which score positive in the BLOSUM62 matrix are as follows:

The second generation expression cassette described in the examples employs a contiguous stretch of chromosomal sequence from the human MeCP2 gene including a core promoter region, a silencer region upstream of (and slightly overlapping) the core promoter region) and a CNS regulatory element located downstream of the core promote region and upstream of the transcriptional start site. These sequences are illustrated in FIG. 14.

Without wishing to be bound by theory, it is believed that the core promoter and CNS regulatory element ensure adequate expression in neural cells, while the silencer may prevent over-expression and hence toxicity, in both neural cells and in other cell types including glial cells and liver cells.

Thus the 5' transcriptional control region may comprise a core amino acid sequence having the sequence (SEQ ID NO: 24):

```
AAACCAGCCCCTCTGTGCCCTAGCCGCCTCTTTTTTCCAAGTGACAGTAG
AACTCCACCAATCCGCAGCTGAATGGGGTCCGCCTCTTTTCCCTGCCTAA
ACAGACAGGAACTCCTGCCAATTGAGGGCG
``` or a functional fragment thereof, or a variant thereof having no more than 20 nucleotide changes, e.g. no more than 10 or no more than 5 nucleotide changes compared to that sequence, wherein the core amino acid sequence region is capable of initiating transcription in neural cells, e.g. in neurons in the brain and/or CNS, alone or in conjunction with a CNS regulatory element.

The 5' transcriptional control region may comprise a silencer element having the sequence (SEQ ID NO: 25):

```
TTAAGCGCCAGAGTCCACAAGGGCCCAGTTAATCCTCAACATTCAAATGC
TGCCCACAAAAC
``` or a variant thereof having no more than 10 or no more than 5 nucleotide changes compared to that sequence.

The 5' transcriptional control region may comprise a CNS regulatory element having the sequence (SEQ ID NO: 26):

```
         CAGCACACAGGCTGGTCGG.
```

| | Original Residue | | | | | | | | | | | | | | | | | | |
|---|---|---|---|---|---|---|---|---|---|---|---|---|---|---|---|---|---|---|---|
| | C | S | T | P | A | G | N | D | E | Q | H | R | K | M | I | L | V | F | Y | W |
| Substitution | — | T | S | — | S | — | S | N | D | E | N | Q | E | I | M | M | M | Y | H | F |
| | | A | | | | | D | E | Q | R | Y | K | Q | L | L | I | I | W | F | Y |
| | | N | | | | | | H | | K | K | | R | V | V | V | L | | W | |

5' Transcriptional Control Region

The MeCP2 expression cassette comprises a 5' transcriptional control region capable of directing transcription in neural cells, e.g. in neurons, especially of the brain and CNS. It may be desirable that expression also takes place in glial cells, although high levels of expression in glial cells are generally not preferred.

The 5' transcriptional control region comprises a promoter and a transcriptional initiation site. It may also contain other control elements, including enhancer and/or silencer elements.

It may be possible to use a universal promoter such as a viral promoter (e.g. the SV40 promoter) or a mammalian "housekeeping" promoter. Preferably, though, the promoter directs expression preferentially in neural cells as compared to other cell types.

An E-box element (sequence CAGGTG) overlaps the 3' end of the core promoter sequence, and an SP1 site (GGGCGG) is located 3' of the CNS regulatory element. These elements may also be present if desired.

The 5' transcriptional control region may comprise the native MeCP2 core promoter sequence annotated as mMeP426 in FIG. 14.

MicroRNA Binding Sites

The 3'UTR of the MeCP2 expression cassette may contain one or more microRNA (miRNA) binding sites, to facilitate regulation of MeCP2 transgene expression.

MicroRNAs are small non-coding RNAs that have a substantial impact on cellular function through repression of translation (either through inhibition of translation or induction of mRNA degradation). MicroRNAs derive from primary RNA transcripts (pri-miRNA) synthesised by RNA pol II, which may be several thousand nucleotides in length. A single pri-miRNA transcript may give rise to more than one active miRNA.

In the nucleus, the Type III RNAse enzyme Drosha processes the pri-miRNA transcript into a precursor miRNA (pre-miRNA) consisting of a stem-loop or hairpin structure, normally around 70 to 100 nucleotides in length. The pre-miRNA is then transported to the cytoplasm, where it is processed further by the RNAse Dicer, removing the loop and yielding a mature double stranded miRNA molecule, having an active "guide" strand (typically 15 to 25 nucleotides in length) hybridised to a wholly or partially complementary "passenger" strand.

The mature double stranded miRNA is then incorporated into the RNA-induced silencing complex, where the guide strand hybridises to a binding site in the target mRNA.

The guide strand may not be completely complementary to the target binding site. However, a region of the guide strand designated the "seed" sequence is usually fully complementary to the corresponding "core" sequence of the target binding site. The seed sequence is typically 2 to 8 nucleotides in length and located at or near (within 1 or two nucleotides of) the 5' end of the guide strand.

Without wishing to be bound by any particular theory, a miR-22 binding site may regulate MeCP2 expression in peripheral cells. See ref. 32.

A miR-22 binding site typically comprises at least the core sequence:

GGCAGCT.

For example, a miR-22 binding site may comprise the sequence (SEQ ID NO: 27):

ACAAGAATAAAGGCAGCTGTTGTCTCTTC in which the core sequence is underlined;
or may differ therefrom at one or more positions, e.g. at up to 5 positions, up to 10 positions, up to 15 positions or up to 20 positions, all of which must lie outside the core sequence.

A miR-19 binding site may regulate MeCP2 expression in glial cells. See ref. 33.

A miR-19 binding site typically comprises at least the core sequence:

TTTGCAC.

For example, a miR-19 binding site may comprise the sequence (SEQ ID NO: 28):

AGAAGTAGCTTTGCACTTTTCTAAACTAGG in which the core sequence is underlined;
or may differ therefrom at one or more positions, e.g. at up to 5 positions, up to 10 positions, up to 15 positions or up to 20 positions, all of which must lie outside the core sequence.

A miR-124 binding site may also regulate MeCP2 transgene expression in glial cells. See refs. 35 and 44.

A miR-124 binding site typically comprises at least the core sequence:

TGCCTTA.

A miR-124 binding site may comprise further sequences 5' or 3' of the core sequence if desired, but the core sequence will typically not vary.

A miR-132 binding site may regulate MeCP2 expression via a feedback loop with BNDF2 (brain-derived neurotrophic factor 2). MeCP2 is believed to increase expression levels of BNDF2. BNDF2 in turn increases levels of miR132, which is a negative regulator of MeCP2 expression. See ref. 34.

A miR132 binding site typically comprises at least the core sequence:

GACTGTTA.

For example, a miR-132 binding site may comprise the sequence (SEQ ID NO: 29):

AATATCACCAGGACTGTTACTCAATGTGTG in which the core sequence is underlined;
or may differ therefrom at one or more positions, e.g. at up to 5 positions, up to 10 positions, up to 15 positions or up to 20 positions, all of which must lie outside the core sequence.

AU-Rich Element

The 3'UTR of the expression cassette may encode an AU-rich element.

AU-rich elements (AREs) are common regulators of mRNA stability, via the 3'-5' exosome pathway, and are typically located in the 3'UTR.

An AU-rich element may contain one or more repeats of the sequence AUUUA. It may also contain one or more so-called US2B elements, having the sequence AUAUAU.

The 3'UTR of the MeCP2 gene contains an AU-rich element having the sequence AUAUAUUUAAAAA (SEQ ID NO: 30)(ref. 38) and containing one AUUUA repeat and one ES2B element. Variations to this sequence may be possible.

Other Regulatory Signals

The skilled person will be capable of designing other elements of the expression cassette to achieve appropriate expression of the MeCP2 transgene in the desired target cell type.

For example, transcriptional termination and polyadenylation signals will typically be present, to direct cleavage of the primary transcript and polyadenylation of the resulting mRNA. These may comprise "upstream elements" (5' of the cleavage site) and "downstream elements" (3' of the cleavage site).

A common upstream element is typically a hexamer located 10 to 30 nucleotides upstream of the cleavage site, and often referred to simply as a polyadenylation or poly(A) signal. The MeCP2 gene has two polyadenylation signals of which the sequence of the distal polyadenylation signal (UAUAAA) may be preferred. The sequence AAUAAA is also a commonly used polyadenylation signal.

A downstream element may be a U-rich or GU-rich element. These may contain binding sites for components of the polyadenylation machinery such as CstF (cleavage stimulation factor). The MeCP2 gene contains a GU-rich region having the sequence (SEQ ID NO: 31) UGUCCGUUUGUGUCUUUUGUUGU and containing two CstF binding sites each having the sequence UUUGU.

It will be understood that U (uridine) is referred to in the context of RNA sequences. Corresponding DNA sequences, e.g. as found in an AAV vector genome, will incorporate T instead.

The expression cassette will typically also contain a translational initiation signal, e.g. a Kozak sequence. The Kozak sequence includes the initiation codon for the MeCP2 protein, typically AUG. An example of a suitable Kozak sequence, used in the vectors described in the Examples below, is AAACC<u>AUG</u>G, where the initiation codon is underlined.

The native Kozak sequence from the human MECP2 gene has the sequence AAA<u>AUG</u>G, i.e. it lacks the CC doublet present in the vectors described below. The CC doublet was introduced to provide better conformity with the generally recognised consensus Kozak sequence and hence increase the strength of the Kozak sequence. However, given that high levels of MeCP2 expression can be deleterious, at least in some tissues, it may be desirable in some instances to use the native Kozak sequence rather than the modified sequence.

The skilled person will be aware that considerable variation within the Kozak sequence is possible and will be able to select further alternative sequences as appropriate.

Pharmaceutical Compositions and Routes of Administration

The nucleic acids, virions, etc. described herein can be formulated in pharmaceutical compositions.

Administration may be peripheral, e.g. intravenous, cutaneous or subcutaneous, nasal, intramuscular or intraperitoneal, or direct to the central nervous system (CNS), e.g. by intrathecal injection or intra-cranial injection.

Intravenous and intrathecal administration may be preferred.

Pharmaceutical compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration.

For intravenous, cutaneous or subcutaneous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Compositions for direct administration to the CNS are typically minimal compositions lacking preservatives and other excipients, and may be specially prepared at the time of administration.

Administration is preferably in a "prophylactically effective amount" or a "therapeutically effective amount" (as the case may be), this being sufficient to show benefit to the individual. The actual amount administered, and rate and time-course of administration, may depend on the individual subject and the nature and severity of their condition. Prescription of treatment, e.g. decisions on dosage etc., is within the responsibility of medical practitioners and other medical doctors, and typically takes account of the disorder to be treated, the condition of the individual patient, the site of delivery, the method of administration and other factors known to practitioners.

Examples of the techniques and protocols mentioned above can be found in Remington's Pharmaceutical Sciences, 20th Edition, 2000, pub. Lippincott, Williams & Wilkins.

EXAMPLES

Dose Escalation with AAV/MECP2 Revealed a Narrow Therapeutic Window Following Systemic Administration.

Figure 1:
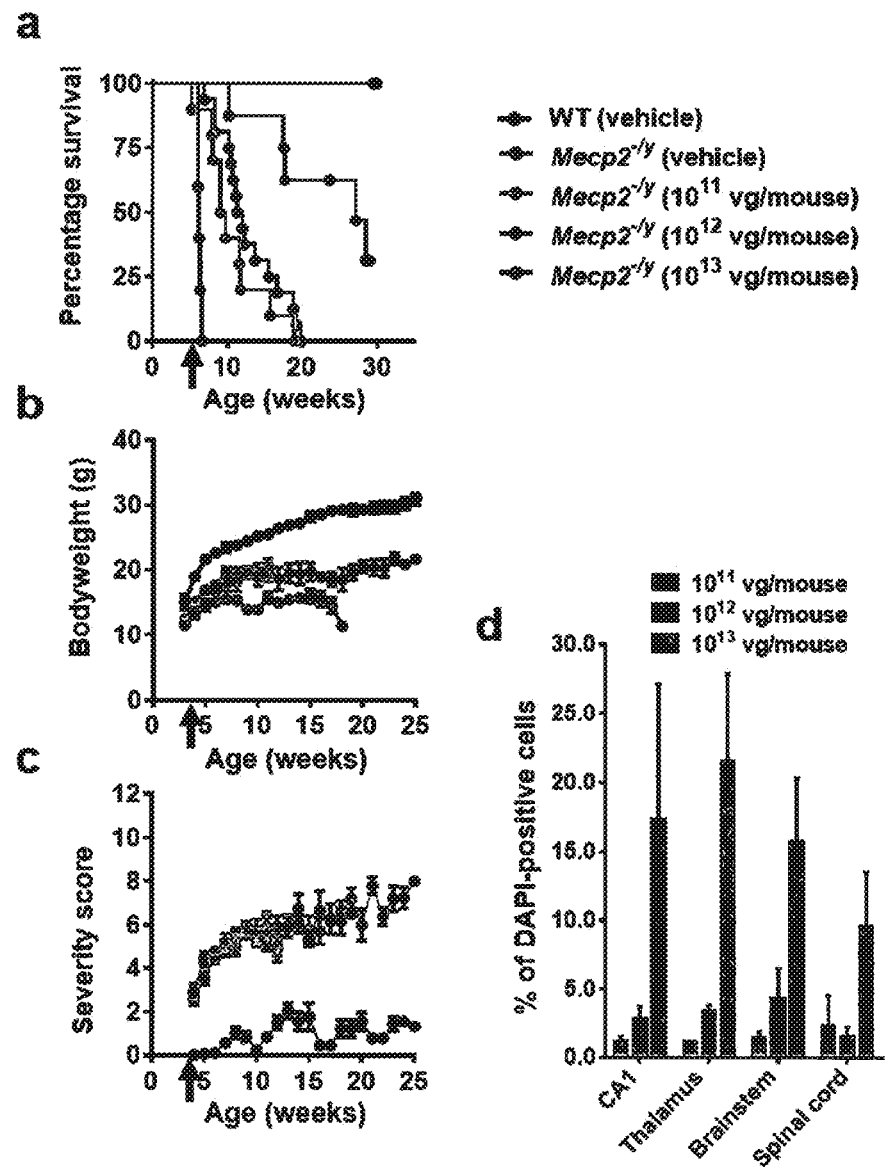
FIG. 1. Systemic delivery of the $1^{st}$ generation vector to Mecp2$^{-/y}$ mice revealed therapeutic efficacy and a narrow therapeutic window.

In order to explore the relationship between vector dose and therapeutic benefits, we conducted a dose escalation experiment in which an scAAV2/9 vector was used to deliver a Myc-tagged human MECP2_e1 cDNA under the control of a short, 229 bp region of the murine Mecp2 endogenous core promoter (MeP229)[19, 22], henceforth referred to as the '1$^{st}$ generation vector'. Juvenile male Mecp2$^{-/y}$ and wild-type (WT) mice were injected at the age of 4-5 weeks into the tail vein either with vehicle or with $1\times10^{11}$ (low dose), $1\times10^{12}$ (moderate dose) or $1\times10^{13}$ (high dose) viral genomes (vg) per mouse (dose range ~$1\times10^{13}$-$1\times10^{15}$ vg/kg). As expected from previous studies of this knockout line[6, 7, 15], onset of RTT-like phenotypic signs in vehicle control-treated[15] Mecp2$^{-/y}$ mice was observed from 4-5 weeks of age and severity progressively increased until death or censoring of all mice by 20 weeks of age (FIG. 1a-c). Mecp2$^{-/y}$ mice treated with the low dose were undistinguishable from vehicle-injected mice in terms of survival, bodyweight and severity score (FIG. 1a-c). In contrast, Mecp2$^{-/y}$ mice treated with the moderate dose ($1\times10^{12}$) showed significantly increased survival and bodyweight compared to the vehicle controls (median survival=27.3 weeks vs 11.64 weeks, p=0.001, Mantel-Cox test, FIG. 1a; p<0.05 for mean bodyweight measured at 11 weeks of age, the median survival for the control Mecp2$^{-/y}$ mice, FIG. 1b). However, there was no difference in the RTT-like phenotype severity score at this dose (FIG. 1c). Finally, the cohort receiving the highest dose showed acute toxicity and lethality at 10-15 days post-injection (FIG. 1a).

Patterns of transduction in treated Mecp2$^{-/y}$ mice were assessed within the CNS by anti-Myc antibody immunofluorescence labeling (FIG. 8), which revealed exogenous MeCP2 protein expression distributed in a punctate pattern within cell nuclei corresponding to that observed for endogenous MeCP2 in WT mice. Samples from the low dose cohort revealed low transduction efficiencies across brain regions (0.5 to 1%). The moderate dose resulted in ~3-5% transduction efficiency, whereas the efficiency for the high dose was 10-22% (FIG. 1d).

In order to measure cellular levels of exogenous MeCP2 relative to native levels, WT mice were treated with vector as above. The low and moderate doses were tolerated and had no observable effect on bodyweight or phenotypic severity score (FIG. 9a-c). However, WT mice treated with the high dose exhibited the acute toxicity and rapid lethality observed in the knockout mice (FIG. 9a-c). Quantification of cellular levels of MeCP2 in mice given this high dose revealed that transduced hippocampal pyramidal cells expressed exogenous MeCP2 at a mean level equivalent to 120% of the endogenous level, resulting in total cellular levels of MeCP2 just over 2-fold higher than normal for these cells (FIG. 9d-f).

Systemic Delivery of 1$^{st}$ Generation Vector Resulted in Liver Toxicity.

To further investigate toxic effects encountered after systemic injection of the 1$^{st}$ generation vector at high doses, levels of exogenous MeCP2 expression were tested in a range of peripheral tissues. Immunohistochemistry revealed that the proportion of Myc-positive cells in the liver was high (FIG. 10). Endogenous MeCP2 levels are known to be much lower in liver cells than in brain neurons[23, 24] and are typically below detection threshold for immunohistochemistry using available antibodies (FIG. 10a). However, exogenous MeCP2 levels in a subset of liver cells (using anti-Myc-immunolabelling) of treated WT mice were found to be higher than MeCP2 levels seen in neurons (FIG. 10b-c) and were thus ~20 times higher than levels found endogenously in such cells. Myc-positive cells were detected also in the heart, kidney and other peripheral tissues in treated Mecp2$^{-/y}$ mice (data not shown).

Histological investigation of liver sections from mice injected with vehicle or low dose of the vector showed largely normal liver structure with occasional areas of mononuclear infiltration (FIG. 2a-b). In contrast, mice injected with higher doses of the vector showed a dose-dependent increase in pathological features including cellular destruction and vacuolation, loss of hepatocytes and mononuclear cell infiltration (FIG. 2c-d).

To address whether the observed liver pathology was due to the high copy number of viral particles per se or was a consequence of MeCP2 overexpression, we injected mice with a vector driving expression of GFP, but otherwise identical to the 1$^{st}$ generation vector. Despite detection of widespread GFP expression in the liver (FIG. 2e), histological examination of liver sections revealed no evidence of cellular damage or immune cell infiltration (FIG. 2f). In addition, no changes in RTT aggregate severity score were observed with this vector (data not shown).

Systemic Administration of 1$^{st}$ Generation Vector Improves Survival in Mecp2[T158M] Knock-in Mice.

An important question for gene transfer in RTT is whether the presence of endogenous mutant MeCP2 might reduce the therapeutic effect of exogenous MeCP2. Male mice expressing native MeCP2 tagged with GFP as a fusion protein and harboring the common RTT-causing p.T158M mutation, Mecp2$^{T158M/y}$ [9], display a phenotype very similar to that of Mecp2-null mice (FIG. 11) but with somewhat enhanced survival (median survival of 20.3 weeks and 12.4 weeks, respectively; p=0.0016, Mantel-Cox test).

Intravenous delivery of a moderate dose ($1\times10^{12}$ vg/mouse) of the 1$^{st}$ generation vector to 4-5 week old Mecp2$^{T158M/y}$ mice resulted in significantly increased survival (FIG. 3a; median survival=38.3 weeks in vector-treated mice vs 20.3 weeks in vehicle-treated mice; p=0.0019, Mantel-Cox test, n=8-15 per group). There was a modest increase in bodyweight in the vector-treated cohort (FIG. 3b; p<0.05, one-way ANOVA using data at 20 weeks of age). However, there was no difference in RTT-like aggregate severity score between groups (FIG. 3c), consistent with a low brain transduction efficiency (~2-4%) as revealed by anti-Myc labelling (FIG. 3d).

The p.T158M mutation affects the chromatin binding capacity of MeCP2, leading to loss of the punctate element of MeCP2 labelling in the nucleus (FIG. 4a)[9]. Immunolabeling of hippocampal neurons from treated Mecp2$^{T158M/y}$ mice showed WT patterns of MeCP2 expression, with restored localization to DAPI bright spots, only in transduced (Myc-positive) cells (FIG. 4b). This is consistent with exogenous MeCP2 being able to localize normally to heterochromatin, despite the presence of mutant endogenous MeCP2 protein within the same nucleus.

Development of a 2$^{nd}$ Generation Vector that Reduced Liver Toxicity after Systemic Administration In light of the data described above, it was evident that a higher AAV vector dose is required to achieve therapeutically relevant levels of brain transduction after systemic delivery. However, severe toxicity after delivery of high doses of our 1$^{st}$ generation cassette necessitated a new design. We tested a range of modifications to the expression cassette and capsid that were predicted to result in lower cellular expression levels and/or reduce liver tropism. This included the use of expression cassettes utilizing (1) an alternative, compact, and presumably weaker, JeT promoter[25], (2) a short synthetic polyadenylation (SpA) signal[26], FIG. 12a), and (3) the original 1$^{st}$ generation expression cassette packaged in a scAAV9.47 capsid, which emerged from an in vivo screen for liver de-targeted capsid sequences relative to AAV9[27, 28]. Systemic injection of these vectors at the moderate dose ($1\times10^{12}$ vg/mouse) into 4-5 week old Mecp2$^{-/y}$ mice resulted in significantly extended survival and improved bodyweight but there was no impact on the RTT-like aggregate severity score (FIG. 12b). In summary, none of these modifications resulted in any significant improvements over the 1$^{st}$ generation vector (p>0.05 for all measures; ANOVA and Mantel Cox tests). Importantly, these modified vectors all caused the development of liver pathology similar to that observed with the first generation vector (as previously shown in FIG. 2; FIG. 12c).

The rationale for using an endogenous Mecp2 core promoter fragment (MeP229) in the 1$^{st}$ generation vector was that it had been shown largely to recapitulate the endogenous tissue-level pattern of MeCP2 expression[22]. However, this core promoter fragment is missing a number of predicted upstream regulatory elements that may be important in cell-type specific regulation of MeCP2 expression[29-11]. Therefore, we designed a 2nd generation vector (v2) in which we used an extended promoter fragment (MeP426) incorporating additional promoter regulatory elements and a putative silencer element (FIG. 13). We predicted that this might better enable the regulation of exogenous MeCP2 levels in transduced cells. In addition to the extended promoter, we also incorporated a novel 3'-UTR consisting of a fragment of the endogenous MECP2 3'UTR together with a selected panel of binding sites for miRNAs known to be involved in regulation of Mecp2[32-35] (FIG. 13).

In order to test the therapeutic efficacy of the 2$^{nd}$ generation vector, a moderate dose ($1\times10^{12}$ vg/mouse) was injected intravenously into 4-5 week old Mecp2$^{-/y}$ mice. There was a significant extension of survival in the vector-treated compared to the vehicle-treated mice (median survival=29.9 weeks and 11.6 weeks, respectively; p<0.0001, Mantel-Cox, FIG. 5b). There was also significant improvement in bodyweight at the age of 11 weeks (p<0.05, one-way ANOVA, with Tukey's post-hoc pairwise comparison test, FIG. 5c). In contrast, there was no effect on RTT-like aggregate severity score (FIG. 5d). The 2$^{nd}$ generation vector thus showed no therapeutic advantages over the 1$^{st}$ generation vector after systemic delivery (FIG. 5b-d).

In order to compare this vector head-to-head with the 1$^{st}$ generation vector in terms of liver safety, mice were injected intravenously with either 1$^{st}$ or 2$^{nd}$ generation vector at a dose of $1\times10^{12}$ vg/mouse. These mice were sacrificed after 30 days and tissues analysed for exogenous MeCP2 expression (using anti-Myc tag antibody) and signs of liver pathology (FIG. 6). There was no significant difference in transduction efficiency between vector constructs (FIG. 6b), but cellular levels of exogenous MeCP2 (anti-Myc) in mice treated with 1$^{st}$ generation vector were significantly higher than those in mice treated with 2$^{nd}$ generation vector (FIG. 6c; p<0.001, unpaired t-test). Analysis of the distribution of cellular MeCP2 expression levels in transduced cells showed that MeCP2 expression was more tightly regulated in mice injected with the 2nd generation vector (FIG. 6d), with fewer cells exhibiting very high expression levels. Moreover, there was none of the disrupted hepatic architecture or vacuolation previously observed with the $1^{st}$ generation vector (FIG. 6e). The density of inflammatory foci was significantly higher in liver samples from mice injected with $1^{st}$ generation vector than those injected with the $2^{nd}$ generation vector (FIG. 6f).

Neonatal Cerebroventricular Injection of the $2^{nd}$ Generation Vector Improved RTT-Like Aggregate Severity Score The lack of impact on the phenotype after systemic administration is consistent with the low brain transduction efficiencies observed, as it has been established that phenotype severity and degree of improvement after gene restoration correlate with the proportion of MeCP2-expressing cells in the brain[16]. We therefore decided to test the $2^{nd}$ generation vector by direct cerebroventricular injection in mouse neonates, a delivery route that is known to afford widespread transgene expression[19]. When delivered at a dose of $1 \times 10^{11}$ vg/mouse (FIG. 7a), there was a pronounced extension in the survival of Mecp2$^{-/y}$ mice treated with the $2^{nd}$ generation vector in comparison to vehicle-treated mice (median survival=38.5 and 12.4 weeks, respectively; p<0.0001, Mantel-Cox test, FIG. 7b). Whilst there was a negligible effect of vector on bodyweight (FIG. 7c), an important observation was the clear improvement in the RTT-like aggregate severity score compared to vehicle-treated Mecp2-null mice (FIG. 7d). Exogenous MeCP2 (revealed by anti-Myc tag immunolabelling) was detectable in all brain regions, with transduction efficiencies across brain regions ranging from ~10-40% (FIG. 7e-f). Distribution analysis revealed that the modal cellular MeCP2 level in transduced cells in cortex was approx. twice that of endogenous MeCP2 (consistent with an exogenous expression level equal to the endogenous level), with some cells expressing higher levels of exogenous MeCP2 (FIG. 7g). The ΔNIC protein described above was shown to yield comparable results to the full length MeCP2 protein (FIG. 17).

Discussion

The reversal of a wide range of RTT-like phenotypes in mice following delayed unsilencing of Mecp2 provides a strong rationale for gene transfer as a therapeutic strategy in RTT[15, 16]. There are likely to be a variety of barriers to translational success that will need to be identified and addressed in order to secure optimal outcomes in human clinical trials. In the current study, we identified particular challenges associated with systemic delivery of a MECP2-bearing gene therapy vector in terms of a narrow therapeutic window driven by low brain transduction efficiency and the appearance of peripheral overexpression toxicity upon further dose escalation. However, peripheral overexpression can be reduced by refining the cassette design. We show that direct brain delivery of vector in neonatal mice can achieve therapeutically relevant levels of transduction that result in phenotype amelioration. We also show that the vector has similar effectiveness in mice expressing the most common RTT-causing mutation suggesting that the presence of existing mutant forms of MeCP2 is unlikely to be an obstacle to translational success. These results are consistent with experiments in transgenic mice expressing both mutant and WT forms of the protein[36].

Recent attempts to deliver MECP2 exogenously in mouse models of RTT used widely varying vector doses but are difficult to compare based on additional differences in cassette design and other variables including viral production, dosing protocol and phenotype measures[19-21]. In the current study, we used our previously published cassette design (human MECP2_e1 under the control of a MeP229 core promoter fragment),[19] to directly investigate the effect of dose in terms of efficacy and safety. A notable finding was the overall lack of efficacy across the range of doses tested in terms of an effect on RTT-like phenotype severity score. This is not due to such phenotypes being inherently resistant to reversal[15, 16] but is instead most likely explained by the low levels of brain transgene expression afforded by this route of delivery. In contrast to the phenotype severity score, there was a clear dose-response relationship for survival, with the intermediate dose causing a modest increase in mean bodyweight and a significant extension in survival. It is not clear whether the survival and bodyweight effects are due to sufficient (if low) transduction levels in critical brain regions or to expression of MeCP2 in peripheral tissues relevant to mortality. Recent evidence suggests that MeCP2 levels in peripheral tissues can subtly affect bodyweight[23] and it is possible that this may indirectly affect survival measures, as we are obliged to use acute loss of bodyweight as an end-point criterion. Another potential explanation is that we were underestimating levels of transduction efficiency related to survival based on the sensitively of our immunohistochemical detection. However, vector biodistribution validation using qPCR was consistent with our measurements, confirming very modest transduction following systemic delivery. Only the highest dose tested produced appreciable levels of brain transduction (>10-20%), and, unfortunately, the severe liver pathology and lethality associated with this does precluded assessment of the potential for brain specific therapeutic effects in this situation. Liver cells normally express relatively low levels of MeCP2 compared to neurons[23] and identical doses of a GFP-expressing vector were not toxic, so the dose-dependent liver pathology is likely be attributed to the overexpression of exogenous MeCP2.

Our initial attempts to lower toxic MeCP2 expression and/or reduce liver tropism involved modifications to the expression cassette and capsid. However, the use of putative weaker synthetic promoters and polyadenylation signals were not sufficient to avoid liver toxicity. Surprisingly, the use of an AAV9.47 capsid, which is purported to de-target the liver relative to AAV9[27, 28], resulted in liver pathology similar to that seen with AAV9. We therefore focused efforts on a 2nd generation vector, whose design was based on the inclusion of endogenous regulatory elements that may better regulate levels of exogenous MeCP2 in transduced cells. This included the incorporation of an extended endogenous promoter and an endogenous 3'-UTR fragment. Studies analyzing the well-conserved human MECP2 and mouse Mecp2 promoter regions indicated the presence of a number of putative regulatory elements within a 1 kb window immediately upstream of the transcription start site[29-11]. Consequently, our extended endogenous promoter (426 bp) in the 2nd generation vector comprised a putative silencer element at position −274 to −335, with respect to the RefSeq transcription start site (FIG. 13).

An endogenous 3'-UTR was also incorporated, containing the distal MECP2 polyadenylation signal and a number of clustered putative regulatory elements[37-39]. In addition, we performed an analysis of miRNA binding sites in the 3'-UTR of MECP2 using a number of bioinformatic tools[40-42] and incorporated a compact sequence containing binding sites of three highly conserved miRNAs known to be involved in regulation of MeCP2 in the brain; miR-22[43], miR-19[44] and miR-132[34]. Combined, these modifications significantly reduced MeCP2 expression in the liver with subsequent reduction of the hepatotoxicity encountered with the $1^{st}$ generation vector. The relative importance of different modifications (elements within the extended promoter and novel 3'-UTR) were not investigated. However, the efficacy of both vectors after systemic injection of moderate doses was not significantly different. The important advantage of the $2^{nd}$ generation vector is the lack of prominent liver pathology at a dose that provides some therapeutic benefit (i.e. $1\times10^{12}$ vg/mouse). The improved survival after systemic injection, despite low brain transduction efficiency, could be due to restoration of MeCP2 levels in sufficiently numerous critical cells in the brain, or due to restoration in important peripheral tissues. Targeting more cells in the brain through direct brain injection in mouse neonates, along with potentially greater impact via earlier intervention, led to pronounced survival enhancement at a dose ($1\times10^{11}$ vg/mouse) approximately equivalent to the $10^{12}$ systemic dose. Delivery by this direct brain injection route was associated with an improvement in bodyweight but, importantly, also with an improvement in RTT-like phenotype score. The improvement was not as profound as that reported in genetic reversal experiments[16] and this is likely to be due to the combined effects of (1) the relative inefficiency of MeCP2 re-expression across the brain (10-40%) compared to genetic reversal experiments (up to 90%) and (2) the possible deleterious counteracting effects of overexpressing MeCP2 in a proportion of transduced cells.

Analysis of MeCP2 levels indeed indicates a significant pool of cells overexpressing MeCP2, presumably transduced with multiple copies of vector delivering MECP2. This may also account for the slightly elevated severity score in vector-treated WT mice (FIG. 7d) in the form of mild hindlimb clasping. Overall, the proof-of-concept experiments involving direct brain delivery in neonatal mice suggest that if transduction efficiency across the brain can reach sufficiently high levels, then a behavioral improvement is conferred by this vector design.

Conclusion

The results of the current study highlight the challenges associated with both systemic and direct brain delivery of MECP2. The findings suggest that achieving widespread brain expression, whilst at the same time maintaining cell-type appropriate control of MeCP2 levels, will be essential requirements for the successful development of a translational therapy. The development of expression cassettes capable of producing effective and sub-toxic levels of MeCP2 may overcome issues of cellular overexpression and enable direct delivery via the cerebrospinal fluid compartment. Whilst AAV9 appears to be insufficiently efficient in terms of brain transduction after systemic delivery of MECP2 to achieve the desired therapeutic benefit, combining the safer $2^{nd}$ generation cassette together with capsids with improved brain penetrance[45] may effectively pair effective CNS gene transfer with safe levels of peripheral MeCP2 transgene expression. Such a combination would hold enhanced translational promise.

Material and Methods

Animals

All experiments were carried out in accordance with the European Communities Council Directive (86/609/EEC) and with the terms of a project license under the UK Scientific Procedures Act (1986). The Mecp2-null, $Mecp2^{tm1.1Bird}$ and $Mecp2^{T158M}$ mice, originally provided as a kind gift from Professor Adrian Bird, were maintained on a C57BL/6 background. Animals were maintained on 12-hour light/dark cycles with free access to normal mouse food. Mice were genotyped as described previously[9, 15].

Viral Vector Preparation.

Recombinant AAV vector particles were generated at the UNC Gene Therapy Center Vector Core facility. Self-complementary AAV (scAAV) particles (AAV2 ITR-flanked genomes packaged into AAV9 or AAV9.47 serotype capsids) were produced from suspension HEK293 cells transfected using polyethyleneimine (Polysciences, Warrington, PA) with helper plasmids (pXX6-80, pGSK2/9) and a plasmid containing the appropriate ITR-flanked transgene construct. All MeCP2-expressing constructs utilized the human MECP2_e1 coding region with a C-terminal Myc epitope tag unless stated otherwise. Virus production was performed as previously described 46 and the vectors were prepared in a final formulation of high-salt phosphate-buffered saline (PBS; containing 350 mmol/l total NaCl) supplemented with 5% sorbitol.

scAAV Vector Injection and Mouse Phenotyping.

Frozen scAAV9 viral particle aliquots were thawed and diluted to 100 µl in PBS/350 mmol/l NaCl containing 5% sorbitol. Control injections were made using the same diluent lacking vector ('vehicle control'). For direct brain injection into mouse neonates, littermates were sexed at birth and direct bilateral injections of virus (3 µl per site) were delivered into the neuropil of unanaesthetised P0-3 males, as described previously[19]. The injected pups were returned to the home cage containing their non-injected female littermates. Genotyping was carried out at 3 weeks, at which time phenotyping was initiated. For injection into juvenile male mice, injections were made via the tail vein at 4-5 weeks of age. Following injection, all mice were weighed weekly. Phenotyping was carried out, blind to genotype and treatment, twice a week. Mice were scored on an aggregate severity scale using an established protocol (mice were scored for RTT-like phenotypes, comprising mobility, gait, breathing, hindlimb clasping, tremor and general condition; 15, 16, 19, 21. For survival analysis, mice were censored after natural death or if bodyweight losses exceeded 20% of peak bodyweight.

Immunohistochemistry

Mice were anaesthetized with pentobarbitone (50 mg, intraperitoneally) and transcardially perfused with 4% paraformaldehyde (0.1 mol/l PBS). A vibrating microtome (Leica VT1200; Leica, Milton Keynes, UK) was used to obtain 80 µm sections of brain, spinal cord, and liver. Sections were washed three times in 0.3 mol/l PBS and were then transferred to 10 mM sodium citrate (pH 6, 85° C., 30 minutes) for antigen retrieval. Sections were then incubated in the blocking solution (5% normal goat serum in 0.3 mol/l PBS with 0.3% Triton X-100) for 1 hour at room temperature. Samples then were incubated for 48 hours on a shaker at 4° C. with the following primary antibodies: rabbit anti-Myc (Abcam, ab9106); mouse monoclonal anti-MeCP2 (Sigma, WH0004204M1), chicken anti GFP, Abcam ab13970). The primary antibodies were then washed off (3×0.3 mol/l PBST) and secondary antibodies applied to the sections overnight at 4° C.: Alexa fluor 488 goat anti-mouse/rabbit (Invitrogen, Carlsbad, CA; 1/500), Alexa fluor 546 goat anti-mouse/rabbit (Invitrogen; 1/500), Alexa fluor 649, Goat anti mouse (Jackson immunoresearch, 112-495-003JIR). Finally, sections were incubated with 4',6-diamidino-2-phenylindole (DAPI) nuclear stain (Sigma, Poole, UK; 1/1,000) for 30 minutes at room temperature before mounting with Vectashield (Vector labs, Peterborough, UK).

Hematoxylin and Eosin (H&E) Staining

Liver samples were rinsed with 0.1 mol/l PBS then dehydrated through ascending grades of ethanol and cleared in amyl acetate using an automated tissue processor. Specimens were embedded in paraplast and sections (10 μm thick) were collected on APES (aminopropyltriethoxysilane) coated slides and dried overnight in the oven at 37° C. Sections were then deparaffinised through two changes of Histo-clear (Agar Scientific, UK) for 15 min and rehydrated through descending grades of alcohol (100%, 90%, and 70%). The sections were stained with Mayer's hematoxylin for 8 min and then rinsed using tap water. The nuclei were stained blue by placing the slides into Scott's solution for 1 min and then rinsed using tap water. Sections were then stained with 1% eosin for 2 min and washed by water. Finally, the sections were dehydrated through ascending grades of alcohol and histoclear before being mounted with DPX. Images were captured using an AxioCam MRc (Zeiss, Germany) mounted on a light microscope (Zeiss, Germany).

Image Analysis

Analysis of expression patterns, transduction efficiency, and quantification of exogenously derived MeCP2 levels within nuclei was carried out on image stacks captured using a Zeiss LSM710 or Zeiss Axiovert LSM510 laser confocal microscope (Zeiss, Cambridge, UK). Z-series were taken at 1 μm intervals through the section of interest using a 40× objective. To estimate transduction efficiency, images were captured as above and the ratio of Myc-immunopositive nuclei to DAPI-stained nuclei was calculated for random fields (n=12 images/region: 4 images from each of three mice) from sections of hippocampus (CA1 region), layer 5 of primary motor cortex, thalamus, hypothalamus, brainstem, and striatum. To quantify levels of exogenously derived MeCP2 per nucleus in WT mice, confocal stacks (20 μm thick) were obtained as above and ImageJ software (http://rsbweb.nih.gov/ij/) was used to determine mean MeCP2-channel fluorescence intensity within transduced (Myc +ve) and non-transduced (Myc −ve) cells. Fluorescence in the DAPI channel was used to define the nuclear boundary.

Statistical Analysis

Tests for differences between treatment groups were carried out in GraphPad PRISM using one-way ANOVA, Student's t-test, and Mantel-Cox test (survival curves), as appropriate. $p<0.05$ was used to define statistical significance. In multi group comparisons, multiple testing correction for pairwise tests amongst groups was applied using Tukey's post-hoc analysis.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

The teaching of all references in the present application, including patent applications and granted patents, are herein fully incorporated by reference. Any patent application to which this application claims priority is incorporated by reference herein in its entirety in the manner described herein for publications and references.

For the avoidance of doubt the terms 'comprising', 'comprise' and 'comprises' herein is intended by the inventors to be optionally substitutable with the terms 'consisting of', 'consist of', and 'consists of', respectively, in every instance. The term "about" (or "around") in all numerical values allows for a 5% variation, i.e. a value of about 1.25% would mean from between 1.19%-1.31%.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the measurement, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Neul, J L, Kaufmann, W E, Glaze, D G, Christodoulou, J, Clarke, A J, Bahi-Buisson, N, et al. (2010). Rett syndrome: revised diagnostic criteria and nomenclature. *Ann Neurol* 68: 944-950.

2. Amir, R E, Van den Veyver, I B, Wan, M, Tran, C Q, Francke, U, and Zoghbi, H Y (1999). Rett syndrome is caused by mutations in X-linked MECP2, encoding methyl-CpG-binding protein 2. *Nat Genet* 23: 185-188.
3. Bienvenu, T, and Chelly, J (2006). Molecular genetics of Rett syndrome: when DNA methylation goes unrecognized. *Nat Rev Genet* 7: 415-426.
4. Lyst, M J, and Bird, A (2015). Rett syndrome: a complex disorder with simple roots. *Nat Rev Genet* 16: 261-275.
5. Chen, R Z, Akbarian, S, Tudor, M, and Jaenisch, R (2001). Deficiency of methyl-CpG binding protein-2 in CNS neurons results in a Rett-like phenotype in mice. *Nat Genet* 27: 327-331.
6. Guy, J, Hendrich, B, Holmes, M, Martin, J E, and Bird, A (2001). A mouse Mecp2-null mutation causes neurological symptoms that mimic Rett syndrome. *Nat Genet* 27: 322-326.
7. Shahbazian, M, Young, J, Yuva-Paylor, L, Spencer, C, Antalffy, B, Noebels, J, et al. (2002). Mice with truncated MeCP2 recapitulate many Rett syndrome features and display hyperacetylation of histone H3. *Neuron* 35: 243-254.
8. Goffin, D, Allen, M, Zhang, L, Amorim, M, Wang, IT, Reyes, A R, et al. (2011). Rett syndrome mutation MeCP2 T158A disrupts DNA binding, protein stability and ERP responses. *Nat Neurosci* 15: 274-283.
9. Brown, K, Selfridge, J, Lagger, S, Connelly, J, De Sousa, D, Kerr, A, et al. (2016). The molecular basis of variable phenotypic severity among common missense mutations causing Rett syndrome. *Hum Mol Genet* 25: 558-570.
10. Lyst, M J, Ekiert, R, Ebert, D H, Merusi, C, Nowak, J, Selfridge, J, et al. (2013). Rett syndrome mutations abolish the interaction of MeCP2 with the NCoR/SMRT co-repressor. *Nat Neurosci* 16: 898-902.
11. Pitcher, M R, Herrera, J A, Buffington, SA, Kochukov, MY, Merritt, JK, Fisher, A R, et al. (2015). Rett syndrome like phenotypes in the R255X Mecp2 mutant mouse are rescued by MECP2 transgene. *Hum Mol Genet* 24: 2662-2672.
12. Archer, H, Evans, J, Leonard, H, Colvin, L, Ravine, D, Christodoulou, J, et al. (2007). Correlation between clinical severity in patients with Rett syndrome with a p.R168X or p.T158M MECP2 mutation, and the direction and degree of skewing of X-chromosome inactivation. *J Med Genet* 44: 148-152.
13. Ghosh, RP, Horowitz-Scherer, RA, Nikitina, T, Gierasch, LM, and Woodcock, CL (2008). Rett syndrome-causing mutations in human MeCP2 result in diverse structural changes that impact folding and DNA interactions. *J Biol Chem* 283: 20523-20534.
14. Leonard, H, Cobb, S, and Downs, J (2016). Clinical and biological progress over 50 years in Rett syndrome. *Nat Rev Neurol*.
15. Guy, J, Gan, J, Selfridge, J, Cobb, S, and Bird, A (2007). Reversal of neurological defects in a mouse model of Rett syndrome. *Science* 315: 1143-1147.
16. Robinson, L, Guy, J, McKay, L, Brockett, E, Spike, R C, Selfridge, J, et al. (2012). Morphological and functional reversal of phenotypes in a mouse model of Rett syndrome. *Brain* 135: 2699-2710.
17. Jugloff, DG, Vandamme, K, Logan, R, Visanji, NP, Brotchie, J M, and Eubanks, J H (2008). Targeted delivery of an Mecp2 transgene to forebrain neurons improves the behavior of female Mecp2-deficient mice. *Hum Mol Genet* 17: 1386-1396.
18. Gadalla, K K E, Ross, P D, Hector R. D., Bahey, N G, Bailey, M E S, and Cobb, S R (2015). Gene therapy for Rett syndrome: prospects and challenges. *Future Neurology* 10: 467-484.
19. Gadalla, K K, Bailey, M E, Spike, R C, Ross, P D, Woodard, K T, Kalburgi, S N, et al. (2013). Improved survival and reduced phenotypic severity following AAV9/MECP2 gene transfer to neonatal and juvenile male Mecp2 knockout mice. *Mol Ther* 21: 18-30.
20. Matagne, V, Ehinger, Y, Saidi, L, Borges-Correia, A, Barkats, M, Bartoli, M, et al. (2016). A codon-optimized Mecp2 transgene corrects breathing deficits and improves survival in a mouse model of Rett syndrome. *Neurobiol Dis* 99: 1-11.
21. Garg, SK, Lioy, DT, Cheval, H, McGann, J C, Bissonnette, J M, Murtha, M J, et al. (2013). Systemic delivery of MeCP2 rescues behavioral and cellular deficits in female mouse models of Rett syndrome. *J Neurosci* 33: 13612-13620.
22. Gray, S J, Foti, SB, Schwartz, J W, Bachaboina, L, Taylor-Blake, B, Coleman, J, et al. (2011). Optimizing promoters for recombinant adeno-associated virus-mediated gene expression in the peripheral and central nervous system using self-complementary vectors. *Hum Gene Ther* 22: 1143-1153.
23. Ross, PD, Guy, J, Selfridge, J, Kamal, B, Bahey, N, Tanner, K E, et al. (2016). Exclusive expression of MeCP2 in the nervous system distinguishes between brain and peripheral Rett syndrome-like phenotypes. *Hum Mol Genet*.
24. Skene, P J, Illingworth, R S, Webb, S, Kerr, A R, James, K D, Turner, D J, et al. (2010). Neuronal MeCP2 is expressed at near histone-octamer levels and globally alters the chromatin state. *Mol Cell* 37: 457-468.
25. Tornoe, J, Kusk, P, Johansen, T E, and Jensen, PR (2002). Generation of a synthetic mammalian promoter library by modification of sequences spacing transcription factor binding sites. *Gene* 297: 21-32.
26. Levitt, N, Briggs, D, Gil, A, and Proudfoot, N J (1989). Definition of an efficient synthetic poly(A) site. *Genes Dev* 3: 1019-1025.
27. Pulicherla, N, Shen, S, Yadav, S, Debbink, K, Govindasamy, L, Agbandje-McKenna, M, et al. (2011). Engineering liver-detargeted AAV9 vectors for cardiac and musculoskeletal gene transfer. *Mol Ther* 19: 1070-1078.
28. Karumuthil-Melethil, S, Nagabhushan Kalburgi, S, Thompson, P, Tropak, M, Kaytor, M D, Keimel, J G, et al. (2016). Novel Vector Design and Hexosaminidase Variant Enabling Self-Complementary Adeno-Associated Virus for the Treatment of Tay-Sachs Disease. *Hum Gene Ther* 27: 509-521.
29. Liu, J, and Francke, U (2006). Identification of cis-regulatory elements for MECP2 expression. *Human molecular genetics* 15: 1769-1782.
30. Adachi, M, Keefer, E W, and Jones, F S (2005). A segment of the Mecp2 promoter is sufficient to drive expression in neurons. *Human molecular genetics* 14: 3709-3722.
31. Liyanage, V R, Zachariah, R M, and Rastegar, M (2013). Decitabine alters the expression of Mecp2 isoforms via dynamic DNA methylation at the Mecp2 regulatory elements in neural stem cells. *Molecular autism* 4: 46.
32. Feng, Y, Huang, W, Wani, M, Yu, X, and Ashraf, M (2014). Ischemic preconditioning potentiates the protective effect of stem cells through secretion of exosomes by targeting Mecp2 via miR-22. *PLoS One* 9: e88685.

33. Jovicic, A, Roshan, R, Moisoi, N, Pradervand, S, Moser, R, Pillai, B, et al. (2013). Comprehensive expression analyses of neural cell-type-specific miRNAs identify new determinants of the specification and maintenance of neuronal phenotypes. *J Neurosci* 33: 5127-5137.
34. Klein, M E, Lioy, DT, Ma, L, Impey, S, Mandel, G, and Goodman, R H (2007). Homeostatic regulation of MeCP2 expression by a CREB-induced microRNA. *Nat Neurosci* 10: 1513-1514.
35. Visvanathan, J, Lee, S, Lee, B, Lee, J W, and Lee, SK (2007). The microRNA miR-124 antagonizes the anti-neural REST/SCP1 pathway during embryonic CNS development. *Genes Dev* 21: 744-749.
36. Heckman, L D, Chahrour, M H, and Zoghbi, H Y (2014). Rett-causing mutations reveal two domains critical for MeCP2 function and for toxicity in MECP2 duplication syndrome mice. *Elife* 3.
37. Coy, J F, Sedlacek, Z, Bachner, D, Delius, H, and Poustka, A (1999). A complex pattern of evolutionary conservation and alternative polyadenylation within the long 3"-untranslated region of the methyl-CpG-binding protein 2 gene (MeCP2) suggests a regulatory role in gene expression. *Human molecular genetics* 8: 1253-1262.
38. Bagga, J S, and D'Antonio, L A (2013). Role of conserved cis-regulatory elements in the post-transcriptional regulation of the human MECP2 gene involved in autism. *Human genomics* 7: 19.
39. Newnham, CM, Hall-Pogar, T, Liang, S, Wu, J, Tian, B, Hu, J, et al. (2010). Alternative polyadenylation of MeCP2: Influence of cis-acting elements and trans-acting factors. *RNA biology* 7: 361-372.
40. Lewis, BP, Burge, C B, and Bartel, DP (2005). Conserved seed pairing, often flanked by adenosines, indicates that thousands of human genes are microRNA targets. *Cell* 120: 15-20.
41. Vorozheykin, P S, and Titov, II (2015). Web server for prediction of miRNAs and their precursors and binding sites. *Mol Biol+* 49: 755-761.
42. Rehmsmeier, M, Steffen, P, Hochsmann, M, and Giegerich, R (2004). Fast and effective prediction of microRNA/target duplexes. *Rna* 10: 1507-1517.
43. Feng, Y L, Huang, W, Wani, M, Yu, X Y, and Ashraf, M (2014). Ischemic Preconditioning Potentiates the Protective Effect of Stem Cells through Secretion of Exosomes by Targeting Mecp2 via miR-22. *PloS one* 9.
44. Jovicic, A, Roshan, R, Moisoi, N, Pradervand, S, Moser, R, Pillai, B, et al. (2013). Comprehensive Expression Analyses of Neural Cell-Type-Specific miRNAs Identify New Determinants of the Specification and Maintenance of Neuronal Phenotypes. *Journal of Neuroscience* 33: 5127-5137.
45. Deverman, BE, Pravdo, P L, Simpson, BP, Kumar, SR, Chan, K Y, Banerjee, A, et al. (2016). Cre-dependent selection yields AAV variants for widespread gene transfer to the adult brain. *Nature biotechnology* 34: 204-209.
46. Clement, N, and Grieger, J C (2016). Manufacturing of recombinant adeno-associated viral vectors for clinical trials. *Mol Ther Methods Clin Dev* 3: 16002.
47. Gray, S J, Blake, BL, Criswell, HE, Nicolson, S C, Samulski, R J, and McCown, T J (2010). Directed Evolution of a Novel Adeno-associated Virus (AAV) Vector That Crosses the Seizure-compromised Blood-Brain Barrier (BBB). *Mol Ther* 18: 570-578.

The invention claimed is:

1. A nucleic acid molecule comprising a MeCP2 expression cassette, the expression cassette comprising, in operable linkage from 5' to 3':
   (a) a 5' transcriptional control region comprising a promoter capable of driving transcription in neural cells, wherein the promoter is a MeCP2 promoter comprising a MeCP2 silencer element and a CNS regulatory element;
   (b) a Kozak sequence;
   (c) an open reading frame encoding a MeCP2 protein;
   (d) a 3' untranslated region (3'UTR) comprising a MeCP2 polyadenylation signal
      a binding site for miR-22,
      a binding site for miR-19;
      a binding site for miR-132,
      a binding site for miR-124, and
      one or more AU-rich element of the sequence AUUUA; and
   (e) transcriptional termination signals; and
wherein the MeCP2 expression cassette is not more than about 5 kb in length.

2. The nucleic acid molecule of claim 1, wherein the encoded MeCP2 protein comprises:
   (i) a methyl-CpG binding domain (MBD) having a sequence (SEQ ID NO: 5)
PAVPEASASPKQRRSIIRDRGPMYDDPTLPEGWTRKLKQRKSGRSAGKYD
VYLINPQGKAFRSEVELIAYFEKVGDTSLDPNDFDFTVTGRGSPSRREQK
PP, or a variant thereof having at least 70%, at least 75%, at least 80%, at least 85%, at least 90%, at least 95%, at least 96%, at least 97%, at least 98%, or at least 99% identity thereto;
   (ii) a NCoR/SMRT Interaction Domain (NID) having a sequence (SEQ ID NO: 6)
PGSVVAAAAAEAKKKAVKESSIRSVQETVLPIKKRKTRETV, or a variant thereof having at least 70%%, at least 75%, at least 80%, at least 85%, at least 90%, at least 95%, at least 96%, at least 97%, at least 98%, or at least 99% identity thereto; and
   (iii) a nuclear localisation signal (NLS).

3. The nucleic acid molecule of claim 2, wherein the encoded MeCP2 protein comprises a sequence:

(SEQ ID NO: 9)
SEDQDLQGLKDKPLKFKKVKKDKKEEKEGKHEPVQPSAHHSAEPAEAGKA
ETSEGSGSAPAVPEASASPKQRRSIIRDRGPMYDDPTLPEGWTRKLKQRK
SGRSAGKYDVYLINPQGKAFRSKVELIAYFEKVGDTSLDPNDFDFTVTGR
GSPSRREQKPPKKPKSPKAPGTGRGRGRPKGSGTTRPKAATSEGVQVKRV
LEKSPGKLLVKMPFQTSPGGKAEGGGATTSTQVMVIKRPGRKRKAEADPQ
AIPKKRGRKPGSVVAAAAAEAKKKAVKESSIRSVQETVLPIKKRKTRETV
SIEVKEVVKPLLVSTLGEKSGKGLKTCKSPGRKSKESSPKGRSSSASSPP
KKEHHHHHHHSESPKAPVPLLPPLPPPPEPESSEDPTSPPEPQDLSSSV
CKEEKMPRGGSLESDGCPKEPAKTQPAVATAATAAEKYKHRGEGERKDIV
SSSMPRPNREEPVDSRTPVTERVSS;

or is a functional variant thereof having at least 70%, at least 75%, at least 80%, at least 85%, at least 90%, at least 95%, at least 96%, at least 97%, at least 98%, or at least 99% identity thereto; or is a functional fragment thereof.

4. The nucleic acid molecule of claim 2, wherein the encoded MeCP2 protein comprises a sequence:

(SEQ ID NO: 10)
PAVPEASASPKQRRSIIRDRGPMYDDPTLPEGWTRKLKQRKSGRSAGKYD
VYLINPQGKAFRSKVELIAYFEKVGDTSLDPNDFDFTVTGRGSPSRREQK
PPKKPKSPKAPGTGRGRGRPKGSGTTRPKRATSEGVQVKRVLEKSPGKLL
VKMPFQTSPGGKAEGGGATTSTQVMVIKRPGRKRKAEADPQAIPKKRGRK
PGSVVAAAAAEAKKKAVKESSIRSVQETVLPTKKRKTRETV;

or is a variant thereof having at least 70%, at least 75%, at least 80%, at least 85%, at least 90%, at least 95%, at least 96%, at least 97%, at least 98%, or at least 99% identity thereto.

5. The nucleic acid molecule of claim 2, wherein the encoded MeCP2 protein comprises a sequence:

(SEQ ID NO: 11)
PAVPEASASPKQRRSIIRDRGPMYDDPTLPEGWTRKLKQRKSGRSAGKYD
VYLINPQGKAFRSKVELIAYFEKVGDTSLDPNDFDFTVTGRGSPSRREQK
PPGSSGSSGPKKKRKVPGSVVAAAAAEAKKKAVKESSIRSVQETVLPIKK
RKTRETV.

6. The nucleic acid molecule of claim 2, wherein the MeCP2 protein further comprises an N-terminal portion having a sequence MAAAAAAAPSGGGGGGEEERLEEK (SEQ ID NO: 12), MVAGMLGLREEK (SEQ ID NO: 13).

7. The nucleic acid molecule of claim 1, wherein the 5' transcription regulatory region comprises a core MeCP2 promoter, a MeCP2 silencer element, a CNS regulatory element, or any combination thereof.

8. The nucleic acid molecule of claim 1, wherein the expression cassette is not more than about 4.9 kb, 4.8 kb, 4.7 kb, 4.6 kb, 4.5 kb or 4.4 kb in length.

9. The nucleic acid molecule of claim 1, further comprising a 5' ITR and a 3' ITR, wherein the 5' ITR and the 3' ITR flank the expression cassette.

10. The nucleic acid molecule of claim 9, wherein the nucleic acid molecule comprises a rAAV genome.

11. The nucleic acid molecule of claim 1, wherein the expression cassette is not more than about 2.4 kb, not more than 2.3 kb, or not more than 2.2 kb in length.

12. The nucleic acid molecule of claim 11, further comprising, from 5' to 3', a MeCP2 expression cassette and the reverse complement of said expression cassette.

13. The nucleic acid molecule of claim 12, further comprising a 5' ITR and a 3' ITR.

14. The nucleic acid molecule of claim 13, wherein the nucleic acid molecule is a scAAV vector genome.

15. An AAV virion particle comprising a nucleic acid molecule as defined by claim 14 or a nucleic acid molecule as defined by claim 14.

16. A pharmaceutical composition comprising a nucleic acid molecule of claim 1, a rAAV genome of claim 10, a scAAV genome of claim 14, or an AAV virion particle according to claim 15, in combination with a pharmaceutically acceptable carrier.

17. The pharmaceutical composition of claim 16, formulated for intravenous or intrathecal administration.

* * * * *